US011191946B2

(12) United States Patent
Snyder et al.

(10) Patent No.: US 11,191,946 B2
(45) Date of Patent: Dec. 7, 2021

(54) IMPLANTABLE BLOOD PUMPS COMPRISING A LINEAR BEARING

(71) Applicant: CorWave SA, Clichy (FR)

(72) Inventors: Trevor Snyder, La Celle-Saint-Cloud (FR); Carl N. Botterbusch, Wyomissing, PA (US); Petrus Le Blanc, Rancho Cordova, CA (US); Bastien Wittig, Epernon (FR)

(73) Assignee: CorWave SA, Clichy (FR)

( * ) Notice: Subject to any disclaimer, the term of this patent is extended or adjusted under 35 U.S.C. 154(b) by 0 days.

(21) Appl. No.: 17/193,867

(22) Filed: Mar. 5, 2021

(65) Prior Publication Data

US 2021/0275797 A1 Sep. 9, 2021

Related U.S. Application Data

(60) Provisional application No. 62/986,602, filed on Mar. 6, 2020.

(51) Int. Cl.
*A61M 60/818* (2021.01)
*A61M 60/178* (2021.01)
*A61M 60/419* (2021.01)

(52) U.S. Cl.
CPC ........ *A61M 60/818* (2021.01); *A61M 60/178* (2021.01); *A61M 60/419* (2021.01); *A61M 2205/04* (2013.01)

(58) Field of Classification Search
CPC .............. A61M 60/818; A61M 60/419; A61M 60/178; A61M 2205/04

(Continued)

(56) References Cited

U.S. PATENT DOCUMENTS

| 2,842,067 A | 7/1958 | John et al. |
| 3,107,630 A | 10/1963 | Johnson et al. |

(Continued)

FOREIGN PATENT DOCUMENTS

| AU | 2013203301 A1 | 5/2013 |
| AU | 2013203301 B2 | 10/2015 |

(Continued)

OTHER PUBLICATIONS

International Search Report & Written Opinion dated May 14, 2021 in Int'l PCT Patent Appl. Serial No. PCT/IB2021/051879.

(Continued)

*Primary Examiner* — Erin M Piateski
(74) *Attorney, Agent, or Firm* — Eversheds Sutherland (US) LLP; Christopher C. Bolten; Robert D. Ward

(57) ABSTRACT

Systems and methods for generating blood flow with a pump incorporating linear bearing technology are provided. The pump may include an actuator assembly, a moving assembly, and a linear hydrodynamic or thin-film bearing positioned within a housing. The moving assembly may include at least one magnet and the actuator assembly may include a magnetic assembly for selectively generating a magnetic field to cause linear reciprocating movement of the moving assembly with respect to the actuator assembly. The linear hydrodynamic or thin-film bearing may include a bearing portion on the moving assembly that is in fluid communication with a bearing portion on the actuator assembly or pump housing. The system may involve an implantable pump, an extracorporeal battery and a controller coupled to the implantable pump. The implantable pump may be suitable for use as a left ventricular assist device (LVAD).

30 Claims, 52 Drawing Sheets

(58) Field of Classification Search
USPC .......................................................... 600/16
See application file for complete search history.

(56) References Cited

U.S. PATENT DOCUMENTS

| | | | |
|---|---|---|---|
| 3,165,061 A | 1/1965 | Smith et al. | |
| 3,608,088 A | 9/1971 | Dorman et al. | |
| 3,620,651 A | 11/1971 | Peter | |
| 3,743,446 A | 7/1973 | Mandroian | |
| 3,765,175 A | 10/1973 | Ohnaka | |
| 4,063,826 A | 12/1977 | Riepe | |
| 4,277,706 A | 7/1981 | Isaacson | |
| 4,384,830 A | 5/1983 | Wakelin | |
| 4,484,095 A | 11/1984 | Neumann | |
| 4,488,854 A | 12/1984 | Miller | |
| 4,498,851 A | 2/1985 | Kolm et al. | |
| 4,648,807 A | 3/1987 | Tippetts et al. | |
| 4,753,221 A | 6/1988 | Kensey et al. | |
| 4,906,229 A | 3/1990 | Wampler | |
| 4,931,036 A | 6/1990 | Kanai et al. | |
| 4,939,405 A | 7/1990 | Okuyama et al. | |
| 4,955,856 A | 9/1990 | Phillips | |
| 4,995,857 A | 2/1991 | Arnold | |
| 5,147,388 A | 9/1992 | Yamazaki | |
| 5,263,978 A | 11/1993 | Kaufmann et al. | |
| 5,275,580 A | 1/1994 | Yamazaki | |
| 5,360,445 A | 11/1994 | Goldowsky | |
| 5,370,509 A | 12/1994 | Golding et al. | |
| 5,525,041 A | 6/1996 | Deak | |
| 5,588,812 A | 12/1996 | Taylor et al. | |
| 5,840,070 A * | 11/1998 | Wampler | H02K 5/1285 604/131 |
| 5,982,801 A | 11/1999 | Deak | |
| 6,030,336 A | 2/2000 | Franchi | |
| 6,058,593 A | 5/2000 | Siess | |
| 6,079,214 A | 6/2000 | Bishop | |
| 6,083,260 A | 7/2000 | Aboul-Hosn | |
| 6,116,862 A | 9/2000 | Rau et al. | |
| 6,123,725 A | 9/2000 | Aboul-Hosn | |
| 6,176,822 B1 | 1/2001 | Nix et al. | |
| 6,176,848 B1 | 1/2001 | Rau et al. | |
| 6,346,071 B1 | 2/2002 | Mussivand | |
| 6,361,284 B2 | 3/2002 | Drevet | |
| 6,395,026 B1 | 5/2002 | Aboul-Hosn et al. | |
| 6,530,876 B1 | 3/2003 | Spence | |
| 6,532,964 B2 | 3/2003 | Aboul-Hosn et al. | |
| 6,658,740 B2 | 12/2003 | Habben | |
| 6,659,740 B2 | 12/2003 | Drevet | |
| 6,672,847 B2 | 1/2004 | Dooley | |
| 6,723,039 B2 | 4/2004 | French et al. | |
| 6,726,648 B2 | 4/2004 | Kaplon et al. | |
| 6,732,501 B2 | 5/2004 | Yu et al. | |
| 6,811,381 B2 | 11/2004 | Dooley | |
| 6,848,001 B1 | 1/2005 | Sakamoto et al. | |
| 6,935,344 B1 | 8/2005 | Aboul-Hosn et al. | |
| 6,976,996 B1 | 12/2005 | Aboul-Hosn | |
| 7,011,620 B1 | 3/2006 | Siess | |
| 7,027,875 B2 | 4/2006 | Siess et al. | |
| 7,182,727 B2 | 2/2007 | Aboul-Hosn | |
| 7,323,961 B2 | 1/2008 | Drevet | |
| 7,520,850 B2 | 4/2009 | Brockway | |
| 7,696,634 B2 | 4/2010 | Filardo | |
| 7,736,296 B2 | 6/2010 | Siess et al. | |
| 7,839,007 B2 | 11/2010 | Filardo | |
| 7,863,768 B2 | 1/2011 | Filardo | |
| 7,889,877 B2 | 2/2011 | Lutz | |
| 7,988,728 B2 | 8/2011 | Ayre | |
| 8,012,079 B2 | 9/2011 | Delgado, III | |
| 8,152,845 B2 | 4/2012 | Bourque | |
| 8,157,720 B2 | 4/2012 | Marseille et al. | |
| 8,167,593 B2 | 5/2012 | Gohean et al. | |
| 8,333,686 B2 | 12/2012 | Marseille et al. | |
| 8,343,029 B2 | 1/2013 | Farnan et al. | |
| 8,366,401 B2 | 2/2013 | Pate et al. | |
| 8,394,009 B2 | 3/2013 | Bolyard et al. | |
| 8,394,010 B2 | 3/2013 | Farnan | |
| 8,432,057 B2 | 4/2013 | Filardo | |
| 8,449,444 B2 | 5/2013 | Poirier | |
| 8,465,410 B2 | 6/2013 | Marseille et al. | |
| 8,512,012 B2 | 8/2013 | Akdis et al. | |
| 8,550,975 B2 | 10/2013 | Foster | |
| 8,556,795 B2 | 10/2013 | Bolyard et al. | |
| 8,562,508 B2 | 10/2013 | Dague et al. | |
| 8,585,571 B2 | 11/2013 | Bachman et al. | |
| 8,597,350 B2 | 12/2013 | Rudser et al. | |
| 8,610,304 B2 | 12/2013 | Filardo | |
| 8,714,944 B2 | 5/2014 | Drevet | |
| 8,753,256 B2 | 6/2014 | Bolyard et al. | |
| 8,784,291 B2 | 7/2014 | Farnan et al. | |
| 8,821,366 B2 | 9/2014 | Farnan et al. | |
| 8,821,527 B2 | 9/2014 | Farnan et al. | |
| 8,827,888 B2 | 9/2014 | Bolyard et al. | |
| 8,834,136 B2 | 9/2014 | Drevet | |
| 8,852,072 B2 | 10/2014 | LaRose et al. | |
| 8,870,739 B2 | 10/2014 | LaRose et al. | |
| 8,956,275 B2 | 2/2015 | Bolyard et al. | |
| 8,976,546 B2 | 3/2015 | Wang et al. | |
| 9,022,916 B2 | 5/2015 | Farnan et al. | |
| 9,080,564 B2 | 7/2015 | Drevet | |
| 9,089,635 B2 | 7/2015 | Reichenbach et al. | |
| 9,144,669 B2 | 9/2015 | Wieselthaler | |
| 9,145,875 B2 | 9/2015 | Filardo | |
| 9,173,984 B2 | 11/2015 | LaRose et al. | |
| 9,211,367 B2 | 12/2015 | Farnan et al. | |
| 9,308,304 B2 | 4/2016 | Peters et al. | |
| 9,446,180 B2 | 9/2016 | Vadala, Jr. et al. | |
| 9,526,819 B2 | 12/2016 | Chen | |
| 9,572,915 B2 | 2/2017 | Heuring et al. | |
| 9,579,437 B2 | 2/2017 | LaRose et al. | |
| 9,616,158 B2 | 4/2017 | Yaghdjian | |
| 9,694,123 B2 | 7/2017 | Bourque et al. | |
| 9,731,057 B2 | 8/2017 | Garrigue | |
| 9,744,279 B2 | 8/2017 | Tamez et al. | |
| 9,786,150 B2 | 10/2017 | Kimball et al. | |
| 9,861,728 B2 | 1/2018 | Farnan et al. | |
| 9,956,333 B2 | 5/2018 | LaRose et al. | |
| 9,968,720 B2 | 5/2018 | Botterbusch et al. | |
| 10,166,319 B2 | 1/2019 | Botterbusch et al. | |
| 10,188,779 B1 * | 1/2019 | Polverelli | A61M 60/857 |
| 10,398,821 B2 | 9/2019 | Botterbusch et al. | |
| 10,799,625 B2 | 10/2020 | Scheffler et al. | |
| 10,933,181 B2 | 3/2021 | Le Duc De Lillers et al. | |
| 11,097,091 B2 | 8/2021 | Botterbusch et al. | |
| 2001/0001278 A1 | 5/2001 | Drevet | |
| 2002/0095210 A1 | 7/2002 | Finnegan et al. | |
| 2002/0146333 A1 | 10/2002 | Drevet | |
| 2002/0165426 A1 | 11/2002 | Sporer et al. | |
| 2003/0002325 A1 | 1/2003 | Alvandpour et al. | |
| 2004/0002624 A1 | 1/2004 | Yu et al. | |
| 2005/0031474 A1 | 2/2005 | Zackl | |
| 2005/0261543 A1 | 11/2005 | Abe et al. | |
| 2005/0288543 A1 | 12/2005 | Stenberg et al. | |
| 2006/0014999 A1 | 1/2006 | Heilman et al. | |
| 2006/0155158 A1 | 7/2006 | Aboul-Hosn | |
| 2006/0288543 A1 | 12/2006 | Lubera et al. | |
| 2007/0299297 A1 | 12/2007 | Jarvik | |
| 2008/0232987 A1 | 9/2008 | Drevet | |
| 2009/0082778 A1 | 3/2009 | Beane et al. | |
| 2010/0234941 A1 | 9/2010 | Finocchiaro et al. | |
| 2010/0241223 A1 | 9/2010 | Lee et al. | |
| 2011/0124950 A1 | 5/2011 | Foster | |
| 2011/0176945 A1 | 7/2011 | Drevet | |
| 2011/0176946 A1 | 7/2011 | Drevet | |
| 2011/0260449 A1 | 10/2011 | Pokorney | |
| 2012/0089225 A1 * | 4/2012 | Akkerman | A61M 60/824 623/3.13 |
| 2012/0220816 A1 | 8/2012 | Peters et al. | |
| 2012/0323318 A1 | 12/2012 | Yusuf et al. | |
| 2013/0078122 A1 | 3/2013 | Drevet | |
| 2013/0178694 A1 | 7/2013 | Jeffery et al. | |
| 2013/0314047 A1 | 11/2013 | Eagle et al. | |
| 2014/0023533 A1 | 1/2014 | Ishii et al. | |
| 2014/0187852 A1 | 7/2014 | Peters et al. | |
| 2014/0207232 A1 | 7/2014 | Garrigue | |

(56) References Cited

U.S. PATENT DOCUMENTS

| | | |
|---|---|---|
| 2014/0275723 A1 | 9/2014 | Fritz, IV et al. |
| 2014/0277423 A1 | 9/2014 | Alkhatib et al. |
| 2014/0316426 A1 | 10/2014 | Gollner et al. |
| 2015/0167659 A1 | 6/2015 | Sauer |
| 2015/0330383 A1 | 11/2015 | Letailleur et al. |
| 2016/0038664 A1 | 2/2016 | Callaway et al. |
| 2016/0051738 A1 | 2/2016 | Callaway et al. |
| 2016/0235899 A1 | 8/2016 | Yu et al. |
| 2016/0243294 A1 | 8/2016 | Peters et al. |
| 2017/0012491 A1 | 1/2017 | Schob et al. |
| 2017/0266358 A1 | 9/2017 | Aber |
| 2017/0290966 A1 | 10/2017 | Botterbusch et al. |
| 2017/0290967 A1* | 10/2017 | Botterbusch ........ A61M 60/268 |
| 2017/0296723 A1 | 10/2017 | Garrigue |
| 2018/0038364 A1 | 2/2018 | Dumas et al. |
| 2018/0050143 A1 | 2/2018 | Nguyen et al. |
| 2018/0256798 A1 | 9/2018 | Botterbusch et al. |
| 2018/0369469 A1 | 12/2018 | Le Duc De Lillers et al. |
| 2019/0125949 A1 | 5/2019 | Botterbusch et al. |
| 2019/0381227 A1 | 12/2019 | Botterbusch et al. |
| 2020/0368417 A1 | 11/2020 | Polverelli et al. |
| 2021/0170160 A1 | 6/2021 | Le Duc De Lillers et al. |
| 2021/0172429 A1 | 6/2021 | Drevet et al. |

FOREIGN PATENT DOCUMENTS

| | | |
|---|---|---|
| EP | 0412856 A1 | 2/1991 |
| EP | 0415949 A1 | 3/1991 |
| EP | 0445782 B1 | 8/1994 |
| EP | 0925081 B1 | 12/2003 |
| EP | 0961621 B1 | 7/2004 |
| EP | 1551500 A2 | 7/2005 |
| EP | 1233797 B1 | 7/2006 |
| EP | 1337288 B1 | 3/2008 |
| EP | 1981585 A2 | 10/2008 |
| EP | 1644639 B1 | 2/2009 |
| EP | 2152339 A1 | 2/2010 |
| EP | 2249746 A1 | 11/2010 |
| EP | 2310067 A1 | 4/2011 |
| EP | 2600918 A1 | 6/2013 |
| EP | 2517739 B1 | 12/2013 |
| EP | 2704761 A1 | 3/2014 |
| EP | 2310067 B1 | 4/2014 |
| EP | 2753389 A1 | 7/2014 |
| EP | 2152339 B1 | 5/2015 |
| EP | 2891502 A1 | 7/2015 |
| EP | 2704761 B1 | 9/2015 |
| EP | 2736552 B1 | 9/2015 |
| EP | 2891502 B1 | 7/2016 |
| EP | 2164542 B1 | 8/2016 |
| EP | 2856190 B1 | 9/2016 |
| EP | 3145558 A2 | 3/2017 |
| FR | 355700 A | 11/1905 |
| FR | 2650862 B1 | 11/1991 |
| FR | 2744769 A1 | 8/1997 |
| FR | 2744769 B1 | 2/1999 |
| FR | 2861910 B1 | 1/2006 |
| FR | 2905147 A1 | 2/2008 |
| FR | 3032917 A1 | 8/2016 |
| GB | 662047 A | 11/1951 |
| KR | 20130068373 A | 6/2013 |
| WO | WO-8910763 A1 | 11/1989 |
| WO | WO-9008260 A1 | 7/1990 |
| WO | WO-9729282 A1 | 8/1997 |
| WO | WO-9959652 A1 | 11/1999 |
| WO | WO-2007053881 A1 | 5/2007 |
| WO | WO-2011056823 A2 | 5/2011 |
| WO | WO-2017087717 A1 | 5/2017 |
| WO | WO-2017087785 A1 | 5/2017 |
| WO | WO-2019092175 A1 | 5/2019 |
| WO | WO-2020115607 A2 | 6/2020 |

OTHER PUBLICATIONS

Ando, et al., Electrocardiogram-Synchronized Rotational Speed Change Mode in Rotary Pumps Could Improve Pulsatility, Artificial Organs, 35(10):941-947 (2011).

Ando, et al., Left ventricular decompression through a patent foramen ovale in a patient with hypertrophic cardiomyopathy: A case report, Cardiovascular Ultrasound, 2: 1-7 (2004).

Bozkurt, et al., Improving Arterial Pulsatility by Feedback Control of a Continuous Flow Left Ventricular Assist Device via in silico Modeling, International Journal of Artificial Organs, 37(10):773-785 (2014).

Castellanos, et al., Generations of Left Ventricular Assist Devices: The HeartMate Family, Dept. of Bioengineering. Florida Gulf Coast University, BME 3100C, pp. 1-6. (No date available).

Crow, et al., Gastrointestinal Bleeding Rates in Recipients of Nonpulsatile and Pulsatile Left Ventricular Assist Devices, The Journal of Thoracic and Cardiovascular Surgery, 137(1):208-215 (2009).

Fatullayev, et al., Continuous-Flow Left Ventricular Assist Device Thrombosis: A Danger Foreseen is a Danger Avoided, Medical Science Monitor Basic Research, 21:141-144 (2015).

Feier, et al., A Novel, Valveless Ventricular Assist Device: The Fish Tail Pump. First Experimental in Vivo Studies, Artificial Organs, (26)12:1026-1031 (2002).

Fliess, et al., Flatness and Defect of Nonlinear Systems: Introductory Theory and Examples, International Journal of Control, 61(6):1327-1361 (1995).

Fraser et al., A Quantitative Comparison of Mechanical Blood Damage Parameters in Rotary Ventricular Assist Devices: Shear Stress, Exposure Time and Hemolysis Index, Journal of Biomechanical Engineering, 134(8):018002-1 to 018002-11 (2012).

Harris, et al., Ventricular Assist Devices, Continuing Education in Anesthesia, Critical Care & Pain, 12(3):145-151 (2012).

International Search Report & Written Opinion dated Mar. 4, 2019 in Int'l PCT Patent Appl No. PCT/IB2018/059199, 13 pages.

International Search Report & Written Opinion dated Aug. 22, 2017 in Int'l PCT Patent Application Serial No. PCT/IB2017/052069.

International Search Report & Written Opinion dated Jun. 28, 2017 in Int'l PCT Patent Application Serial No. PCT/IB2017/052068.

International Search Report & Written Opinion dated Jul. 15, 2020 in Int'l PCT Patent Appl. Serial No. PCT/IB2019/060144.

International Search Report and Written Opinion dated Apr. 16, 2019 in Int'l PCT Patent Appl. Serial No. PCT/EP2018/080749 (English Translation of ISR only).

International Search Report and Written Opinion dated Jun. 25, 2020 in International PCT Patent Application Serial No. PCT/IB2020/052337.

International Search Report and Written Opinion dated Aug. 3, 2018 in Int'l PCT Patent Appl. Serial No. PCT/IB2018/052215.

Ising, M., RPM and Flow Modulation for a Continuous Flow Left Ventricular Assist Device to Increase Vascular Pulsatility: A Computer Simulation, Mock Circulation, and In-Vivo Animal Study, University of Louisville, Think IR: The University of Louisville's Institutional Repository, Electronic Theses and Dissertations (Jul. 2011).

Islam et al., Left Ventricular Assist Devices and Gastrointestinal Bleeding: A Narrative Review of Case Reports and Case Series, Clinical Cardiology, 36(4):190-200 (2013).

Jorde, et al., Identification and Management of Pump Thrombus in the HeartWare Left Ventricular Assist Device System, JACC: Heart Failure, 3(11):849-856 (2015).

Latham, et al., Parameter Estimation and a Series of Nonlinear Observers for the System Dynamics of a Linear Vapor Compressor, IEEE Transactions on Industrial Electronics, 63(11):6736-6744 (2016).

Leverett, et al., Red Blood Cell Damage by Shear Stress, Biophysical Journal, 12(3):257-273(1972).

(56) References Cited

OTHER PUBLICATIONS

Malehsa, et al., Acquired von Willebrand Syndrome After Exchange of the HeartMate XVE to the HeartMate II Ventricular Assist Device, European Journal of Cardio-Thoracic Surgery, 35(6):1091-1093 (2009).

Mancini, et al., Left Ventricular Assist Devices, A Rapidly Evolving Alternative to Transplant, Journal of the American College of Cardiology, 653:2542-2555 (2015).

Mboup, et al., Numerical Differentiation With Annihilators in Noisy Environment, Numerical Algorithms, 50(4):439-467 (2009).

Menhour, et al., An Efficient Model-Free Setting for Longitudinal and Lateral Vehicle Control: Validation Through the Interconnected Pro-SiVIC/RTMaps Prototyping Platform, IEEE Transactions on Intelligent Transportation Systems, 19(2):461-475 (2018).

Mercorelli, P., A Motion-Sensorless Control for Intake Valves in Combustion Engines, IEEE Transactions on Industrial Electronics, 64(4):3402-3412 (2017).

Mercorelli, P., An Adaptive and Optimized Switching Observer for Sensorless Control of an Electromagnetic Valve Actuator in Camless Internal Combustion Engines, Asian Journal of Control, 16(4):959-973 (2014).

Mohite, et al., Does CircuLite Synergy Assist Device as Partial Ventricular Support have a Place in Modern Management of Advanced Heart Failure?, Expert Rev. Med. Devices, published online Dec. 2, 2014 (pp. 1-12).

Najjar, et al., An Analysis of Pump Thrombus Events in Patients in HeartWare Advance Bridge to Transplant and Continued Access Protocol Trial, The Journal of Heart and Lung Transplantation, 33(1):23-34 (2014).

Pagani, Francis D., MD, PhD, Department of Cardiac Surgery, University of Michigan, "Technology 101: Review of Current Technologies, Types of Flow, Pump Parameters," American Association for Thoracic Surgery, Annual Meeting (2014), Cardiothoracic Transplant and Mechanical Circulatory Support of Heart and Lung Failure.

Perschall, et al., The Progressive Wave Pump: Numerical Multiphysics Investigation of a Novel Pump Concept With Potential to Ventricular Assist Device Application, Artificial Organs, 35(9):E179-E190 (2012).

Rahman, et al., Position Estimation in Solenoid Actuators, IEEE Transactions on Industry Applications, 32(3):552-559 (1996).

Rigatos, G., Differential Flatness Theory ad Flatness-Based Control, in Nonlinear Control and Filtering Using Differential Flatness Approaches, 25(2):47-101 (2015).

Wang, et al., Rotary Blood Pump Control Strategy for Preventing Left Ventricular Suction, ASAIO Journal, 61(1):21-30(2015).

Wang., Quadrotor Analysis and Model Free Control with Comparisons, Universite Paris Sud—Paris XI, (2013).

Weidemann, Daniel., Thesis entitled, Permanent Magnet Reluctance Actuators for Vibration Testing, Completed at the Institute of Applied Mechanics, Technische Universitat Munchen, Apr. 2013.

Yuan, et al., The Spectrum of Complications Following Left Ventricular Assist Device Placement, Journal of Cardiac Surgery, 27:630-638 (2012).

Zhang, et al., Study on Self-Sensor of Linear Moving Magnet Compressor's Piston Stroke, IEEE Sensors Journal, 9(2):154-158 (2009).

U.S. Appl. No. 15/484,101 / U.S. Pat. No. 9,968,720, filed Apr. 10, 2017 / May 15, 2018.

U.S. Appl. No. 15/484,108 / U.S. Pat. No. 10,166,319, filed Apr. 10, 2017 / Jan. 1, 2019.

U.S. Appl. No. 15/940,856 / U.S. Pat. No. 10,933,181, filed Mar. 29, 2018 / Mar. 2, 2021.

U.S. Appl. No. 15/953,269 / U.S. Pat. No. 10,188,779, filed Apr. 13, 2018 / Jan. 29, 2019.

U.S. Appl. No. 15/976,831 / U.S. Pat. No. 10,398,821, filed May 10, 2018 / Sep. 3, 2019.

U.S. Appl. No. 16/234,519, filed Dec. 27, 2018.

U.S. Appl. No. 16/557,711, filed Aug. 30, 2019.

U.S. Appl. No. 16/762,909, filed May 8, 2019.

U.S. Appl. No. 16/766,267, filed May 21, 2020.

U.S. Appl. No. 16/819,021 / U.S. Pat. No. 10,799,625, filed Mar. 13, 2020 / Oct. 31, 2020.

U.S. Appl. No. 17/179,961, filed Feb. 19, 2021.

\* cited by examiner

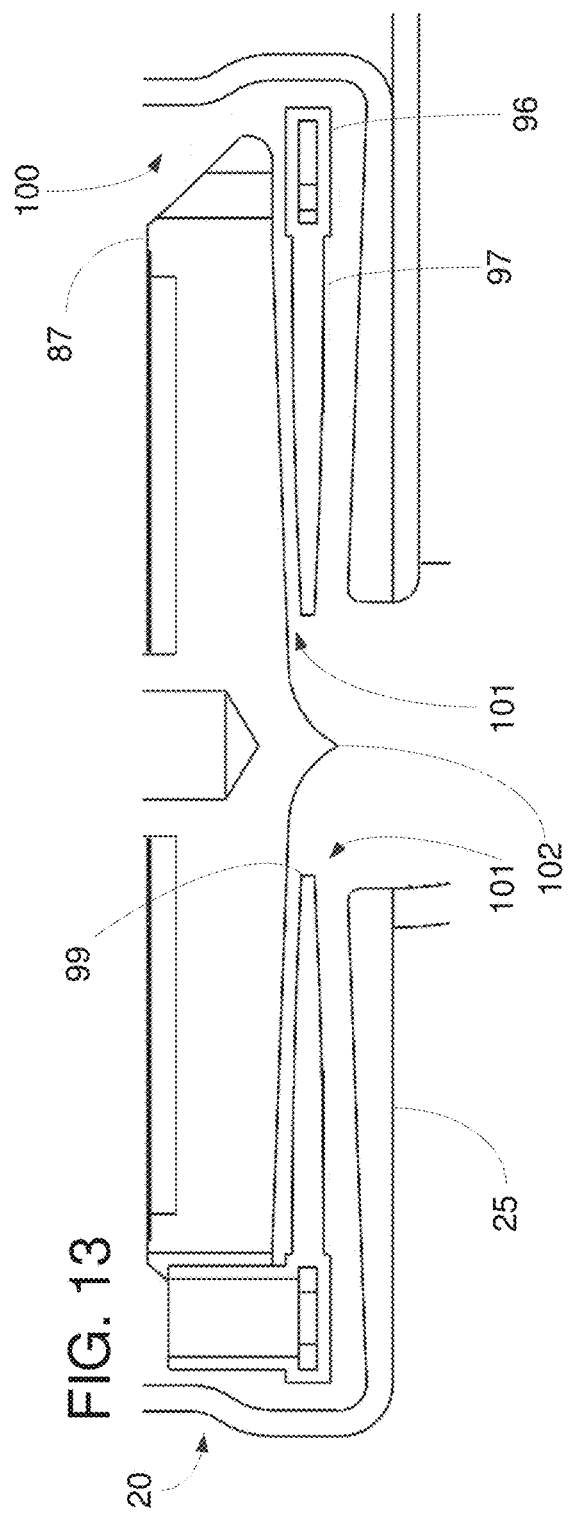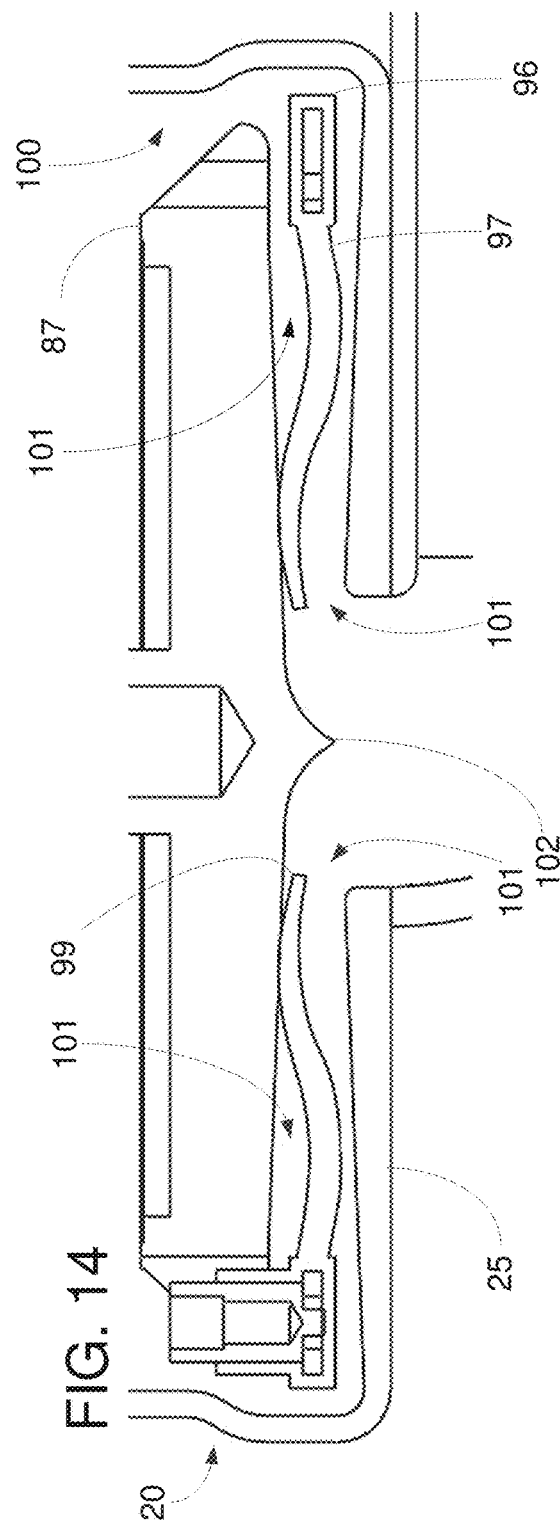

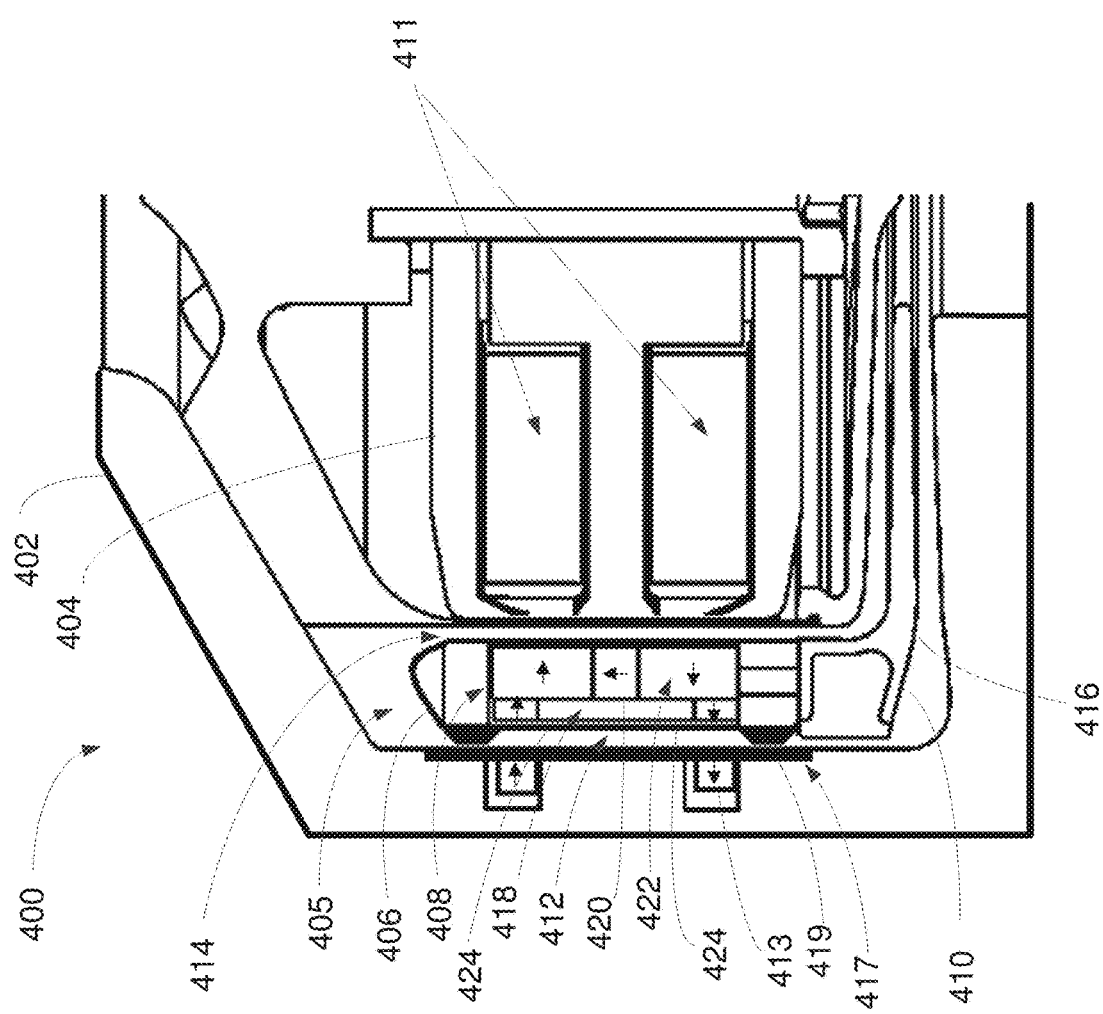

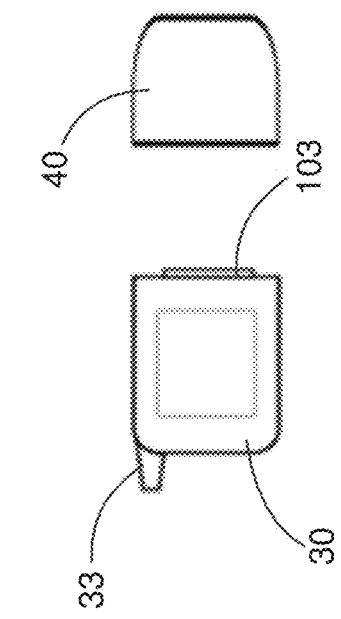
FIG. 21A
FIG. 21B
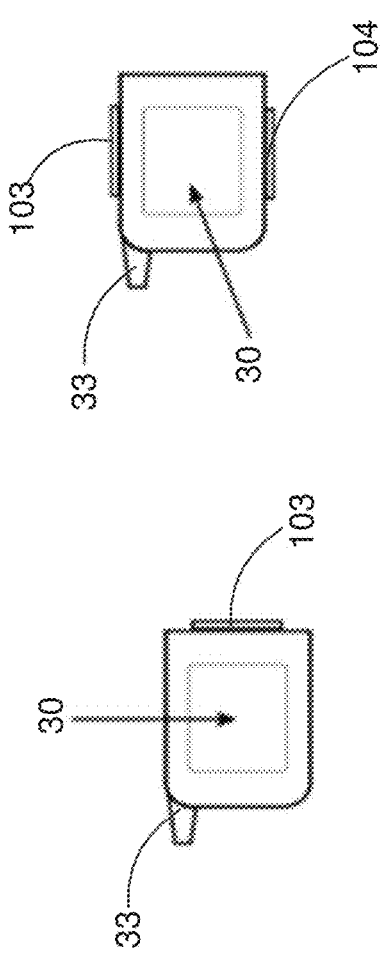
FIG. 21C
FIG. 21D
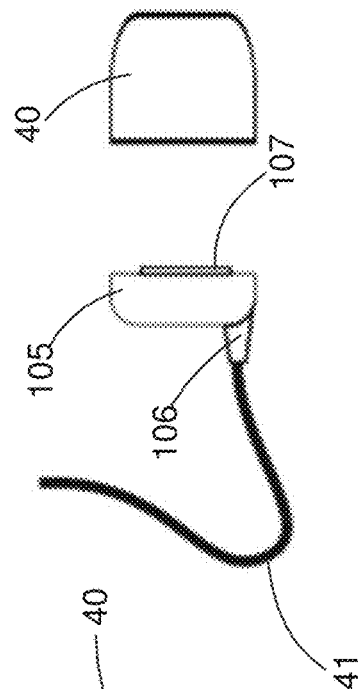
FIG. 21E
FIG. 21F
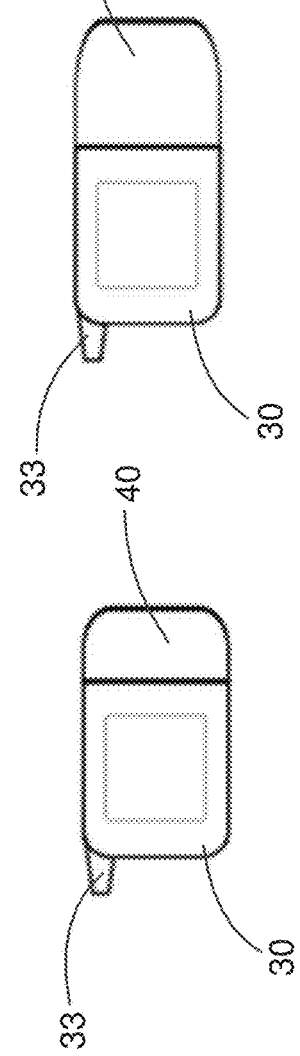

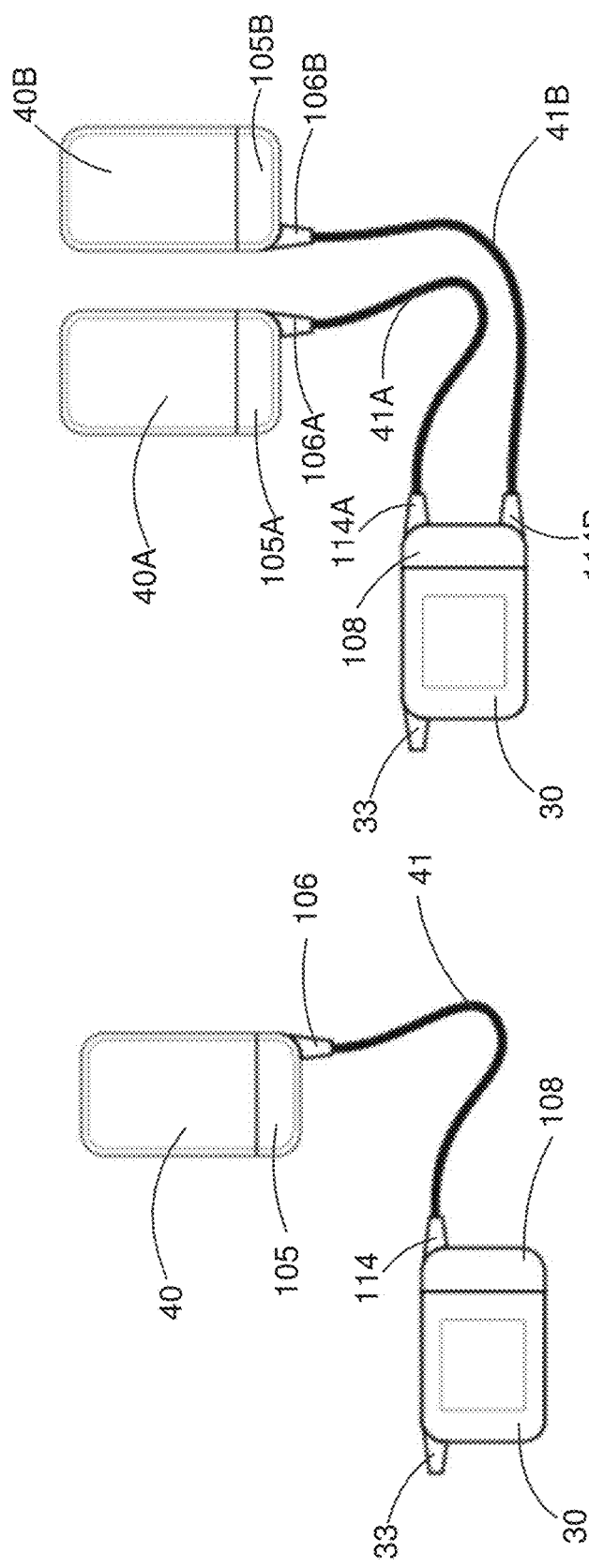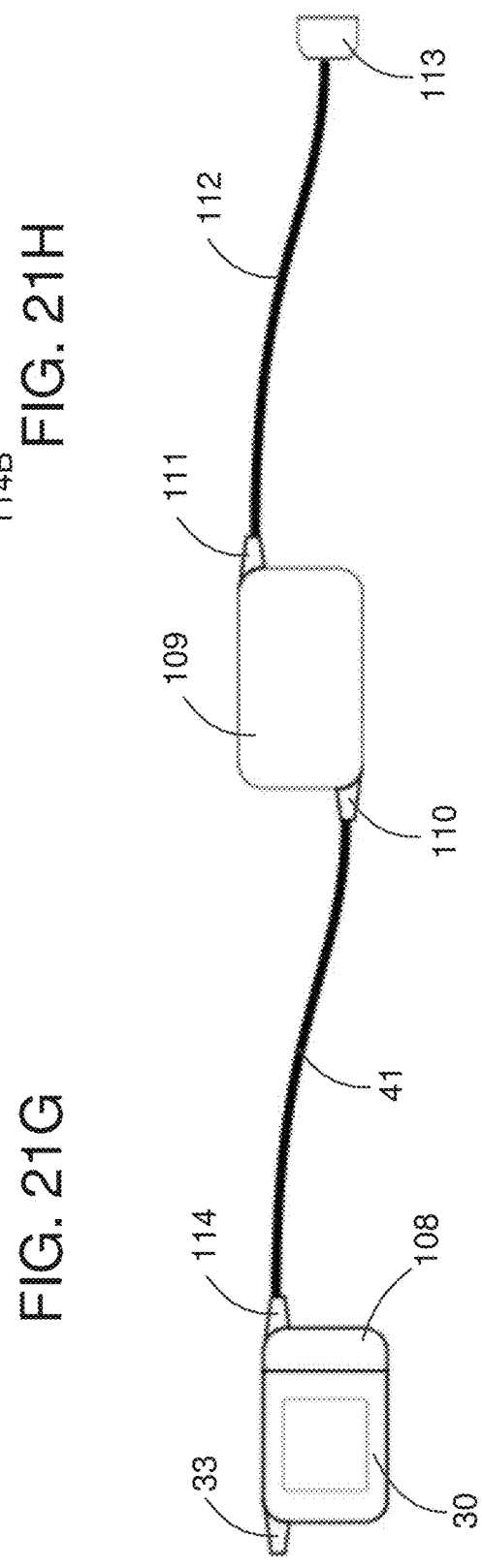

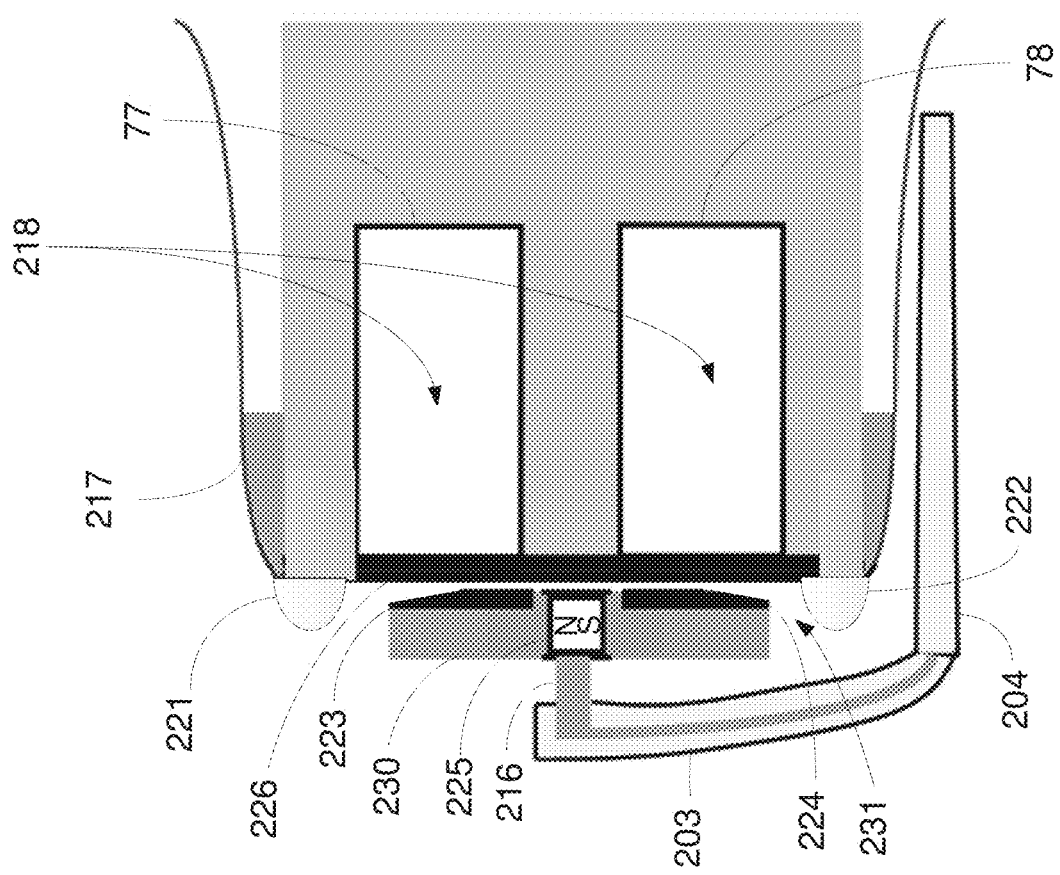
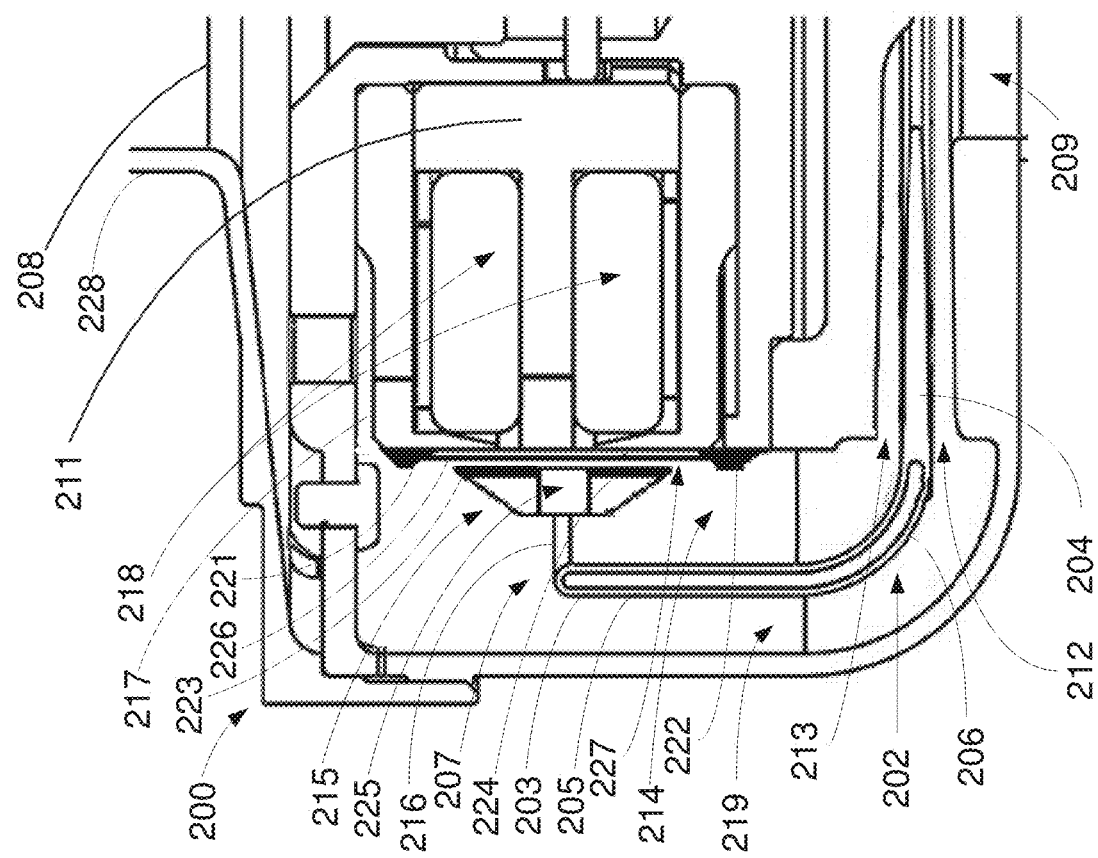
FIG. 34B
FIG. 34A

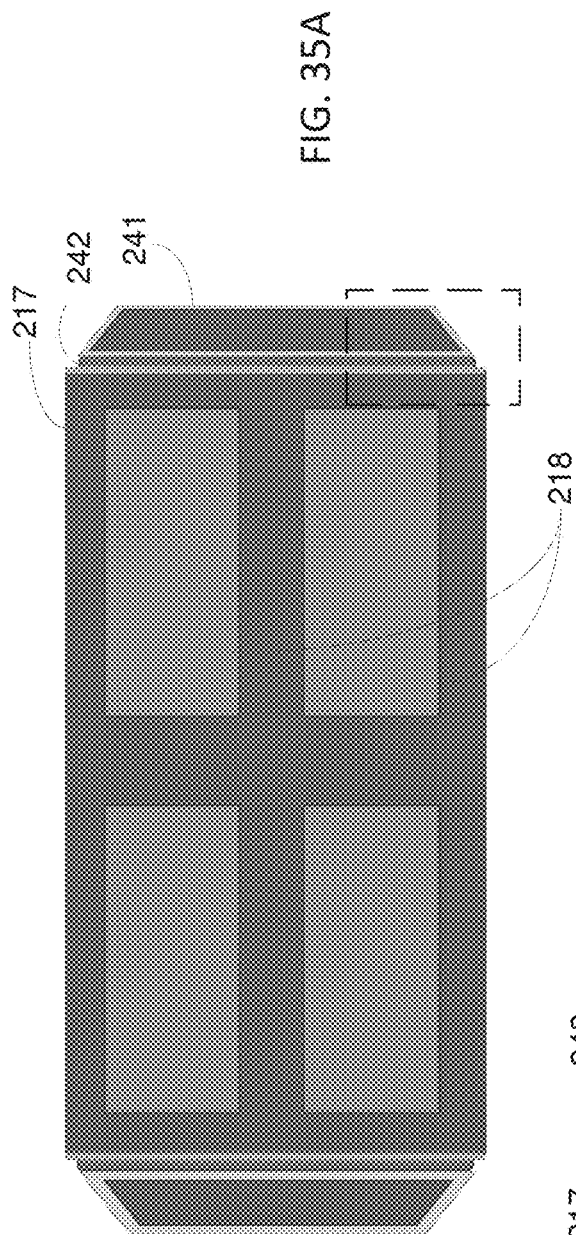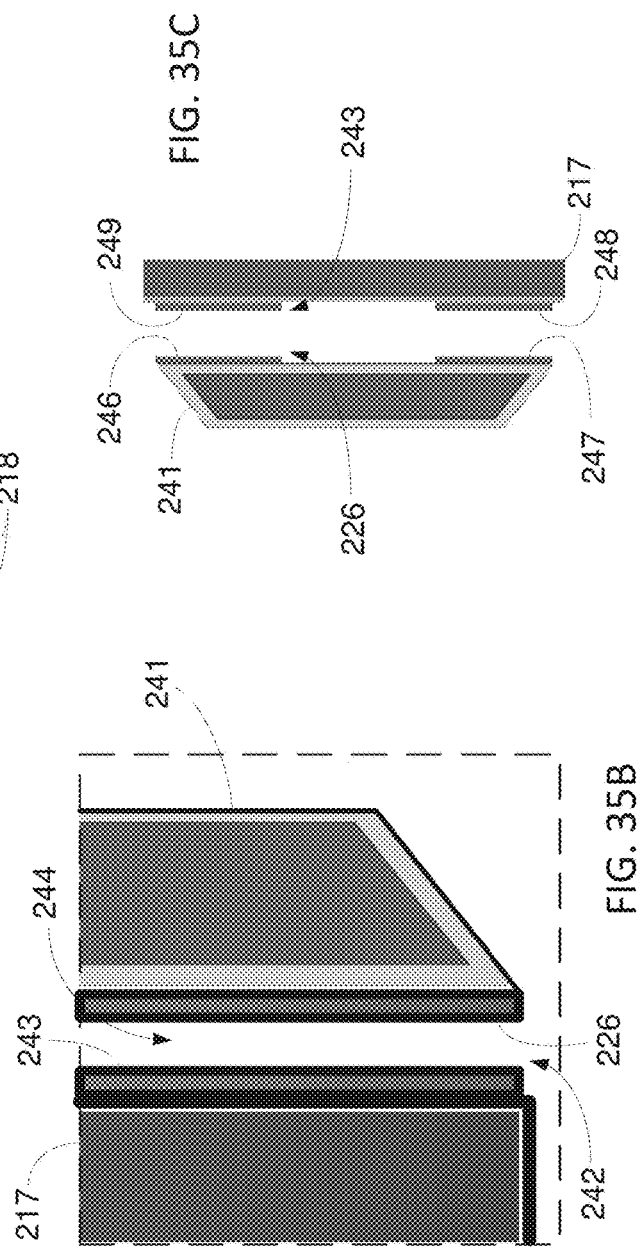
FIG. 35A
FIG. 35B
FIG. 35C

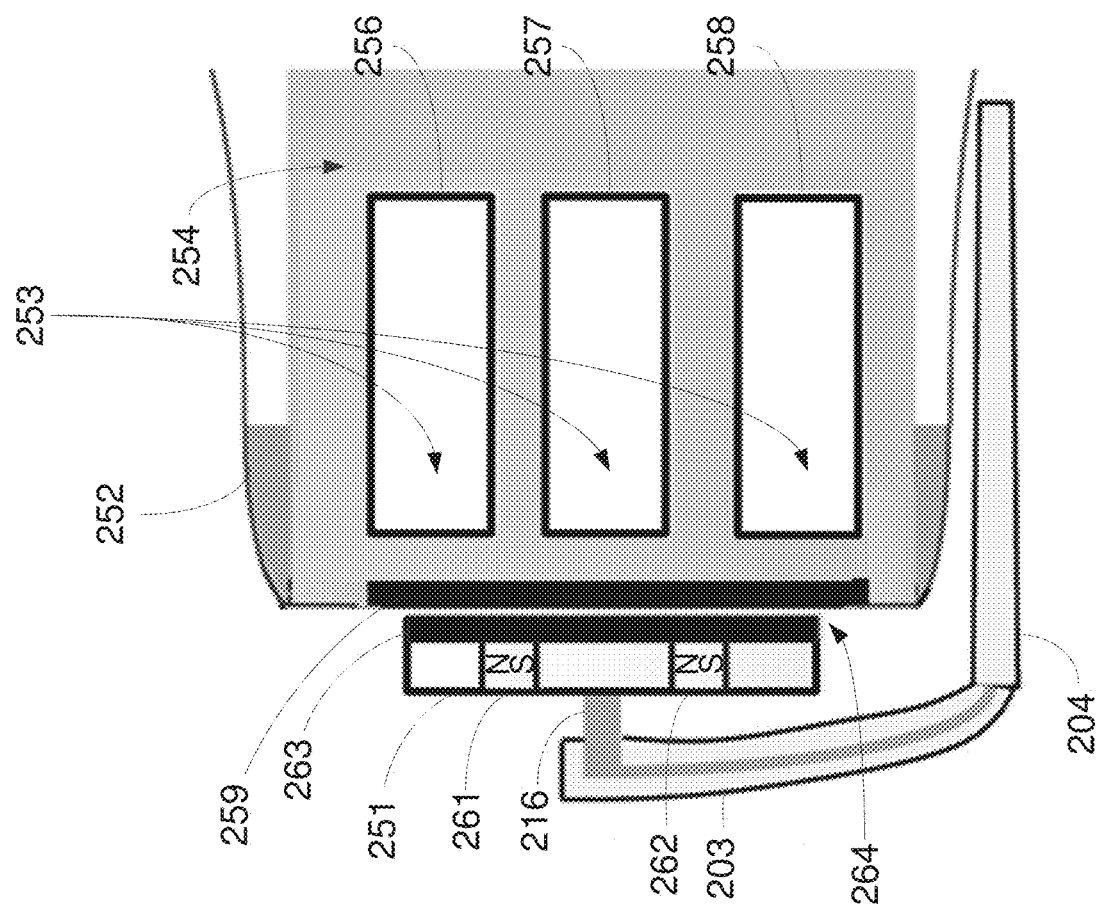

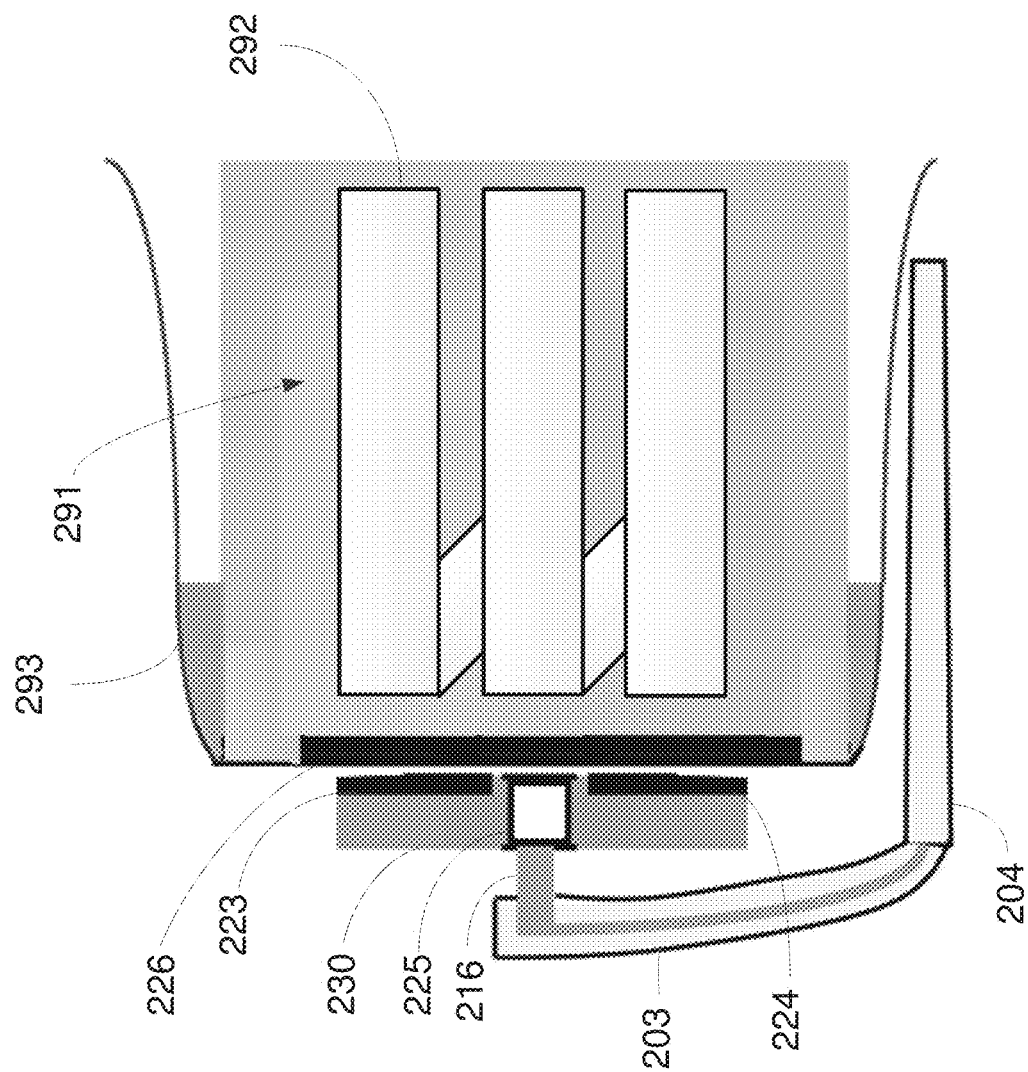

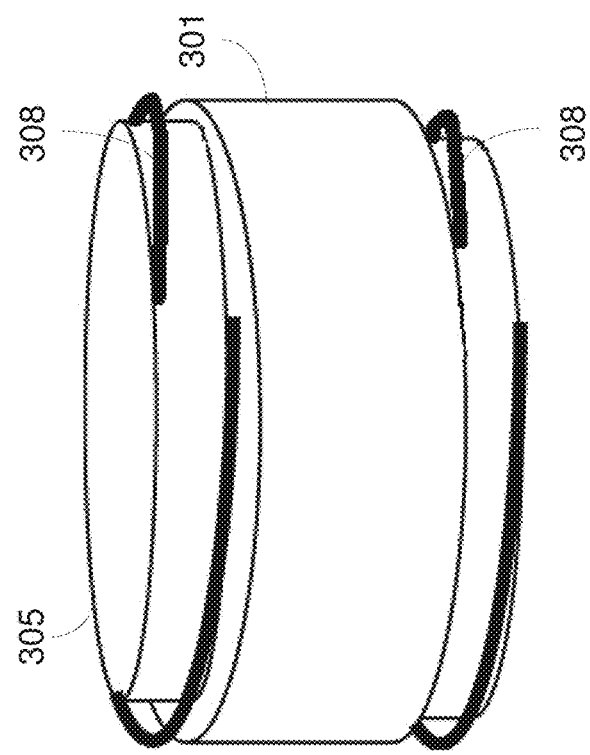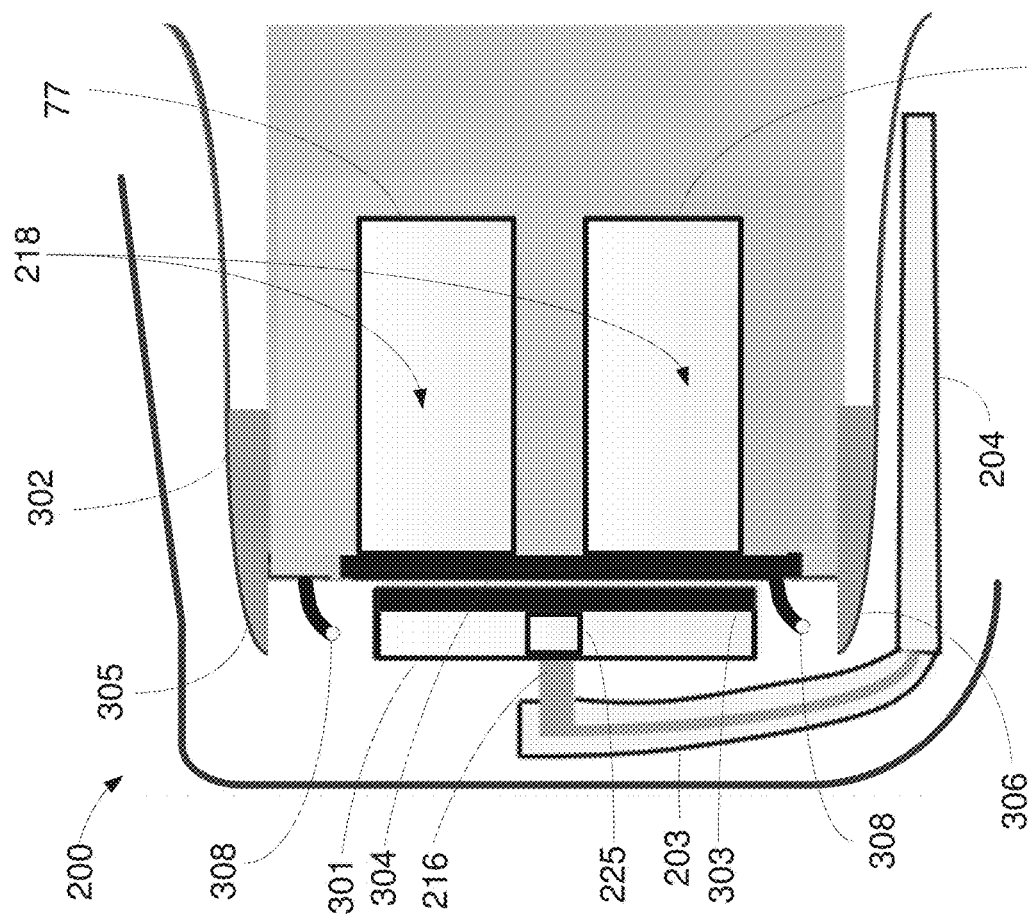
FIG. 41B
FIG. 41A

IMPLANTABLE BLOOD PUMPS COMPRISING A LINEAR BEARING

CROSS-REFERENCE TO RELATED APPLICATION

This application claims priority to U.S. Provisional Application Ser. No. 62/986,602, filed Mar. 6, 2020, the entire contents of which are incorporated herein by reference.

FIELD OF THE INVENTION

The present invention relates generally to implantable heart pumps having an undulating membrane with improved hydraulic performance designed to reduce hemolysis and platelet activation, for example, by incorporating linear bearings based on hydrodynamic or thin-film bearing technology.

BACKGROUND

The human heart is comprised of four major chambers with two ventricles and two atria. Generally, the right-side heart receives oxygen-poor blood from the body into the right atrium and pumps it via the right ventricle to the lungs. The left-side heart receives oxygen-rich blood from the lungs into the left atrium and pumps it via the left ventricle to the aorta for distribution throughout the body. Due to any of a number of illnesses, including coronary artery disease, high blood pressure (hypertension), valvular regurgitation and calcification, damage to the heart muscle as a result of infarction or ischemia, myocarditis, congenital heart defects, abnormal heart rhythms or various infectious diseases, the left ventricle may be rendered less effective and thus unable to pump oxygenated blood throughout the body.

The American Heart Association estimates that about 6 million people in the United States suffer from some form of heart failure. Heart failure is generally categorized into four different stages with the most severe being end stage heart failure. Patients with end stage heart failure may experience heart failure symptoms at rest in spite of medical treatment. Patients at this stage experience heart failure, characterized by decreasing ejection fraction. In patients with systolic heart failure, the walls of the ventricle, which are typically thick in a healthy patient, become thin and weak. Consequently, during systole a reduced volume of oxygenated blood is ejected into circulation, a situation that continues in a downward spiral until death. A patient diagnosed with end stage heart failure has a one-year mortality rate of approximately 50%.

For patients that have reached end stage heart failure, treatment options are limited. In addition to continued use of drug therapy commonly prescribed during earlier stages of heart failure, the treatment options are cardiac transplantation and implantation of a mechanical assist device. While a cardiac transplant may significantly prolong the patient's life, there are only 3,000-3,500 transplants performed in the United States, due to a lack of available donor organs. Thus, patients frequently remain on the transplant waitlist for several months to years awaiting a suitable donor heart. Presently, one alternative to a cardiac transplant is a circulatory assist device. While in recent years circulatory assist devices have improved in design, typically such implants will prolong a patient's life by a few years at most, and include a number of co-morbidities.

One type of circulatory assist device available for patients with end stage heart failure is a left ventricular assist device (LVAD). The LVAD is a surgically implanted pump that draws oxygenated blood from the left ventricle and pumps it directly to the aorta, thereby off-loading (reducing) the pumping work of the left ventricle. LVADs typically are used as a "bridge-to-transplant therapy", "bridge-to-recovery", or "destination therapy." When used for bridge-to-transplant therapy, the LVAD is used to prolong the life of a patient who is waiting for a heart transplant. In bridge-to-recovery therapy, the patient's native heart recovers sufficient function during the period of mechanical circulatory support, the device can be removed from the patient or "de-commissioned," partially remaining in situ. When a patient is not suitable for a heart transplant, the LVAD may be used as a destination therapy to prolong the life, or improve the quality of life, of the patient, but generally such prolongation is for only a couple years.

Generally, a LVAD includes an inlet cannula, a pump, and an outlet cannula, and is coupled to an extracorporeal battery and control unit. The inlet cannula is typically directly connected to the left ventricle, e.g. at the apex, and delivers blood from the left ventricle to the pump. The outlet cannula is typically connected to the aorta distal to the aortic valve and delivers blood from the pump to the aorta. Typically, the outlet cannula of the pump is extended using a hose-type structure, such as a Dacron graft, to reach a proper delivery location on the aorta. Early LVAD designs were of the reciprocating type but more recently rotary and centrifugal pumps have been used.

U.S. Pat. No. 4,277,706 to Isaacson, entitled "Actuator for Heart Pump," describes a LVAD having a reciprocating pump. The pump described in the Isaacson patent includes a housing having an inlet and an outlet, a cavity in the interior of the pump connected to the inlet and the outlet, a flexible diaphragm that extends across the cavity, a plate secured to the diaphragm, and a ball screw that is configured to be reciprocated to drive the plate and connected diaphragm from one end of the cavity to the other end to simulate systole and diastole. The ball screw is actuated by a direct current motor. The Isaacson patent also describes a controller configured to manage the revolutions of the ball screw to control the starting, stopping and reversal of directions to control blood flow in and out of the pump.

Previously-known reciprocating pump LVADs have a number of drawbacks. Such pumps often are bulky, heavy and may require removal of tissue in the chest for implantation. They also require a significant amount of energy to displace the blood by compressing the cavity. Moreover, the pump subjects the blood to significant pressure fluctuations as it passes through the pump as well as high shear forces and risk of hemolysis (e.g., due to valves and/or flow construction). These pressure fluctuations may be exaggerated at higher blood flow rates. Further, depending on the geometry of the pump, areas of little or no flow may result in flow stagnation, which can lead to thrombus formation and potentially fatal medical conditions, such as stroke. Finally, many positive displacement pumps like the one described in the Isaacson patent are incapable of achieving pulsatility similar to that of the natural heart, e.g., roughly 60 to 100 beats per minute, while maintaining physiological pressure gradients.

LVADs utilizing rotary and centrifugal configurations also are known. For example, U.S. Pat. No. 3,608,088 to Reich, entitled "Implantable Blood Pump." describes a centrifugal pump to assist a failing heart. The Reich patent describes a centrifugal pump having an inlet connected to a rigid cannula that is coupled to the left ventricular cavity and a Dacron graft extending from the pump diffuser to the aorta.

A pump includes an impeller that is rotated at high speeds to accelerate blood, and simulated pulsations of the natural heart by changing rotation speeds or introducing a fluid oscillator.

U.S. Pat. No. 5,370,509 to Golding, entitled "Sealless Rotodynamic Pump with Fluid Bearing," describes an axial blood pump capable for use as a heart pump. One embodiment described involves an axial flow blood pump with impeller blades that are aligned with the axes of the blood inlet and blood outlet. U.S. Pat. No. 5,588,812 to Taylor, entitled "Implantable Electrical Axial-Flow Blood Pump," describes an axial flow blood pump similar to that of the Golding patent. The pump described in the Taylor patent has a pump housing that defines a cylindrical blood conduit through which blood is pumped from the inlet to the outlet, and rotor blades that rotate along the axis of the pump to accelerate blood flowing through the blood conduit.

While previously-known LVAD devices have improved, those pump designs are not without problems. Like reciprocating pumps, rotary and centrifugal pumps are often bulky and difficult to implant. Rotary pumps, while mechanically different from positive displacement pumps, also exhibit undesirable characteristics. Like positive displacement pumps, rotary pumps apply significant shear forces to the blood, thereby posing a risk of hemolysis and platelet activation. The very nature of a disk or blade rotating about an axis results in areas of high velocity and low velocity as well as vibration and heat generation. The areas near the leading and trailing edges of the blades and the gap between the blade tip and the housing experience the highest shear forces. In addition, stagnation or low flow rates near the axis of rotation may result in thrombus formation.

While centrifugal pumps may be capable generating pulsatile flow by varying the speed of rotation of the associated disk or blades, this only exacerbates the problems resulting from steep radial velocity profiles and high shear force. In common practice, the output of currently available rotary pumps, measured as flow rate against a given head pressure, is controlled by changing the rotational speed of the pump. Given the mass of the rotating member, the angular velocity of the rotating member, and the resulting inertia, a change in rotational speed may not be instantaneous but instead gradual. Accordingly, while centrifugal pumps may mimic pulsatile flow with speed changes, the resulting pulse may produce physiological pressure changes.

Moreover, rotary pumps typically result in the application of non-physiologic pressure changes on the blood. If the rotational speed of a pump is varied to simulate pulsatile flow or increase flow rate, the rotary pump is less likely to be operated at its optimal operating point, reducing efficiency and increasing energy losses and heat generation.

LVADs may also be configured to increase blood flow to match the demand of the patient. Numerous publications and patents describe methods for adjusting LVAD pump flow to match that demanded by the patient. For example, U.S. Pat. No. 7,520,850 to Brockway, entitled "Feedback control and ventricular assist devices," describes systems and methods for employing pressure feedback to control a ventricular assist device. The system described in the Brockway patent attempts to maintain a constant filling of the ventricle by measuring ventricular pressure and/or ventricular volume. While such systems can achieve flow rates as high as 8 or 9 liters per minute, these flow rates generally are outside of the efficient range of operation for current rotary pumps, which are typically tuned to operate in a range of 4 to 6 liters per minute. Thus, increasing the flow rate in rotary pumps to match patient demanded results in non-optimal pump performance.

Pumps other than of the rotary and positive displacement types are known in the art for displacing fluid. For example, U.S. Pat. Nos. 6,361,284 and 6,659,740, both to Drevet, entitled "Vibrating Membrane Fluid Circulator." describe pumps in which a deformable membrane is vibrated to propel fluid through a pump housing. In these patents, vibratory motion applied to the deformable membrane causes wave-like undulations in the membrane that propel the fluid along a channel. Different flow rates may be achieved by controlling the excitation applied to the membrane.

U.S. Pat. No. 7,323,961 to Drevet, entitled "Electromagnetic Machine with a Deformable Membrane." describes a device in which a membrane is coupled in tension along its outer edge to an electromagnetic device arranged to rotate around the membrane. As the electromagnetic device rotates, the outer edge of the membrane is deflected slightly in a direction normal to the plane of the membrane. These deflections induce a wave-like undulation in the membrane that may be used to move a fluid in contact with the membrane.

U.S. Pat. No. 9,080,564 to Drevet, entitled "Diaphragm Circulator." describes a tensioned deformable membrane in which undulations are created by electromechanically moving a magnetized ring, attached to an outer edge of a deformable membrane, over a coil. Axial displacement of magnetized ring causes undulations of membrane. Like in the '961 patent, the membrane undulations can be controlled by manipulating the magnetic attraction. U.S. Pat. No. 8,714,944 to Drevet, entitled "Diaphragm pump with a Crinkle Diaphragm of Improved Efficiency" and U.S. Pat. No. 8,834,136 to Drevet, entitled "Crinkle Diaphragm Pump" teach similar types of vibrating membrane pumps.

None of the foregoing patents to Drevet describe a vibratory membrane pump suitable for use in a biological setting, or capable of pumping blood over extended periods that present a low risk of flow stagnation leading to thrombus formation.

U.S. Patent Publication Nos. 2017/0290966 and 2017/0290967 to Botterbusch, the entire contents of each of which are incorporated herein by reference, describe implantable cardiovascular blood pumps having a flexible membrane coupled to an electromagnetic actuator assembly that causes wavelike undulations to propagate along the flexible membrane to propel blood through the pump while avoiding thrombus formation, hemolysis and/or platelet activation. The Botterbusch pumps generate hydraulic power—flow and pressure—by translating the linear motion of the electromagnetic actuator, to the flexible membrane, which deforms through its interaction with the blood, translating energy to the blood. The flexible membrane is oriented at a 90° angle to the motion of the linear actuator such that the outer edge of the membrane is the first element to engage the blood. As a result, there is a risk of energy loss at the inlet to the membrane, which affects the hydraulic power generation by the pump.

What is needed is an energy efficient implantable pump having light weight, small size, and fast start and stop response that can operate efficiently and with improved hydraulic performance and minimal blood damage over a wide range of flow rates.

The design of such an energy efficient implantable pump that fulfils all the requirements mentioned above poses many challenges in terms of mechanical design and manufacturing process. It is also a challenge from a control perspective because that unlike rotary pumps, the operation point of a vibrating membrane pump is set by the frequency and amplitude of membrane excitation. Indeed, the higher the frequency or the stroke of the undulation is, the higher the pressure head of the implantable pump may be. The stroke needs to be set accurately with sufficient speed to be able to switch the operating point of the pump fast enough to recreate a sufficient pulse that is synchronized to heartbeats. At the same time, the stroke must be restrained so as not to damage the membrane, blood, or the internal spring components of the pump by excessive stress. This phenomenon can be caused by overpowering the actuator or by the effect of perturbation forces induced by the remaining activity of the left ventricle. Due to the specific medium (blood) in which the pump is operating, it is highly recommended to avoid adding position, velocity, or acceleration sensors that would significantly increase the complexity and size of a pump that is already difficult to design.

Attempts to bypass the use of motion sensors include those that measure current ripple generated by a pulse-width modulation (PWM) voltage input to estimate an equivalent circuit inductance that is related to the magnet position. (See. e.g., M. F. Rahman, et al., Position estimation in solenoid actuators. *IEEE Transactions on Industry Applications*, vol. 32, n. 3, p. 552-559, June 1996). This method only works if the magnetic parts' velocity is close to zero which is not the case of vibrating membrane pump that operates at frequencies close to 100 Hz. Others methods compute the back electromotive force (back EMF proportional to velocity) from an inverted equivalent electric circuit and directly integrate the estimated speed to get the position. (See, e.g., J. Zhang, et al., Study on Self-Sensor of Linear Moving Magnet Compressor's Piston Stroke, *IEEE Sensors Journal*, vol. 9, n. 2, p. 154-158. February 2009). This last method only requires knowledge of electrical parameters, and no information about the mechanical subsystem of the actuator are needed. However, coil current derivative must be computed which is not trivial in a noisy environment.

For example, one method presented a velocity observer to estimate the back EMF that does not rely on computing any time. (See, e.g., J. Latham, et al., Parameter Estimation and a Series of Nonlinear Observers for the System Dynamics of a Linear Vapor Compressor, *IEEE Transactions on Industrial Electronics*, vol. 63, no 11, p. 6736-6744. November 2016). The resulting position from integrating the estimated velocity is sensitive to measurement bias that propagates into the velocity estimation which results in drift when integrated. This effect can be bounded by adding another stage to the observer. (See, e.g., P. Mercorelli. A Motion-Sensorless Control for Intake Valves in Combustion Engines, *IEEE Transactions on Industrial Electronics*, vol. 64, n 4, p. 3402-3412, April 2017). This additional stage adds partial knowledge about the mechanical subsystem of the actuator, and is robust to unknown, bounded forces. However, these studies are limited to a linear domain of the actuator, where the parameters of the equivalent electric circuit of the actuator can be approximated as constants, which is not valid for vibrating membrane pumps where the actuator is made as small as possible.

In view of the foregoing, there exists a need for controlling an energy efficient implantable pump that has light weight, small size, and fast start and stop response.

SUMMARY OF THE INVENTION

The present invention overcomes the drawbacks of previously-known LVAD and implantable pump systems and methods by providing an implantable pump system having an undulating membrane capable of producing a wide range of physiological flow rates while applying low shear forces to the blood, thereby reducing hemolysis and platelet activation relative to previously-known systems. For example, the implantable pump system may incorporate hydrodynamic bearings and/or thin-film bearings to enhance actuation of the pump and facilitate effective blood pumping.

In accordance with one aspect of the present invention, a blood pump may include a housing comprising an inlet and an outlet designed to be in fluid communication with a patient's circulatory system, as well as a pump assembly disposed within the housing. The pump assembly may include an actuator assembly and a linear bearing. The pump assembly may cause linear reciprocating movement using the linear bearing to pump blood from the inlet to the outlet. The actuator assembly may include a magnetic assembly that selectively generates a magnetic field to cause the linear reciprocating movement. The magnetic assembly may include a first coil, a second coil, and a third coil that each are independently activated to generate a magnetic field. Alternatively, the magnetic assembly may include a first coil and a second coil that are independently activated. Alternatively, the magnetic assembly may include a single coil to generate a magnetic field of variable intensity.

The pump assembly may further include a moving assembly coupled to a membrane, the moving assembly may include at least one magnet configured to reciprocate responsive to the magnetic field generated by the actuator assembly. The moving assembly may include at least two magnets with polarity oriented in the same direction. The moving assembly may be concentrically suspended around the actuator assembly. The actuator assembly may include a first resistance magnet positioned above the moving assembly and a second resistance magnet positioned below the moving assembly such that at least one magnet of the moving assembly is oriented such that the first resistance magnet and the second resistance magnet repel the moving assembly.

The linear bearing may include a moving assembly bearing portion disposed on the moving assembly and the actuator assembly may include an actuator assembly bearing portion disposed on the actuator assembly. The actuator assembly bearing portion may be in fluid communication with the moving assembly bearing portion and may be positioned relative to the moving assembly bearing portion such that an opposing pressure force is generated between the moving assembly bearing portion and the actuator assembly bearing portion when the moving assembly moves with respect the actuator assembly. The opposing pressure force may cause the moving assembly bearing portion to assume an offset position a certain distance from the actuator assembly bearing portion as the moving assembly moves with respect the actuator assembly. During operation, blood may enter the inlet of the housing and flow between the moving assembly bearing portion disposed on the moving assembly and the actuator assembly bearing portion disposed on the actuator assembly.

The linear bearing may include a moving assembly bearing portion disposed on the moving assembly and the housing may include a housing bearing portion disposed on an interior of the housing. The housing bearing portion may be in fluid communication with the moving assembly bearing portion and may be positioned relative to the moving assembly bearing portion such that an opposing pressure force may be generated between the moving assembly bearing portion and the housing bearing portion when the moving assembly moves with respect the housing. The opposing pressure force may cause the moving assembly bearing portion to assume an offset position a certain distance from the housing bearing portion as the moving assembly moves with respect the housing. During operation, blood may enter the inlet and flow between the moving assembly bearing portion disposed on the moving assembly and the housing bearing portion disposed on the housing.

The blood pump may be configured to assist the patient's circulatory system without the use of valves. The actuator assembly may include at least one rail indentation and the moving assembly may include at least one moving assembly bearing portion in fluid communication with the at least one rail indentation, the at least one rail indentation configured to guide the moving assembly with respect to the actuator assembly. The moving assembly may include at least one rail indentation and the actuator assembly may include at least actuator assembly bearing portion in fluid communication with the at least one rail indentation. The at least one rail indentation may guide the moving assembly with respect to the actuator assembly.

The actuator assembly may include at least one coil coupled to the moving assembly that extends around the actuator assembly. The coil may dampen linear movement of the moving assembly relative to the actuator assembly and return the moving assembly to a neutral position. The at least one coil may make at least one full revolution around the actuator assembly. The actuator assembly may include at least one spring coupled to the moving assembly to dampen linear movement of the moving assembly relative to the actuator assembly and return the moving assembly to a neutral position.

In accordance with another aspect of the present invention, a blood pump may include a housing having an inlet and an outlet designed to be in fluid communication with a patient's circulatory system, as well as a pump assembly disposed within the housing. The pump assembly may include an actuator, a bearing, and a flexible membrane. The pump assembly may be configured to cause reciprocating movement using the bearing to cause the flexible membrane to move in a wave-like manner to pump blood from the inlet to the outlet. The blood pump may further include a moving assembly coupled to the flexible membrane. The reciprocating movement may cause a pressure in the bearing that offsets the moving assembly from the actuator. The bearing may be designed to maintain a distance between the moving assembly and the actuator. Additionally, or alternatively, the bearing may be designed to minimize contact between the moving assembly and the actuator. In this configuration, at least one magnet may be located in the pump housing in proximity to at least one magnet in the moving assembly to dampen linear movement of the moving assembly relative to the actuator assembly and/or return the moving assembly to a neutral position.

The actuator may include a rail and the moving assembly may engage the rail such that the bearing constrains radial and rotational displacement of the moving assembly with respect to the actuator. The moving assembly may include a first bearing portion and a second bearing portion and the first bearing portion may be axially offset from the second bearing portion. The moving assembly may include a first bearing portion and a second bearing portion and the first bearing portion may be circumferentially offset from the second bearing portion.

In accordance with another aspect of the present invention, a blood pump may include a housing having an inlet and an outlet designed to be in fluid communication with a patient's circulatory system, an actuator assembly coupled to the housing and including at least one coil designed to be selectively activated to generate a magnetic field, a moving assembly including a magnetic assembly designed to interact with the magnetic field, and a flexible membrane coupled to the moving assembly and designed to propel blood from the inlet of the housing to the outlet of the housing. The actuator may be oriented with respect to the housing such that a flow channel is defined by the actuator and the housing. The moving assembly may be circumferentially disposed about the actuator assembly and situated in the flow channel. The moving assembly may partition the flow channel into a first flow channel and a second flow channel.

The moving assembly may be incorporated into the skirt. The moving assembly and the flexible membrane may form a continuous and uninterrupted partition of the flow channel. The magnetic assembly may include a Halbach array. The moving assembly may include a first bearing portion on an interior surface of the moving assembly and the actuator assembly may include a second bearing portion on an exterior surface of the actuator assembly. The first bearing portion and the second bearing portion may be in fluid communication and may generate an opposing pressure force when the moving assembly moves with respect to the actuator assembly. Alternatively, or in addition, the moving assembly may include a first bearing portion on an exterior surface of the moving assembly and the housing may include a second bearing portion on an interior surface of the housing. The first bearing portion and the second bearing portion may be in fluid communication and may generate an opposing pressure force when the moving assembly moves with respect to the housing. In this configuration, at least one magnet may be located in the pump housing in proximity to at least one magnet in the moving assembly to dampen linear movement of the moving assembly relative to the actuator assembly and/or return the moving assembly to a neutral position.

BRIEF DESCRIPTION OF THE DRAWINGS

FIG. 13 is a cross-sectional view of a lower portion of the implantable pump depicting the flow channel and membrane assembly in a resting position.

FIG. 14 is a cross-sectional view of a lower portion of the implantable pump depicting the flow channel and membrane assembly with the membrane undulating.

FIG. 16A illustrates blood flow across a planar ring membrane support, whereas FIG. 16C illustrates a blood pump with an integrated portion incorporating a magnetic assembly featuring linear bearing elements and magnets within the housing, whereas

FIGS. 21A-21H illustrate various configurations of a controller of the present invention, and FIG. 21I illustrates a controller coupled to a power supply.

FIGS. 34A-34B illustrate the pump system with a bearing and resistance magnets in accordance with the principles of the present invention.

FIGS. 35A-35C illustrate a moving assembly and actuator assembly forming a bearing in accordance with the principles of the present invention.

FIG. 36 illustrates a moving assembly and an actuator assembly with three coils forming a bearing in accordance with the principles of the present invention.

FIG. 39 illustrates the moving assembly and an actuator assembly with one coil forming a bearing in accordance with the principles of the present invention.

FIGS. 41A-41B illustrate the moving assembly and an actuator assembly with coil springs and linear bearings in accordance with the principles of the present invention.

DETAILED DESCRIPTION

The pump system of the present invention is particularly well-suited for use as an implantable left ventricular assist device (LVAD), and includes an undulating membrane pump suitable for long-term implantation in a patient having end term heart failure. An implantable pump system constructed in accordance with the principles of the present invention includes an implantable pump and an extracorporeal battery, controller and programmer. The implantable pump includes a housing having an inlet, and outlet, a flexible membrane, and an actuator assembly. When configured as an LVAD, the housing includes an inlet cannula that is inserted into a patient's left ventricle near the apex and an outlet cannula that is surgically placed in fluid communication with the patient's aorta. By activating the actuator assembly within the implantable pump, the membrane is induced to undulate, thereby causing blood to be drawn into the pump through the inlet cannula and expelled through the outlet cannula into the aorta. Flow rate and pulsatility may be manipulated by changing one or more of the frequency, amplitude and duty cycle of the actuator assembly.

For improved hydraulic performance, the implantable pump may include a skirt disposed within the housing to guide blood flow from the inlet of the pump towards the outlet. The skirt may be positioned within the housing such that blood flows across opposing sides of the skirt and towards the undulating membrane upon activation of the pump.

Figure 1:
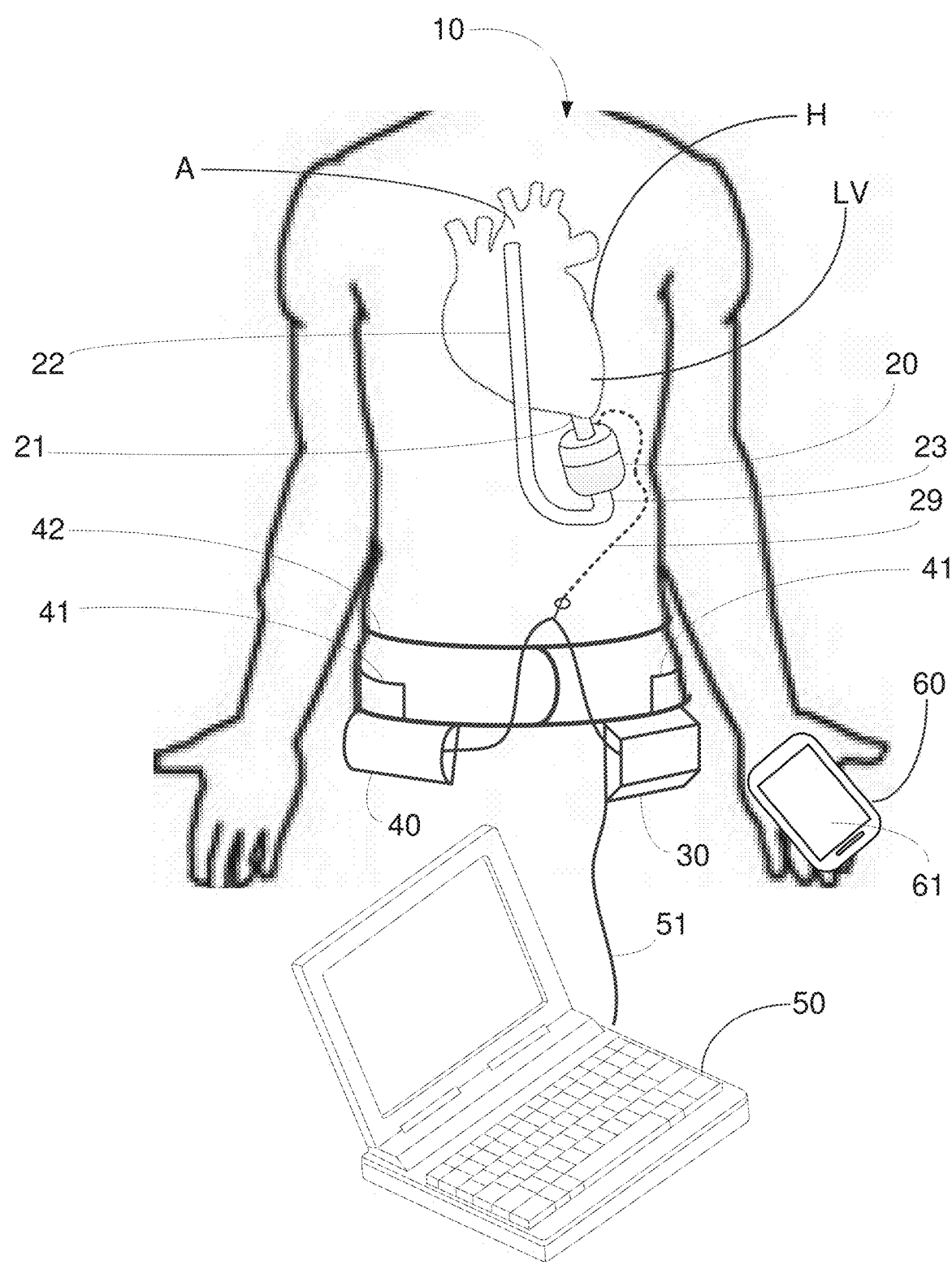
FIG. 1 depicts an exemplary embodiment of the pump system of the present invention comprising an implantable pump, controller, battery, programmer and mobile device.

Referring now to FIG. 1, pump system 10 constructed in accordance with the principles of the present invention is described. Pump system 10 includes implantable pump 20, controller 30, battery 40, programmer 50 and optionally, a software module programmed to run on mobile device 60. Implantable pump 20 is configured to be implanted within a patient's chest so that inlet cannula 21 is coupled to left ventricle LV of heart H. Outlet cannula 22 of pump 20 is configured to be coupled to aorta A. Inlet cannula 21 preferably is coupled to the apex of left ventricle LV, while outlet cannula 22 is coupled to aorta A in the vicinity of the ascending aorta, above the level of the cardiac arteries. Implantable pump 20 may be affixed within the patient's chest using a ring-suture or other conventional technique. Outlet cannula 22, which may comprise a Dacron graft or other synthetic material, is coupled to outlet 23 of implantable pump 20.

Figure 2:
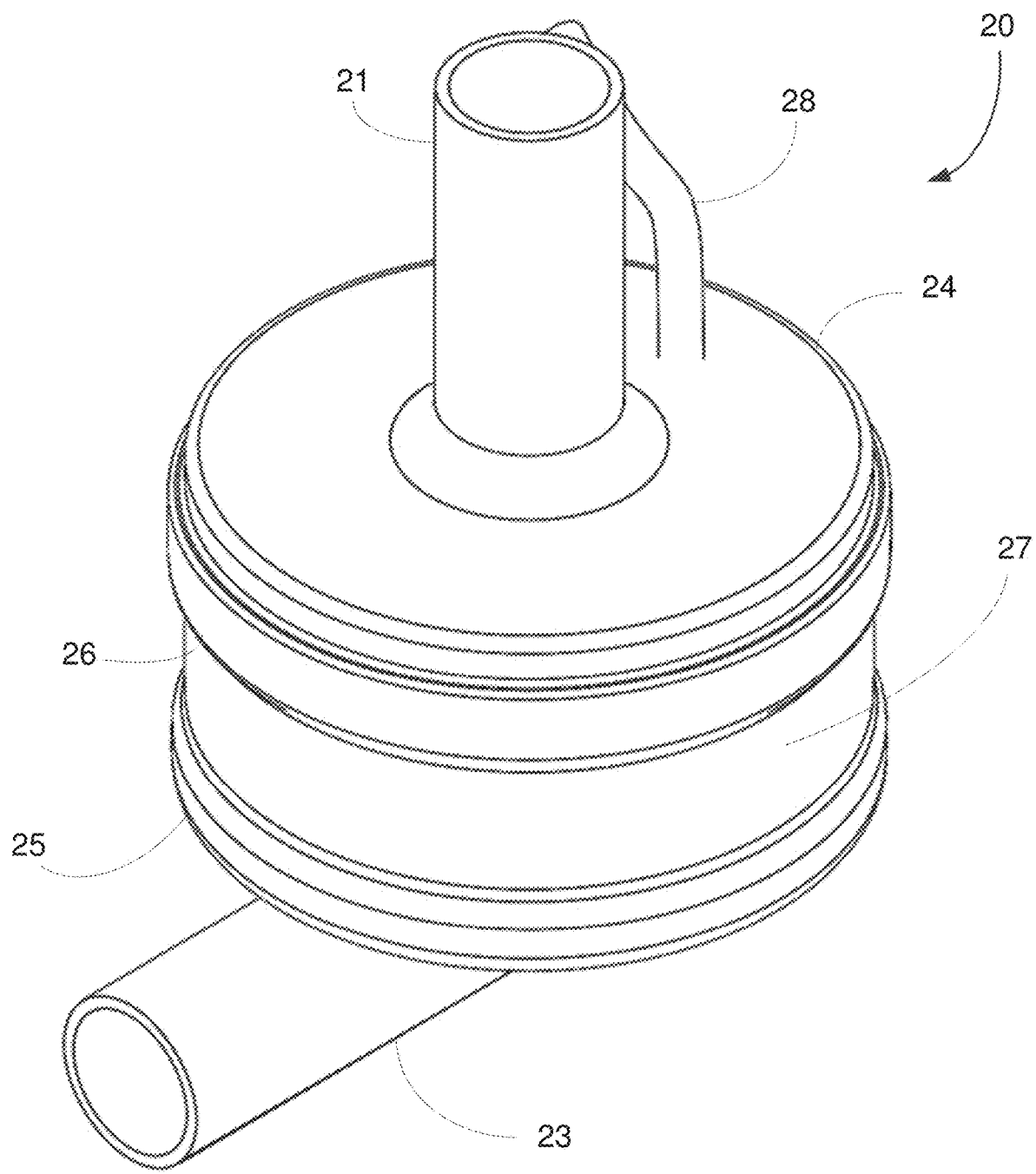
FIG. 2 is a perspective view of the implantable pump of FIG. 1.

Referring now also to FIG. 2, implantable pump 20 in a preferred embodiment consists of upper housing portion 24 joined to lower housing portion 25 along interface 26, for example, by threads or welding, to form fluid tight pump housing 27 that may have a cylindrical shape. Upper housing portion 24 includes inlet cannula 21 and electrical conduit 28 for receiving electrical wires from controller 30 and battery 40. Lower housing portion 25 includes outlet 23 that couples to outlet cannula 22, as shown in FIG. 1. Pump housing 27 is made of a biocompatible material, such as stainless steel or titanium, and is sized to be implanted within a patient's chest.

Referring again to FIG. 1, in one embodiment, controller 30 and battery 40 are extracorporeal, and are sized so as to be placed on a belt or garment worn by the patient. Both controller 30 and battery 40 are electrically coupled to implantable pump 20, for example, via cable 29 that extends through a percutaneous opening in the patient's skin and into electrical conduit 28 of pump housing 27. Illustratively, battery 40 is electrically coupled to controller 30 via cable 41 that is integrated into belt 42. In an alternative embodiment, controller 30 may be enclosed within a biocompatible housing and sized to be implanted subcutaneously in the patient's abdomen. In this alternative embodiment, controller 30 may include a wireless transceiver for bi-directional communications with an extracorporeal programming device and also includes a battery that is continuously and inductively charged via extracorporeal battery 40 and an extracorporeal charging circuit. As will be understood, the foregoing alternative embodiment avoids the use of percutaneous cable 29, and thus eliminates a frequent source of infection for conventional LVAD devices.

Battery 40 preferably comprises a rechargeable battery capable of powering implantable pump 20 and controller 30 for a period of several hours, e.g., 4-12 hours, before needing to be recharged. Battery 40 may include a separate charging circuit, not shown, as is conventional for rechargeable batteries. Battery 40 preferably is disposed within a housing suitable for carrying on a belt or holster, so as not to interfere with the patient's daily activities.

Programmer 50 may consist of a conventional laptop computer that is programmed to execute programmed software routines, for use by a clinician or medical professional, for configuring and providing operational parameters to controller 30. The configuration and operational parameter data are stored in a memory associated with controller 30 and used by the controller to control operation of implantable pump 20. As described in further detail below, controller 30 directs implantable pump 20 to operate at specific parameters determined by programmer 50. Programmer 50 preferably is coupled to controller 30 via cable 51 only when the operational parameters of the implantable pump are initially set or periodically adjusted. e.g., when the patient visits the clinician.

In accordance with another aspect of the invention, mobile device 60, which may a conventional smartphone, may include an application program for bi-directionally and wirelessly communicating with controller 30, e.g., via WiFi or Bluetooth communications. The application program on mobile device 60 may be programmed to permit the patient to send instructions to controller to modify or adjust a limited number of operational parameters of implantable pump 20 stored in controller 30. Alternatively or in addition, mobile device 60 may be programmed to receive from controller 30 and to display on screen 61 of mobile device 60, data relating to operation of implantable pump 20 or alert or status messages generated by controller 30.

Figure 3A:
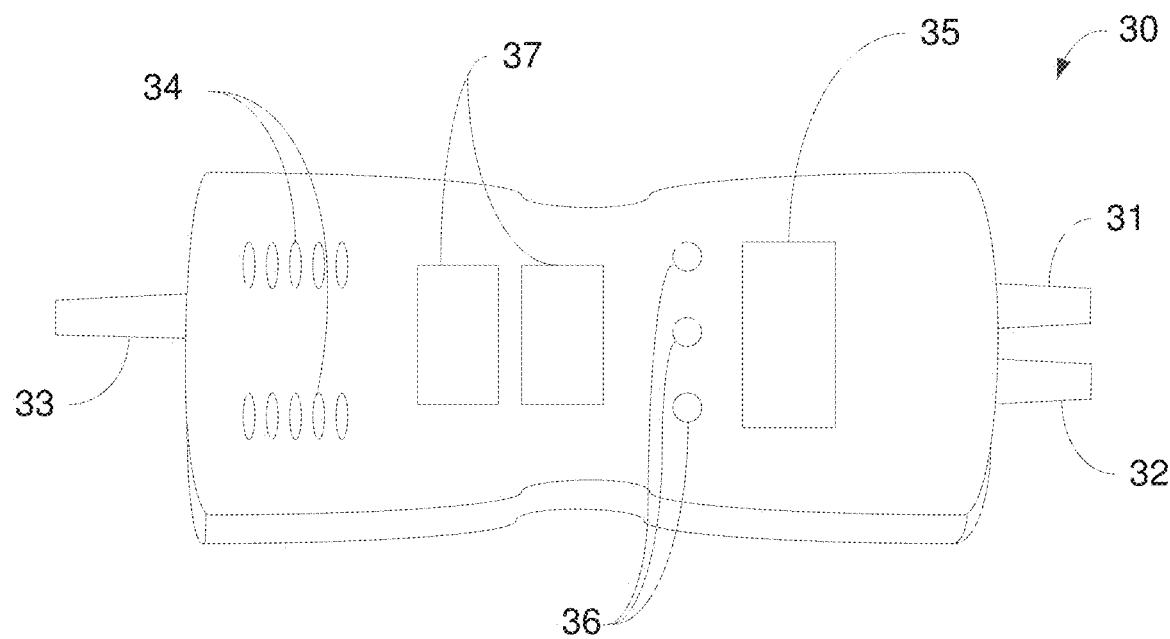
FIGS. 3A and 3B are, respectively, a perspective view and a schematic view of the electronic components of an exemplary embodiment of the controller of the present invention.
Figure 3B:
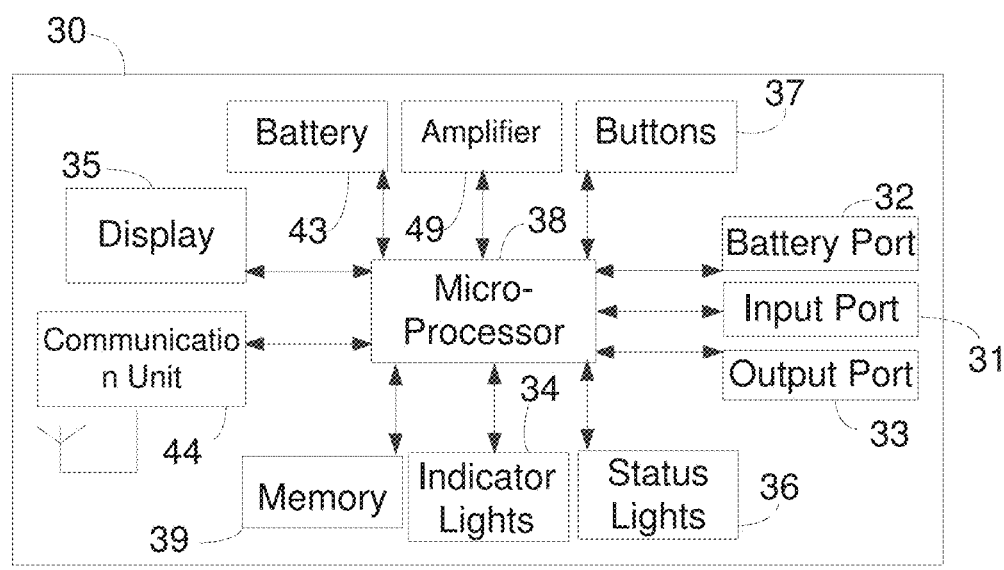

With respect to FIGS. 3A and 3B, controller 30 is described in greater detail. As depicted in FIG. 1, controller 30 may be sized and configured to be worn on the exterior of the patient's body and may be incorporated into a garment such as a belt or a vest. Controller 30 includes input port 31, battery port 32, output port 33, indicator lights 34, display 35, status lights 36 and buttons 37.

Input port 31 is configured to periodically and removably accept cable 51 to establish an electrical connection between programmer 50 and controller 30, e.g., via a USB connection. In this manner, a clinician may couple to controller 30 to set or adjust operational parameters stored in controller 30 for controlling operation of implantable pump. In addition, when programmer 50 is coupled to controller 30, the clinician also may download from controller 30 data relating to operation of the implantable pump, such as actuation statistics, for processing and presentation on display 55 of programmer 50, illustrated in FIG. 5A. Alternatively, or in addition, controller 30 may include a wireless transceiver for wirelessly communicating such information with programmer 50. In this alternative embodiment, wireless communications between controller 30 and programmer 50 may be encrypted with an encryption key associated with a unique identification number of the controller, such as a serial number.

Battery port 32 is configured to removably accept cable 41, illustratively shown in FIG. 1 as integrated with belt 42, so that cable 41 routed through the belt and extends around the patient's back until it couples to controller 30. In this manner, battery 40 may be removed from belt 42 and disconnected from controller 30 to enable the patient to periodically replace the battery with a fully charged battery. It is expected that the patient will have available to him or her at least two batteries, so that while one battery is coupled to controller 30 to energize the controller and implantable pump, the other battery may be connected to a recharging station. Alternatively, or in addition, battery port 32 may be configured to accept a cable that is coupled directly to a power supply, such a substantially larger battery/charger combination that permits the patient to remove battery 40 while lying supine in a bed, e.g., to sleep.

Output port 33 is electrically coupled to cable 29, which in turn is coupled to implantable pump 20 through electrical conduit 28 of pump housing 27. Cable 29 provides both energy to energize implantable pump 20 in accordance with the configuration settings and operational parameters stored in controller 30, and to receive data from sensors disposed in implantable pump 20. In one embodiment, cable 29 may comprise an electrical cable having a biocompatible coating and is designed to extend percutaneously. Cable 29 may be impregnated with pharmaceuticals to reduce the risk of infection, the transmission of potentially hazardous substances or to promote healing where it extends through the patient's skin and tissue.

As mentioned above, controller 30 may include indicator lights 34, display 35, status lights 36 and buttons 37. Indicator lights 34 may visually display information relevant to operation of the system, such as the remaining life of battery 40. Display 35 may be a digital liquid crystal display that displays real time pump performance data, physiological data of the patient, such as heart rate, or operational parameters of the implantable pump, such as the target pump pressure or flow rate, etc. When it is determined that certain parameter conditions exceed preprogrammed thresholds, an alarm may be sounded, an alert may be displayed on display 35 and/or an internal vibrating element may vibrate controller 30 to provide tactile stimulation. Status lights 36 may comprise light emitting diodes (LEDs) that are turned on or off to indicate whether certain functionality of the controller or implantable pump is active. Buttons 37 may be used to wake up display 35, to set or quiet alarms, etc.

With respect to FIG. 3B, the components of the illustrative embodiment of controller 30 of FIG. 3A are described. In addition to the components of controller 30 described in connection with FIG. 3A, controller 30 further includes microprocessor 38, memory 39, battery 43, optional transceiver 44 and amplifier circuitry 45. Microprocessor may be a general purpose microprocessor, for which programming to control operation of implantable pump 20 is stored in memory 39. Memory 39 also may store configuration settings and operational parameters for implantable pump 20. Battery 43 supplies power to controller 30 to provide continuity of operation when battery 40 is periodically swapped out. Optional transceiver 44 (e.g., communication unit) facilitates wireless communication with programmer 50 and/or mobile device 60 via any of a number of well-known communications standards, including BLUETOOTH™, ZigBee, and/or any IEEE 802.11 wireless standard such as Wi-Fi or Wi-Fi Direct. Controller 30 further may include amplifier circuitry 49 for amplifying electrical signals transferred between controller 30 and implantable pump 20.

Figure 4:
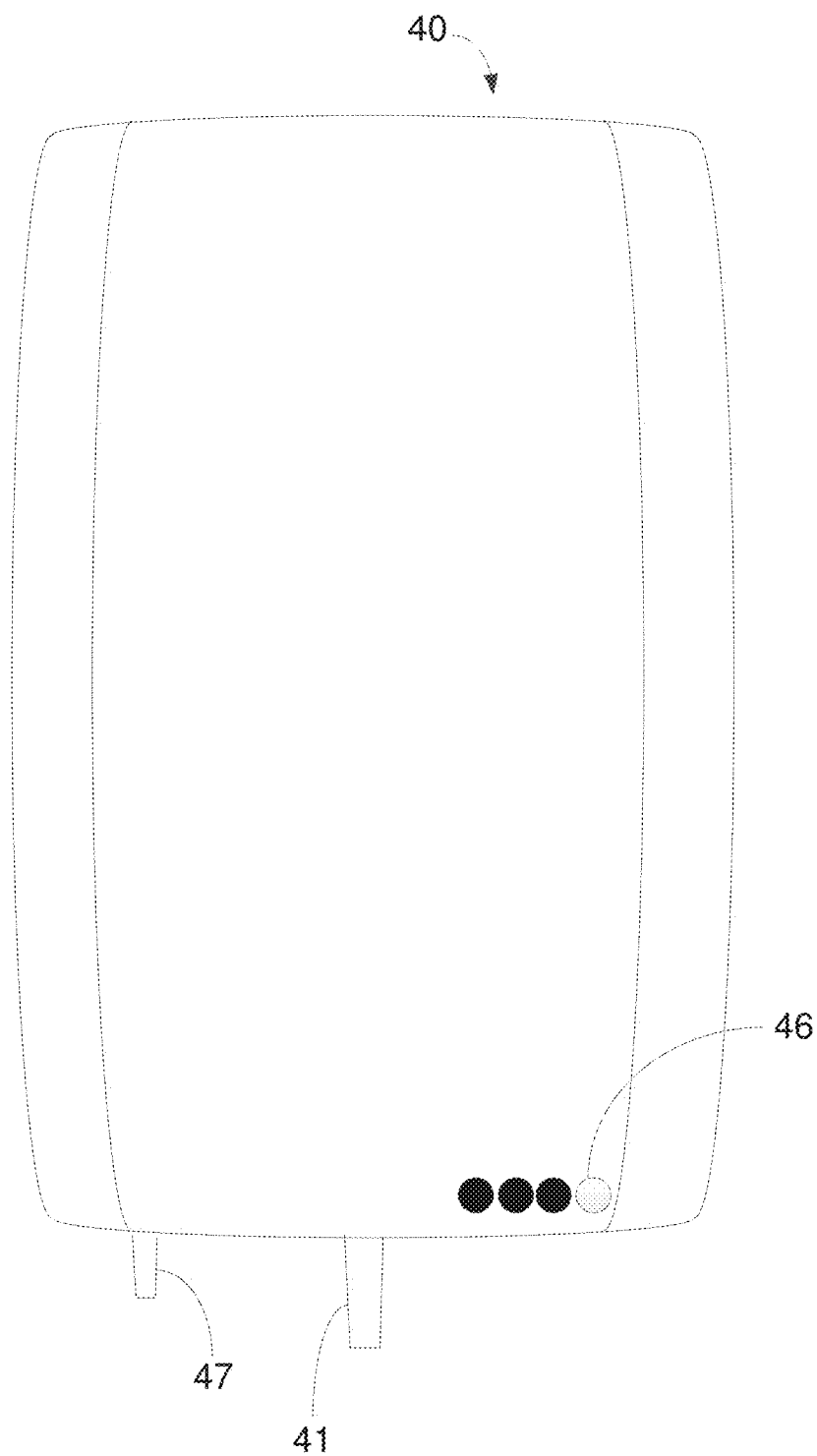
FIG. 4 is a plan view of an extracorporeal battery for use in the pump system of the present invention.

Referring now to FIG. 4, battery 40 is described. Battery 40 provides power to implantable pump 20 and also may provide power to controller 30. Battery 40 may consist of a single battery or a plurality of batteries disposed within a housing, and preferably is sized and configured to be worn on the exterior of the patient's body, such as on belt 42. Battery life indicator 46 may be provided on the exterior of battery 40 to indicate the amount of the remaining charge of the battery. Cable 41 may have one end removably coupled to battery 40 and the other end removably coupled to battery port 32 of controller 30 to supply power to energize implantable pump 20. In one embodiment, battery 40 may be rechargeable using a separate charging station, as is known in the art of rechargeable batteries. Alternatively, or in addition, battery 40 may include port 47 which may be removably coupled to a transformer and cable to permit the battery to be recharged using a conventional residential power outlet, e.g., 120 V, 60 Hz AC power.

Figure 5A:
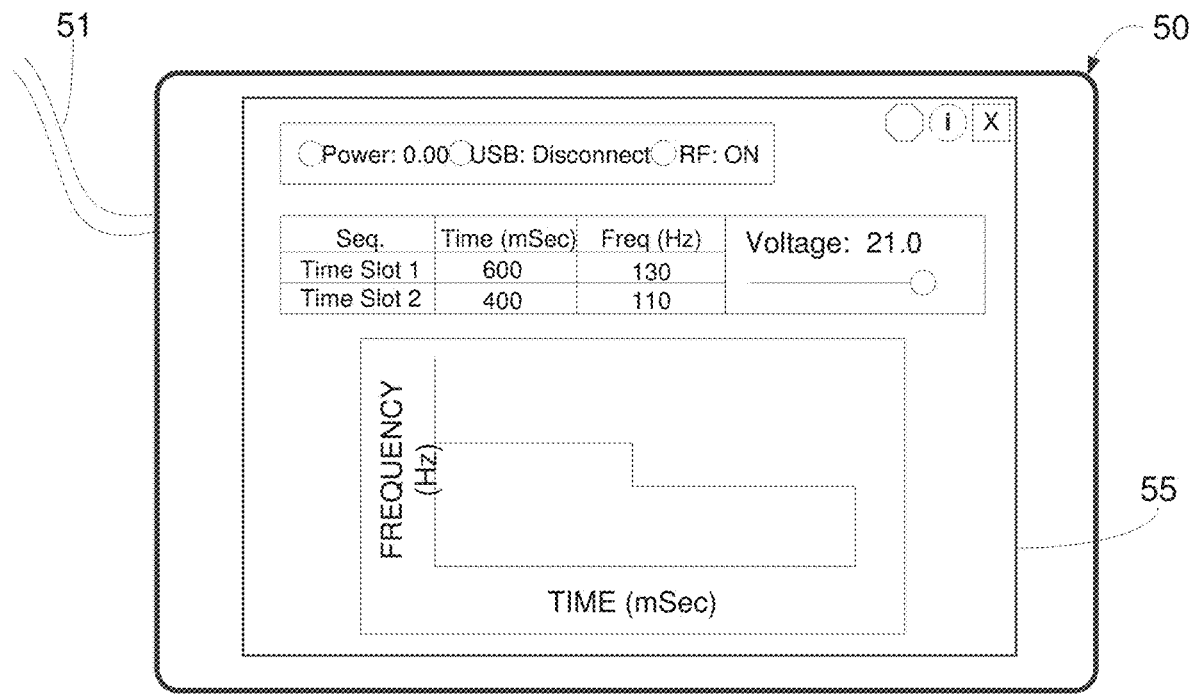
FIGS. 5A and 5B are, respectively, a perspective view and a schematic view of the electronic components of an exemplary embodiment of the programmer of the present invention.
Figure 5B:
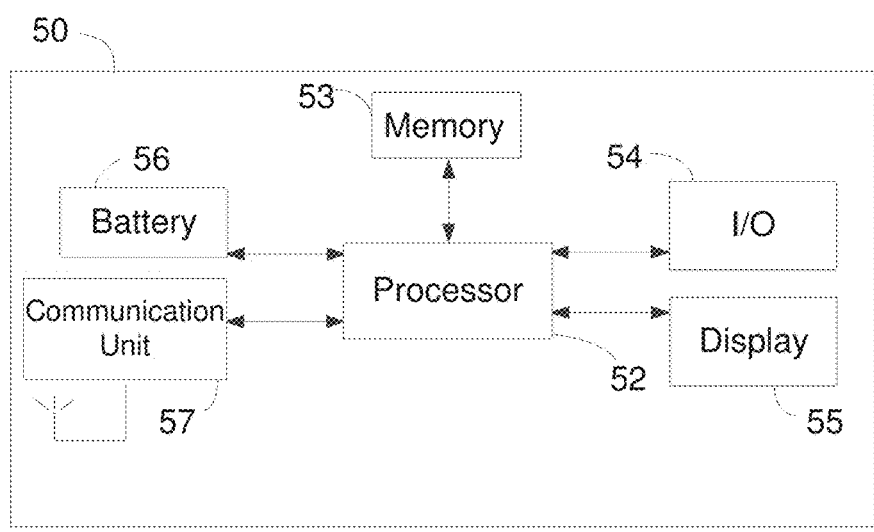

Referring now to FIGS. 5A-5B, programmer 50 is described. Programmer 50 may be a conventional laptop or tablet computer loaded with programmed software routines for configuring controller 30 and setting operational parameters that controller 30 uses to control operation of implantable pump 20. As discussed above, programmer 50 typically is located in a clinician's office or hospital, and is coupled to controller 30 via cable 51 or wirelessly to initially set up controller 30, and then periodically thereafter as required to adjust the operational parameters as may be needed. The operation parameters of controller 30 set using the programmed routines of programmer 50 may include but are not limited to pump operating mode, applied voltage, pump frequency, pump amplitude, target flow rate, pulsatility, etc. When first implanted, the surgeon or clinician may use programmer 50 to communicate initial operating parameters to controller 30. Following implantation, the patient periodically may return to the clinician's office for adjustments to the operational parameters which may again be made using programmer 50.

Programmer 50 may be any type of conventional personal computer device such as a laptop or a tablet computer having touch screen capability. As illustrated in FIG. 5B, programmer 50 preferably includes processor 52, memory 53, input/output device 54, display 55, battery 56 and communication unit 57. Memory 53 may include the operating system for the programmer, as well as the programmed routines needed to communicate with controller 30. Communication unit 57 may include any of a number of well-known communication protocols, such as BLUETOOTH™, ZigBee, and/or any IEEE 802.11 wireless standard such as Wi-Fi or Wi-Fi Direct. As illustrated in FIG. 5A, the programmed routines used to program and communicate with controller 30 also may provide data for display on the screen of programmer 50 identifying operational parameters with which controller 30 controls implantable pump 20. The programmed routines also may enable programmer 50 to download from controller 30 operational data or physiologic data communicated by the implantable pump and to display that information in real time while the programmer is coupled to the controller via a wired or wireless connection. The transferred data may then be processed and displayed on the screen of programmer 50.

Figure 6:
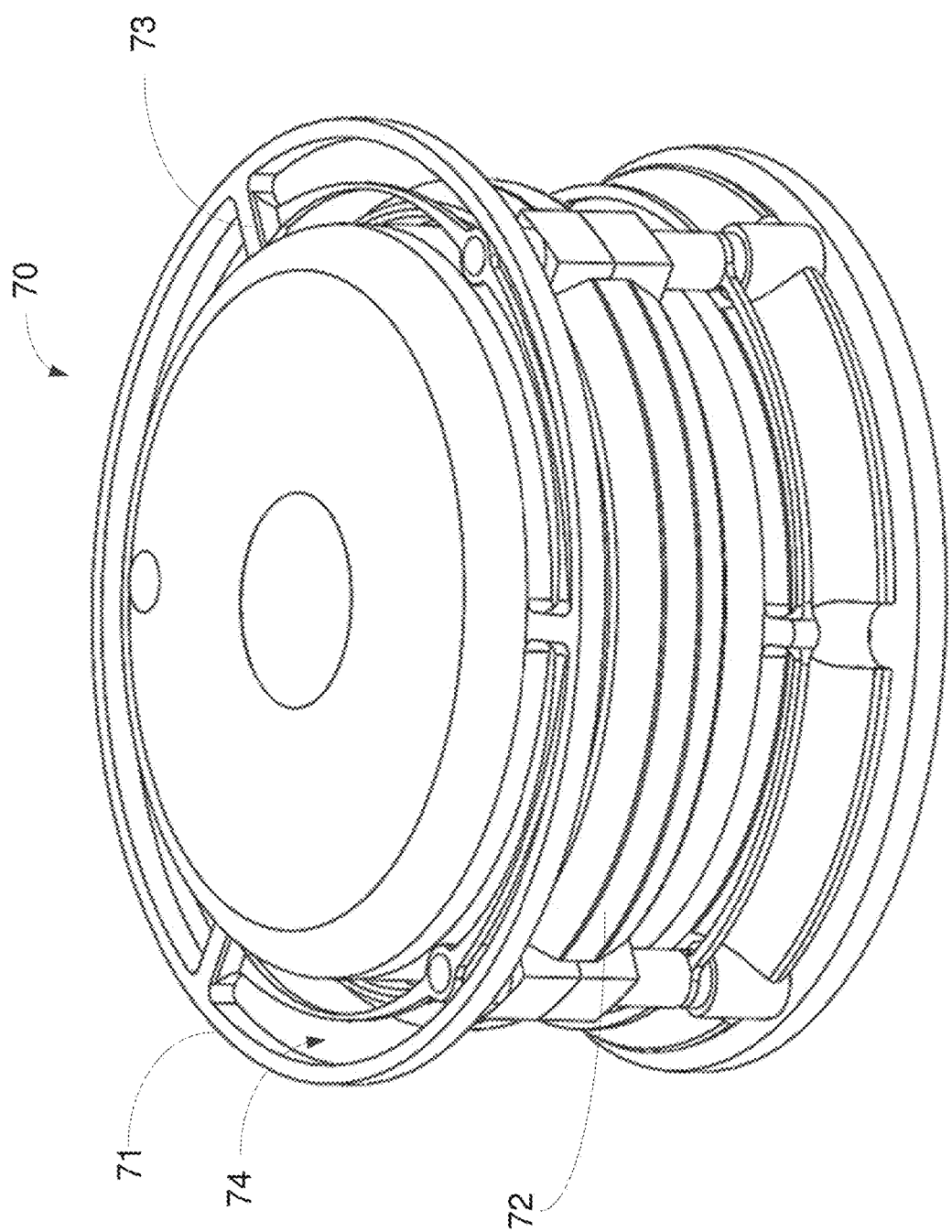
FIG. 6 is a perspective view of the pump assembly of the present invention.
Figure 7:
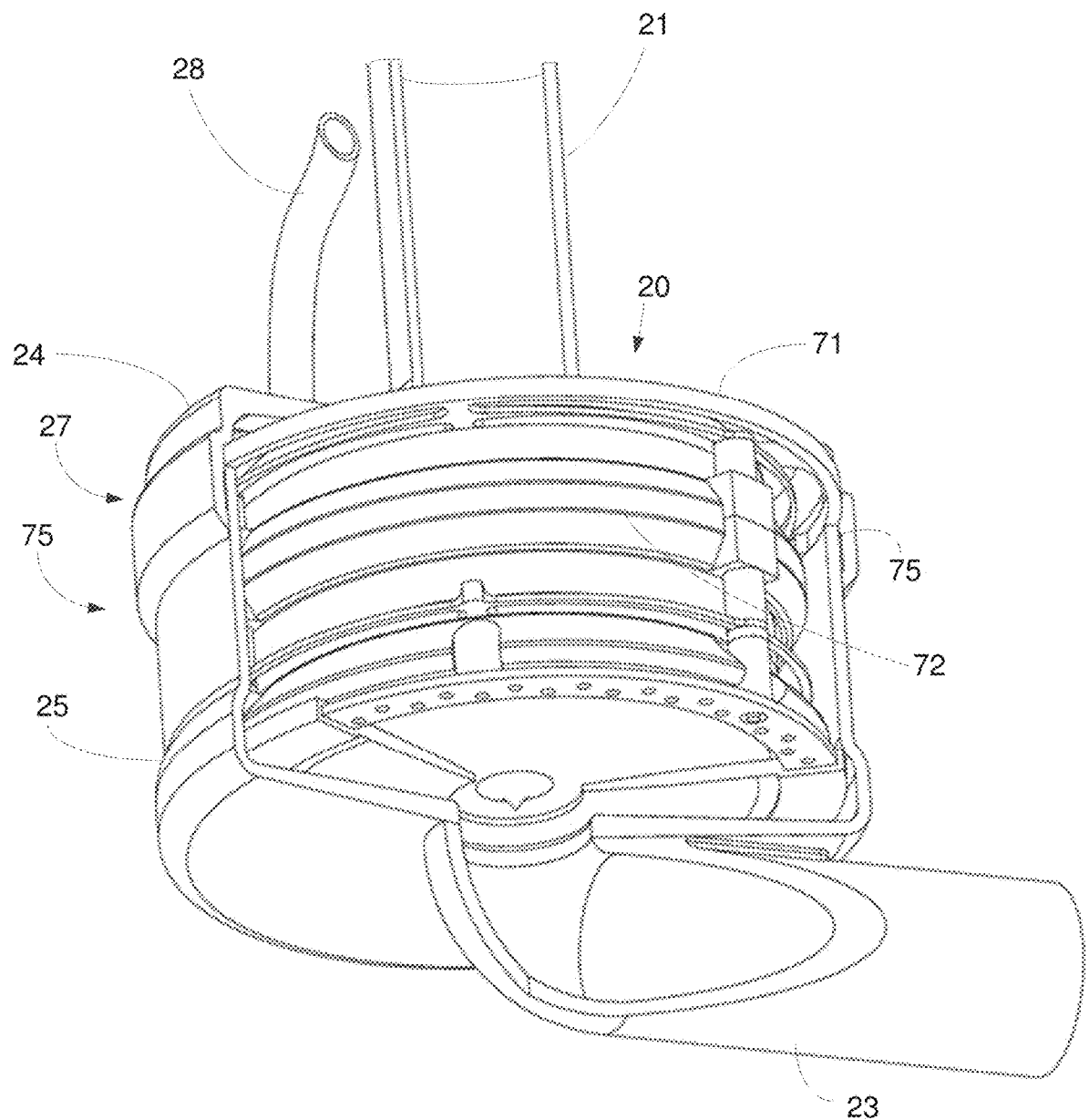
FIG. 7 is a perspective, cut-away view of the implantable pump of the present invention.

Referring now to FIGS. 6 and 7, a preferred embodiment of pump assembly 70 and implantable pump 20 are illustrated. However, it is understood that pump assemblies and implantable pumps, and components included therein, may have different shapes and sizes than those illustrated in FIGS. 6 and 7 without departing from the invention described herein. As is illustrated in FIG. 7, pump assembly 70 is configured to fit within pump housing 27. To fix pump assembly 70 within pump housing 27, pump assembly 70 may include fixation ring 71, which may extend from and around stator assembly 72, and may be captured between upper housing portion 24 and lower housing portion 25 when the housing portions are assembled, as illustrated in FIG. 7. In this manner, stator assembly 72 may be suspended within the pump housing in close-fitting relation to the interior walls of the pump housing. Fixation ring 71 preferably is a rigid annular structure that is disposed concentrically around stator assembly 72, having a larger diameter than stator assembly 72. Fixation ring 71 may be rigidly coupled to stator assembly 72 via struts 73. Struts 73 may create gap 74 between fixation ring 71 and stator assembly 72, which preferably is about 0.05 mm at its most restricted point.

As shown in FIG. 7, pump assembly 70 may be disposed in pump housing 27 such that fixation ring 71 is captured on step 75 formed between upper housing portion 24 and lower housing portion 25. In this manner, stator assembly 72 may be suspended within, and prevented from moving within, pump housing 27. Pump housing 27 preferably is sized and configured to conform to pump assembly 70 such that, stator assembly 72 does not contact the interior of the pump housing at any location other than at fixation ring 71.

Figure 8:
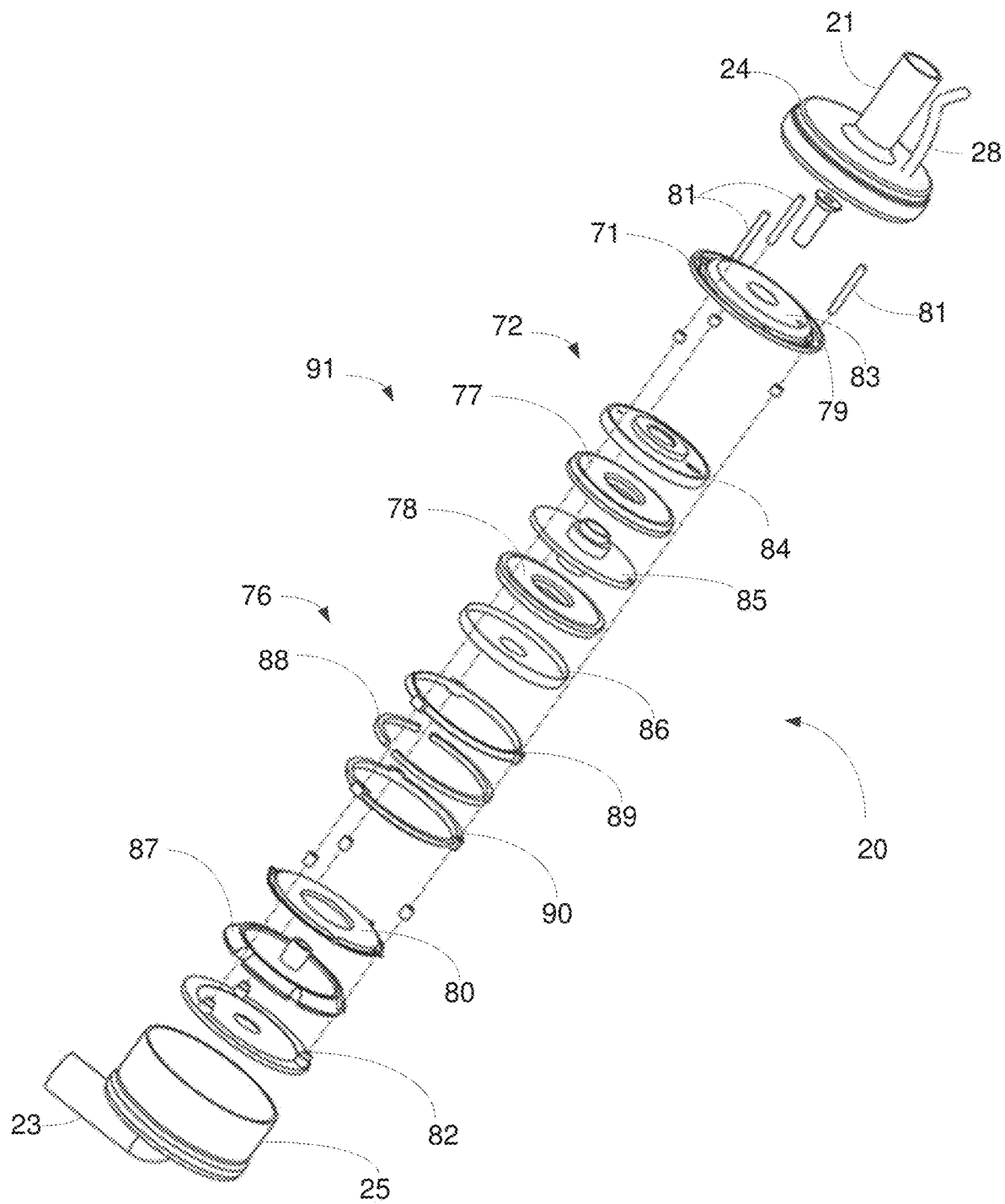
FIG. 8 is an exploded view of the implantable pump of the present invention.

FIG. 8 is an exploded view of implantable pump 20, depicting the arrangement of the internal components of pump assembly 70 arranged between upper housing portion 24 and lower housing portion 25. In particular, pump assembly 70 may comprise stator assembly 72, magnetic ring assembly 76, first electromagnetic coil 77, second electromagnetic coil 78, fixation ring 71, first suspension ring 79, second suspension ring 80, posts 81 and membrane assembly 82. Stator assembly 72 may comprise tapered section 83, electromagnetic coil holder portions 84, 85 and 86, and flanged portion 87. Magnetic ring assembly 76 may comprise magnetic ring 88 and magnetic ring holder portions 89 and 90. First and second electromagnetic coils 77 and 78, together with electromagnetic coil holder portions 84, 85 and 86 may form electromagnet assembly 91. Electromagnet assembly 91 together with stator assembly 72 form an actuator assembly. The actuator assembly together with magnetic ring assembly 76 in turn forms the actuator system of implantable pump 20.

First electromagnetic coil 77 and second electromagnetic coil 78 may be concentrically sandwiched between electromagnetic coil holder portions 84, 85 and 86 to form electromagnet assembly 91. Tapered section 83, which may be coupled to fixation ring 71 and first suspension spring 79, may be located concentrically atop electromagnet assembly 91. Magnetic ring 88 may be disposed with magnetic ring holder portions 89 and 90 to form magnetic ring assembly 76, which may be concentrically disposed for reciprocation over electromagnet assembly 91. Second suspension ring 80 may be disposed concentrically beneath electromagnet assembly 91. Flanged portion 87 may be concentrically disposed below second suspension ring 80. Posts 81 may engage first suspension ring 79, magnetic ring assembly 76 and second suspension ring 80 at equally spaced locations around the actuator assembly. Membrane assembly 82 may be positioned concentrically below flanged portion 87 and engaged with posts 81.

Figure 9:
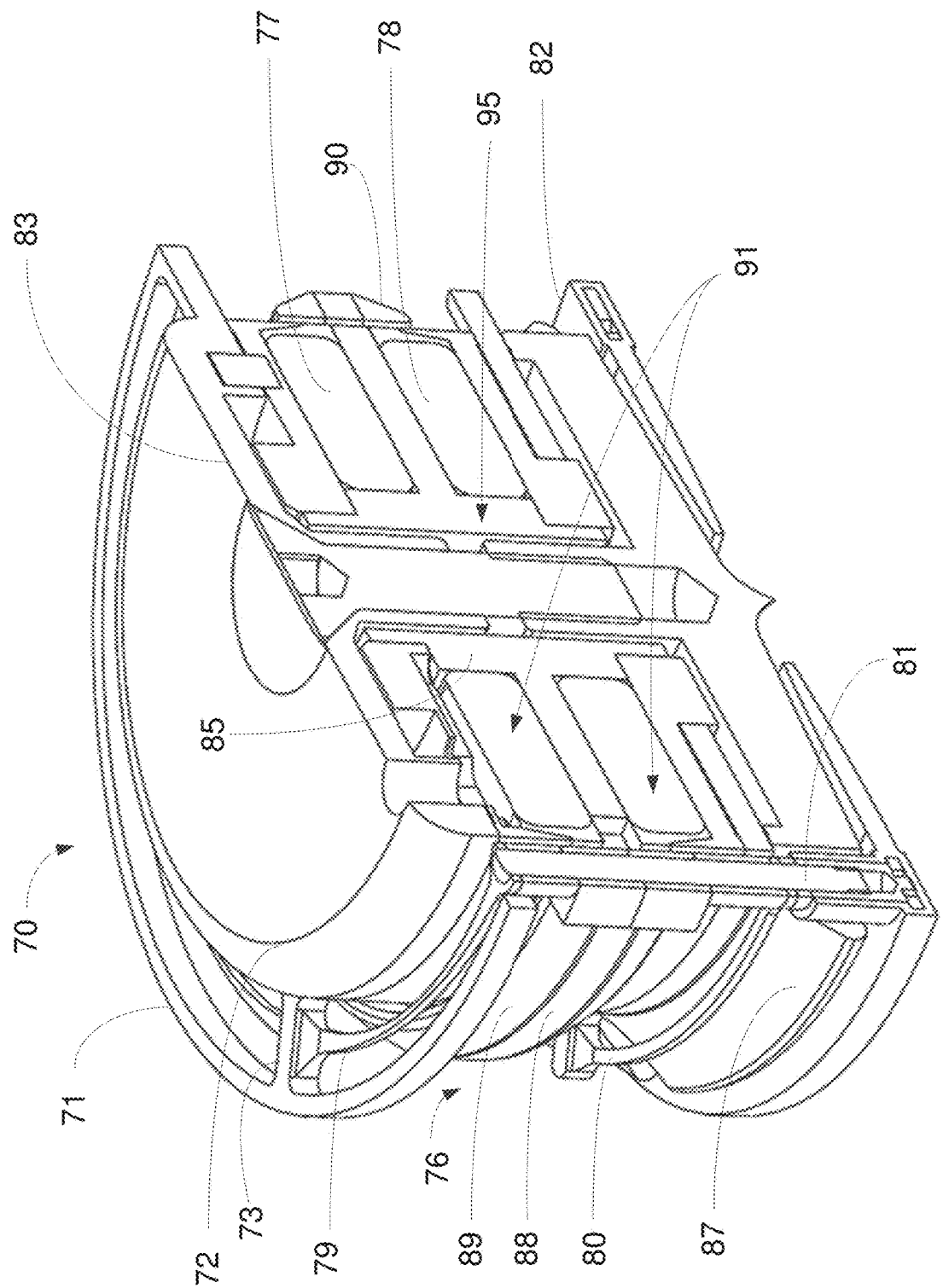
FIG. 9 is a perspective cross-sectional view of the pump assembly of the present invention.

Further details of pump assembly 70 are provided with respect to FIG. 9. Specifically, actuator assembly 95 comprises stator assembly 72 and electromagnet assembly 91, including first and second electromagnetic coils 77 and 78. During use of implantable pump 20, actuator assembly 95 remains stationary relative to pump housing 27. First electromagnetic coil 77 and second electromagnetic coil 78 may be separated by electromagnetic holder portion 85. Controller 30 and battery 40 are electrically coupled to electromagnetic coils 77 and 78 via cable 29 that extends through electrical conduit 28 of pump housing 27 to supply current to electromagnetic coils 77 and 78. First electromagnetic coil 77 and second electromagnetic coil 78 may be in electrical communication with one another or may be configured to operate independently and have separate wired connections to controller 30 and battery 40 via cable 29.

Electromagnetic coils 77 and 78 may be made of any electrically conductive metallic material such as copper and further may comprise of one or more smaller metallic wires wound into a coil. The wires of the electromagnetic coils are insulated to prevent shorting to adjacent conductive material. Other components of pump assembly 70, such as stator assembly 72, preferably also are insulated and/or made of non-conductive material to reduce unwanted transmission of the electrical signal.

Actuator assembly 95 may be surrounded by first suspension ring 79 and second suspension ring 80. Suspension rings 79 and 80 may be annular in shape and fit concentrically around actuator assembly 95. First suspension ring 79 preferably is rigidly affixed to tapered section 83 near a top portion of stator assembly 72 via struts 73 extending from the suspension ring to the stator assembly. As discussed above, struts 73 may also affix fixation ring 71 to stator assembly 72. Fixation ring 71 and first suspension spring 79 may be sized and positioned such that a gap of no less than 0.5 mm exists between first suspension ring 79 and fixation ring 71. Second suspension ring 80 similarly may be rigidly affixed via struts near the bottom of stator assembly 72, below electromagnet assembly 91. Suspension rings 79 and 80 preferably are sized and shaped such that when suspension rings 79 and 80 are positioned surrounding actuator assembly 95, a gap of no less than 0.5 mm exists between actuator assembly 95 and suspension rings 79 and 80.

First suspension ring 79 and second suspension ring 80 may comprise stainless steel, titanium, or cobalt chromium alloys having elastic properties and which exhibits a spring force when deflected in a direction normal to the plane of the spring. First suspension ring 79 and second suspension ring 80 may be substantially rigid with respect to forces applied tangential to the suspension ring. In this manner, first suspension ring 79 and second suspension ring 80 may exhibit a spring tension when deformed up and down relative to a vertical axis of the actuator assembly but may rigidly resist movement along any other axis, e.g., tilt or twist movements.

Magnetic ring assembly 76 may be annular in shape and concentrically surrounds actuator assembly 95. Magnetic ring 88 may comprise one or more materials exhibiting magnetic properties such as iron, nickel, cobalt or various alloys. Magnetic ring 88 may be made of a single unitary component or comprise several magnetic components that are coupled together. Magnetic ring assembly 76 may be sized and shaped such that when it is positioned concentrically over actuator assembly 95, a gap of no less than 0.5 mm exists between an outer lateral surface of actuator assembly 95 and an interior surface of magnetic ring assembly 76.

Magnetic ring assembly 76 may be concentrically positioned around actuator assembly 95 between first suspension ring 79 and second suspension ring 80, and may be rigidly coupled to first suspension ring 79 and second suspension ring 80. Magnetic ring assembly 76 may be rigidly coupled to the suspension rings by more than one post 81 spaced evenly around actuator assembly 95 and configured to extend parallel to a central axis of pump assembly 70. Suspension rings 79 and 80 and magnetic ring assembly 76 may be engaged such that magnetic ring assembly 76 is suspended equidistant between first electromagnetic coil 77 and second electromagnetic coil 78 when the suspension rings are in their non-deflected shapes. Each of suspension rings 79 and 80 and magnetic ring holder portions 89 and 90 may include post receiving regions for engaging with posts 81 or may be affixed to posts 81 in any suitable manner that causes suspension rings 79 and 80 and magnetic ring assembly 76 to be rigidly affixed to posts 81. Posts 81 may extend beyond suspension rings 79 and 80 to engage other components, such as flanged portion 87 and membrane assembly 82.

First electromagnetic coil 77 may be activated by controller applying an electrical signal from battery 40 to first electromagnetic coil 77, thus inducing current in the electromagnetic coil and generating a magnetic field surrounding electromagnetic coil 77. The direction of the current in electromagnetic coil 77 and the polarity of magnetic ring assembly 76 nearest electromagnetic coil 77 may be configured such that the first electromagnetic coil magnetically attracts or repeals magnetic ring assembly 76 as desired. Similarly, a magnetic field may be created in second electromagnetic coil 78 by introducing a current in the second electromagnetic coil. The direction of the current in second electromagnetic coil 78 and the polarity of magnetic ring assembly 76 nearest the second electromagnetic coil also may be similarly configured so that first electromagnetic coil 77 magnetically attracts or repels magnetic ring assembly 76 when an appropriate current is induced in second electromagnetic coil 78.

Because magnetic ring assembly 76 may be rigidly affixed to posts 81, which in turn may be rigidly affixed to first suspension ring 79 and second suspension ring 80, the elastic properties of the suspension rings permit magnetic ring assembly 76 to move up towards first electromagnetic coil 77 or downward toward second electromagnetic coil 78, depending upon the polarity of magnetic fields generated by the electromagnetic rings. In this manner, when magnetic ring assembly 76 experiences an upward magnetic force, magnetic ring assembly 76 deflects upward towards first electromagnetic coil 77. As posts 81 move upward with magnetic ring assembly 76, posts 81 cause the suspensions rings 79 and 80 to elastically deform, which creates a spring force opposite to the direction of movement. When the magnetic field generated by the first electromagnetic coil collapses, when the electrical current ceases, this downward spring force causes the magnetic ring assembly to return to its neutral position. Similarly, when magnetic ring assembly 76 is magnetically attracted downward, magnetic ring assembly 76 deflects downward towards second electromagnetic ring 78. As posts 81 move downward with magnetic ring assembly 76, posts 81 impose an elastic deformation of the first and second suspension rings, thus generating a spring force in the opposite direction. When the magnetic field generated by the second electromagnetic ring collapses, when the electrical current ceases, this upward spring force causes the magnetic ring assembly to again return to its neutral position.

Electromagnetic coils 77 and 78 may be energized separately, or alternatively, may be connected in series to cause the electromagnetic coils to be activated simultaneously. In this configuration, first magnetic coil may be configured to experience a current flow direction opposite that of the second electromagnetic coil. Accordingly, when current is induced to first electromagnetic coil 77 to attract magnetic ring assembly 76, the same current is applied to second electromagnetic coil 78 to induce a current that causes second electromagnetic coil 78 to repel magnetic ring assembly 76. Similarly, when current is induced to second electromagnetic coil 78 to attract magnetic ring assembly 76, the current applied to first electromagnetic coil 77 causes the first electromagnetic coil to repel magnetic ring assembly 76. In this manner, electromagnetic coils 77 and 78 work together to cause deflection of magnetic ring assembly 76.

By manipulating the timing and intensity of the electrical signals applied to the electromagnetic coils, the frequency at which magnetic ring assembly 76 deflects towards the first and second electromagnetic coils may be altered. For example, by alternating the current induced in the electromagnetic coils more frequently, the magnetic ring assembly may be caused to cycle up and down more times in a given period. By increasing the amount of current, the magnetic ring assembly may be deflected at a faster rate and caused to travel longer distances.

Alternatively, first electromagnetic coil 77 and second electromagnetic coil 78 may be energized independently. For example, first electromagnetic coil 77 and second electromagnetic coil 78 may be energized at varying intensities; one may be coordinated to decrease intensity as the other increases intensity. In this manner, intensity of the signal applied to second electromagnetic coil 78 to cause downward magnetic attraction may simultaneously be increased as the intensity of the signal applied to first electromagnetic coil 77 causes an upward magnetic attraction that decreases.

In accordance with one aspect of the invention, movements of magnetic ring assembly 76 may be translated to membrane assembly 82 which may be disposed concentrically below stator assembly 72. Membrane assembly 82 preferably is rigidly attached to magnetic ring assembly 76 by posts 81. In the embodiment depicted in FIG. 9, posts 81 may extend beyond second suspension ring 80 and coupled to membrane assembly 82.

Figure 10:
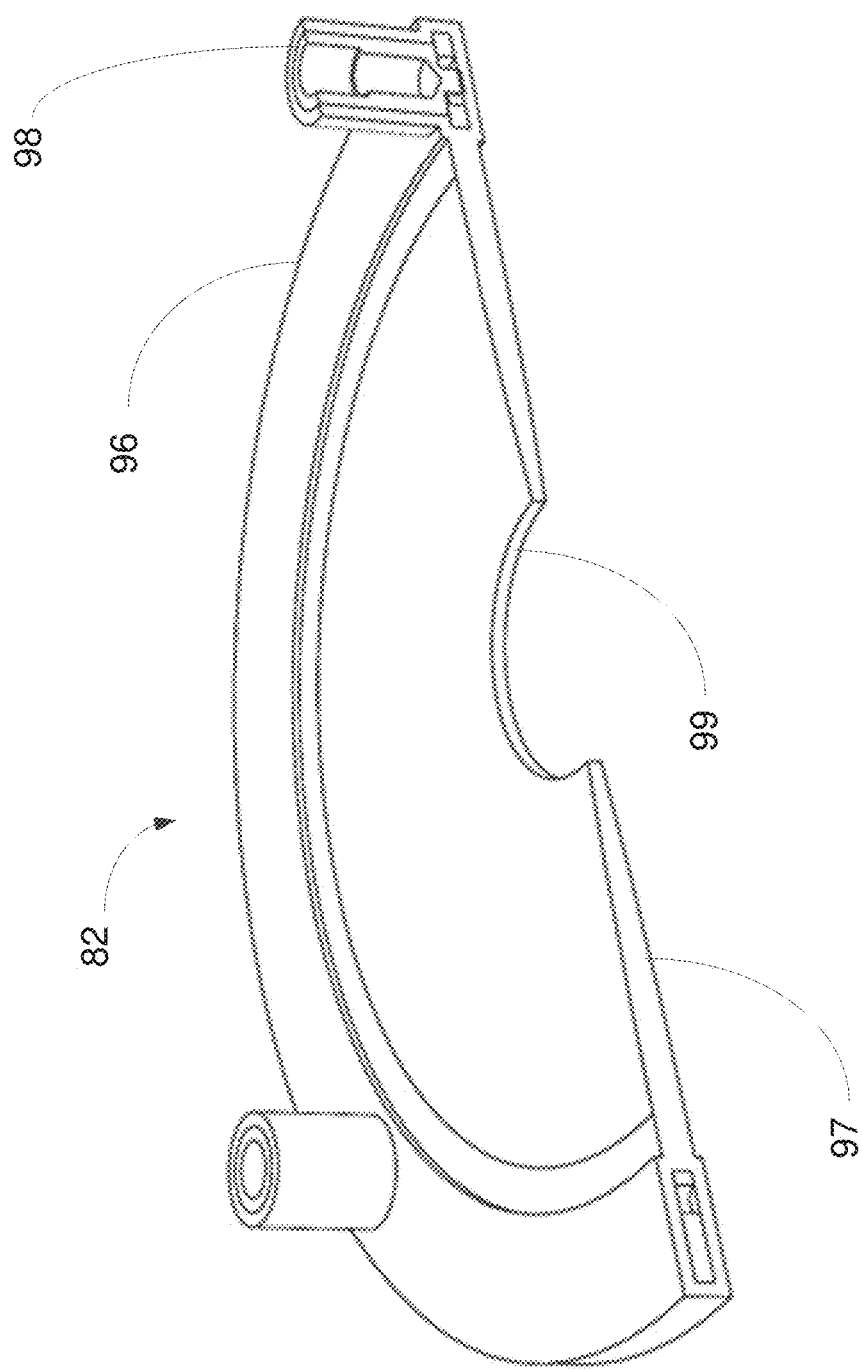
FIG. 10 is a perspective cross-sectional view of the membrane assembly of the present invention.

Referring now to FIG. 10, one embodiment of membrane assembly 82 is described in greater detail. Membrane assembly 82 may comprise rigid membrane ring 96 and membrane 97. Rigid membrane ring 96 exhibits rigid properties under typical forces experienced during the full range of operation of the present invention. Post reception sites 98 may be formed into rigid membrane ring 96 to engage membrane assembly 82 with posts 81. Alternatively, posts 81 may be attached to rigid membrane ring 96 in any other way which directly translates the motion of magnetic ring assembly 76 to rigid membrane ring 96. Rigid membrane ring 96 may be affixed to membrane 97 and hold the membrane in tension. Membrane 97 may be molded directly onto rigid membrane ring 96 or may be affixed to rigid membrane ring 96 in any way that holds membrane 97 uniformly in tension along its circumference. Membrane 97 alternatively may include a flexible pleated structure where it attaches to rigid membrane ring 96 to increase the ability of the membrane to move where the membrane is affixed to rigid membrane ring 96. Membrane 97 may further include circular aperture 99 disposed in the center of the membrane.

In a preferred embodiment, membrane 97 has a thin, planar shape and is made of an elastomer having elastic properties and good durability. Alternatively, membrane 97 may have a uniform thickness from the membrane ring to the circular aperture. As a yet further alternative, membrane 97 may vary in thickness and exhibit more complex geometries. For example, as shown in FIG. 10, membrane 97 may have a reduced thickness as the membrane extends from rigid membrane ring 96 to circular aperture 99. Alternatively, or in addition to, membrane 97 may incorporate metallic elements such as a spiral spring to enhance the spring force of the membrane in a direction normal to plane of the membrane, and this spring force may vary radially along the membrane. In yet another embodiment, membrane 97 may be pre-formed with an undulating shape.

Figure 11:
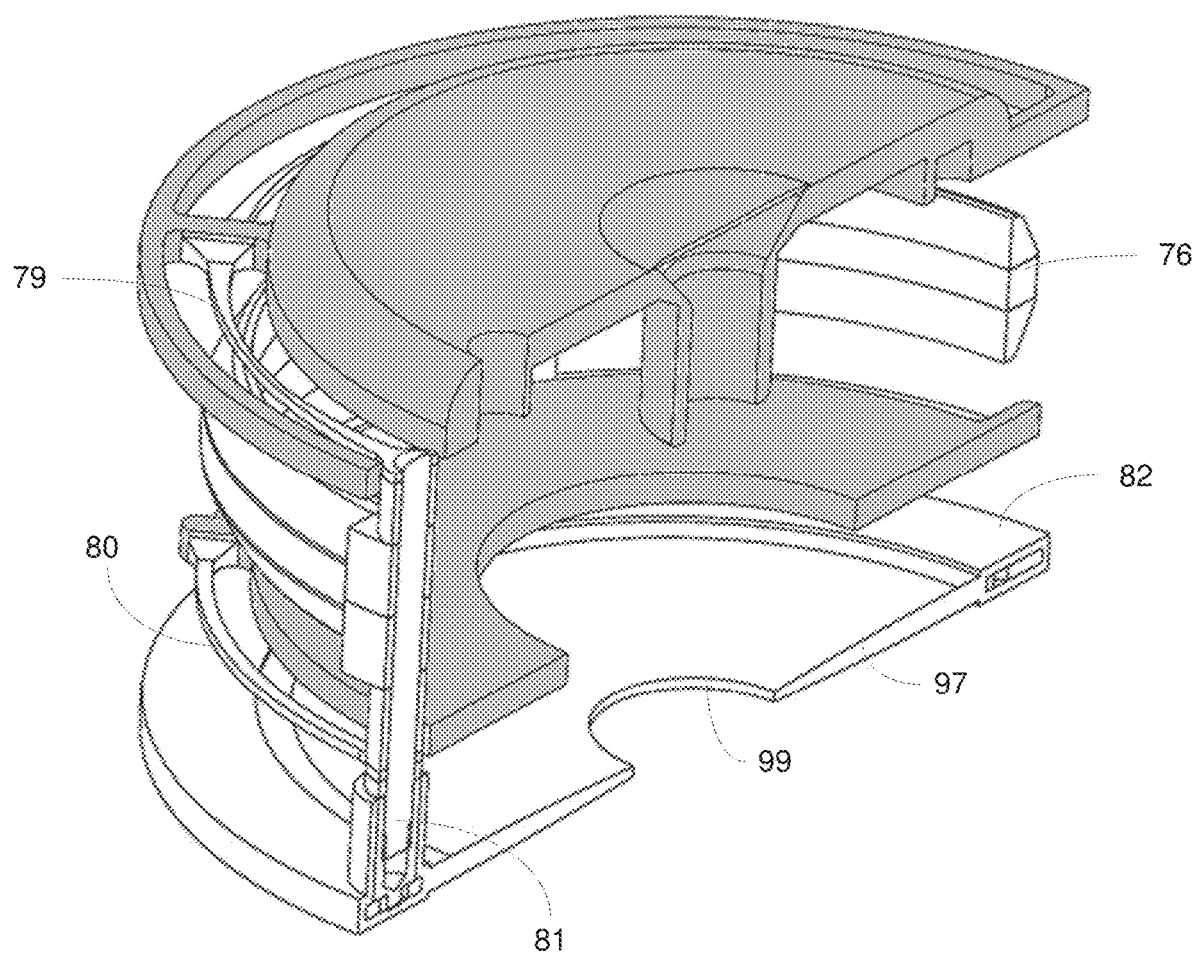
FIG. 11 is a perspective cross-sectional view of the moving components of the pump assembly according to a first embodiment of the present invention.

FIG. 11 depicts moving portions of the embodiment of pump assembly 70 shown in FIGS. 6-9 as non-grayed out elements. Non-moving portions of the pump assembly, including actuator assembly 95 and electromagnet assembly 91 (partially shown) may be fixed to pump housing 27 by fixation ring 71. Moving portions of pump assembly 70 may include posts 81, first suspension spring 79, magnetic ring assembly 76, second suspension spring 80 and membrane assembly 82. As magnetic ring assembly 76 moves up and down, the movement is rigidly translated by posts 81 to membrane assembly 82. Given the rigidity of the posts, when magnetic ring assembly 76 travels a certain distance upward or downward, membrane assembly 82 may travel the same distance. For example, when magnetic ring assembly 76 travels 2 mm from a position near first electromagnetic coil 77 to a position near second electromagnetic coil 78, membrane assembly 82 may also travel 2 mm in the same direction. Similarly, the frequency at which magnetic ring assembly 76 traverses the space between the first and second electromagnetic coils may be the same frequency at which membrane assembly 82 travels the same distance.

Figure 12:
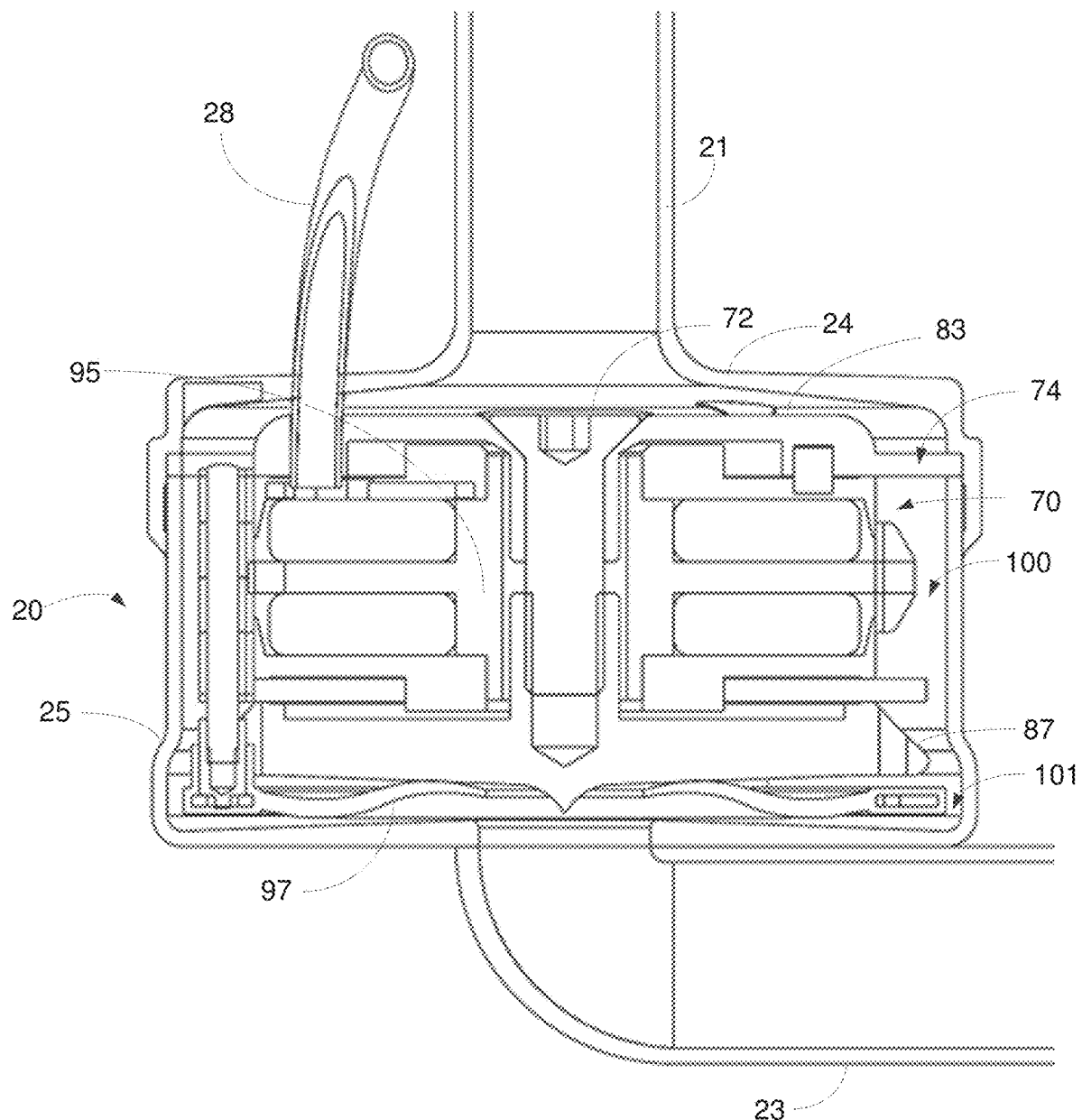
FIG. 12 is a cross-sectional view of the implantable pump of the present invention.

Referring now to FIG. 12, in the embodiment of implantable pump 20 described in FIGS. 6-9, blood may enter implantable pump 20 from the left ventricle through inlet cannula 21 and flow downward along pump assembly 70 into delivery channel 100, defined by the interior surface of pump housing 27 and exterior of pump assembly 70. Delivery channel 100 begins at the top of stator assembly 72 and extends between tapered section 83 and the interior of pump housing 27. As the blood moves down tapered section 83, it is directed through gap 74 and into a vertical portion of delivery channel 100 in the area between pump housing 27 and actuator assembly 95, and including in the gap between magnetic ring assembly 76 and electromagnet assembly 91. Delivery channel 100 extends down to flanged portion 87 of stator assembly 72, which routes blood into flow channel 101, within which membrane assembly 82 is suspended. By directing blood from inlet cannula 21 through delivery channel 100 to flow channel 101, delivery channel 100 delivers blood to membrane assembly 82. By actuating electromagnetic coils 77 and 78, membrane 97 may be undulated within flow channel 101 to induce wavelike formations in membrane 97 that move from the edge of the membrane towards circular aperture 99. Accordingly, when blood is delivered to membrane assembly 82 from delivery channel 100, it may be propelled radially along both the top and bottom of membrane 97 towards circular aperture 99, and from there out of outlet 23.

In accordance with one aspect of the present invention, the undulating membrane pump described herein reduces thrombus formation by placing moving parts directly within the primary flow path, thereby reducing the risk of flow stagnation. Specifically, the moving components depicted in FIG. 11, including magnetic ring assembly 76, suspension rings 79 and 80, posts 81 and membrane assembly 82 all are located within delivery channel 100 and flow channel 101. Flow stagnation may further be avoided by eliminating secondary flow paths that may experience significantly slower flow rates.

Turning now to FIGS. 13 and 14, a lower portion of implantable pump 20, including flanged portion 87, membrane assembly 82 and lower housing portion 23 is shown. Delivery channel 100 may be in fluid communication with membrane assembly 82 and flow channel 101 which is defined by a bottom surface of flanged portion 87 and the interior surface of lower housing portion 25. Flanged portion 87 may comprise feature 102 that extends downward as the bottom of flanged portion 87 moves radially inward. The interior surface of lower housing portion 25 may also slope upward as it extends radially inward. The combination of the upward slope of the interior surface of lower housing portion 25 and the bottom surface of flanged portion 87 moving downward narrows flow channel 101 as the channel moves radially inwards from delivery channel 100 to circular aperture 99 of membrane 97, which is disposed about pump outlet 23.

As explained above, membrane assembly 82 may be suspended by posts 81 within flow channel 101 below the bottom surface of flanged portion 87 and above the interior surface of lower housing portion 25. Membrane assembly 82 may be free to move up and down in the vertical direction within flow channel 101, which movement is constrained only by suspension rings 79 and 80. Membrane assembly 82 may be constrained from twisting, tilting or moving in any direction in flow channel 101 other than up and down by rigid posts 81 and by the suspension rings.

Flow channel 101 is divided by membrane 97 into an upper flow channel and a lower flow channel by membrane 97. The geometry of membrane 97 may be angled such that when membrane assembly 82 is at rest, the top surface of membrane 97 is parallel to the bottom surface of flanged portion 87 and the bottom surface of membrane 97 is parallel to the opposing surface of lower housing portion 25. Alternatively, membrane 97 may be sized and shaped such that when membrane assembly 82 is at rest, the upper and lower flow channels narrow as they move radially inward from delivery channel 100 to circular aperture 99 in membrane 97.

Referring now also to FIG. 14, as rigid membrane ring 96 is caused by posts 81 to move up and down in flow channel 101, the outermost portion of membrane 97 nearest rigid membrane ring 96, moves up and down with rigid membrane ring 96. Membrane 97, being flexible and having elastic properties, gradually translates the up and down movement of the membrane portion nearest rigid membrane ring 96 along membrane 97 towards circular aperture 99. This movement across flexible membrane 97 causes wavelike deformations in the membrane which may propagate inwards from rigid membrane ring 96 towards aperture 99.

The waves formed in the undulating membrane may be manipulated by changing the frequency at which rigid membrane ring 96 moves up and down as well as the distance rigid membrane ring 96 moves up and down. As explained above, the amplitude and frequency at which rigid membrane ring 96 moves up and down is determined by the amplitude and frequency at which magnetic ring assembly 76 reciprocates over electromagnet assembly 91. Accordingly, the waves formed in the undulating membrane may be adjusted by changing the frequency and amplitude at which magnetic ring assembly 76 is reciprocated.

When blood is introduced into flow channel 101 from delivery channel 100, the undulations in membrane 97 cause blood to be propelled toward circular aperture 99 and out of pump housing 27 via outlet 23. The transfer of energy from the membrane to the blood is directed radially inward along the length of the membrane towards aperture 99, and propels the blood along the flow channel towards outlet 23 along both sides of membrane 97.

For example, when rigid membrane ring 96 moves downward in unison with magnetic ring assembly 76, the upper portion of flow channel 101 near delivery channel 100 expands, causing blood from delivery channel 100 to fill the upper portion of the flow channel near the outer region of membrane 97. As rigid membrane ring 96 moves upward, the upper portion of flow channel 101 begins to narrow near rigid membrane ring 96, causing wave-like deformations to translate across the membrane. As the wave propagates across membrane 97, blood in the upper portion of flow channel 101 is propelled towards circular aperture and ultimately out of pump housing 27 through outlet 23. Simultaneously, as rigid membrane ring 96 moves upwards, the lower portion of flow channel 101 nearest the outer portion of membrane 97 begins to enlarge, allowing blood from delivery channel 100 to flow into this region. Subsequently, when rigid membrane ring 96 is again thrust downwards, the region of lower portion of flow channel 101 nearest outer portion of membrane 97 begins to narrow, causing wave-like deformations to translate across the membrane that propel blood towards outlet 23.

By manipulating the waves formed in the undulating membrane by changing the frequency and amplitude at which magnetic ring assembly 76 moves up and down, the pressure gradient within flow channel 101 and ultimately the flow rate of the blood moving through flow channel 101 may be adjusted. Appropriately controlling the movement of magnetic ring assembly 76 permits oxygen-rich blood to be effectively and safely pumped from the left ventricle to the aorta and throughout the body as needed.

In addition to merely pumping blood from the left ventricle to the aorta, implantable pump 20 of the present invention may be operated to closely mimic physiologic pulsatility, without loss of pump efficiency. In the embodiment detailed above, pulsatility may be achieved nearly instantaneously by changing the frequency and amplitude at which magnetic ring assembly 76 moves, to create a desired flow output, or by ceasing movement of the magnetic ring assembly for a period time to create a period of low or no flow output. Unlike typical rotary pumps, which require a certain period of time to attain a set number of rotations per minute to achieve a desired fluid displacement and pulsatility, implantable pump 20 may achieve a desired flow output nearly instantaneously and similarly may cease output nearly instantaneously due to the very low inertia generated by the small moving mass of the moving components of the pump assembly. The ability to start and stop on-demand permits rapid changes in pressure and flow. Along with the frequency and amplitude, the duty cycle, defined by the percentage of time membrane 97 is excited over a set period of time, may be adjusted to achieve a desired flow output and pulsatility, without loss of pump efficiency. Even holding frequency and amplitude constant, flow rate may be altered by manipulating the duty cycle between 0 and 100%.

In accordance with another aspect of the invention, controller 30 may be programmed by programmer 50 to operate at selected frequencies, amplitudes and duty cycles to achieve a wide range of physiologic flow rates and with physiologic hemodynamics. For example, programmer 50 may direct controller 30 to operate implantable pump 20 at a given frequency, amplitude and/or duty cycle during a period of time when a patient is typically sleeping and may direct controller 30 to operate implantable pump 20 at a different frequency, amplitude and or duty cycle during time periods when the patient is typically awake. Controller 30 or implantable pump also may include an accelerometer or position indicator to determine whether the patient is supine or ambulatory, the output of which may be used to move from one set of pump operating parameters to another. When the patient experiences certain discomfort or a physician determines that the parameters are not optimized, physician may alter one or more of at least frequency, amplitude and duty cycle to achieve the desired functionality. Alternatively, controller 30 or mobile device 60 may be configured to alter one or more of frequency, amplitude and duty cycle to suit the patient's needs.

Implantable pump 20 further may comprise one or more additional sensors for adjusting flow output and pulsatility according to the demand of the patient. Sensors may be incorporated into implantable pump 20 or alternatively or in addition to may be implanted elsewhere in or on the patient. The sensors preferably are in electrical communication with controller 30, and may monitor operational parameters that measure the performance of implantable pump 20 or physiological sensors that measure physiological parameters of the patients such as heart rate or blood pressure. By using one or more physiological sensors, pulsatile flow may be synchronized with a cardiac cycle of the patient by monitoring blood pressure or muscle contractions, for example, and synchronizing the duty cycle according to the sensed output.

Controller 30 may compare physiological sensor measurements to current implantable pump output. If it is determined by analyzing sensor measurements that demand exceeds current output, frequency, amplitude and/or duty cycle may be automatically adjusted to meet current demand. Similarly, the controller may determine that current output exceeds demand and thus alter output by changing frequency, amplitude and/or duty cycle. Alternatively, or in addition to, when it is determined that demand exceeds current output, an alarm may sound from controller 30. Similarly, operational measurements from operational sensors may be compared against predetermined thresholds and where measurements exceed predetermined thresholds or a malfunction is detected, an alarm may sound from controller 30.

Implantable pump 20 is sized and shaped to produce physiological flow rates, pressure gradients and pulsatility at an operating point at which maximum efficiency is achieved. Specially, implantable pump 20 may be sized and shaped to produce physiological flow rates ranging from 2 to 15 liters per minute at pressure gradients lower than a threshold value associated with hemolysis. Also, to mimic a typical physiological pulse of 60 beats per minute, implantable pump 20 may pulse about once per second. To achieve such pulsatility, a duty cycle of 20-50% may be utilized with an "on" or "high" period of 0.2-0.5 seconds and an "off" or "low" period of 0.5-0.8 seconds, for example, where a "high" setting represents an operating point of frequency and amplitude resulting in increased blood flow rates against physiologic pressure, whereas a "low" setting represents an operating point of frequency and amplitude resulting in lower blood flow rates against physiologic pressures. For a given system, maximum efficiency at a specific operating frequency, amplitude and voltage may be achieved while producing a flow rate of 2 to 15 liters per minute at a duty cycle of 20-50% by manipulating one or more of the shape and size of blood flow channels, elastic properties of the suspension rings, mass of the moving parts, membrane geometries, and elastic properties and friction properties of the membrane. In this manner, implantable pump 20 may be designed to produce desirable physiological outputs while continuing to function at optimum operating parameters.

By adjusting the duty cycle, implantable pump 20 may be configured to generate a wide range of output flows at physiological pressure gradients. For example, for an exemplary LVAD system configured to produce 2 to 15 liters per minute at a duty cycle of 20-50%, optimal operating frequency may be 25-70 Hz or even 120 Hz. For this system, flow output may be increased to 10 liters per minute or decreased to 4 liters per minute, for example, by changing only the duty cycle. As duty cycle and frequency operate independent of one another, duty cycle may be manipulated between 0 and 100% while leaving the frequency unaffected.

The implantable pump system described herein, tuned to achieve physiological flow rates, pressure gradients and pulsatility, also avoids hemolysis and platelet activation by applying low to moderate shear forces on the blood, similar to those encountered by blood elements in the normal, non-diseased vascular system. In the embodiment detailed above, delivery channel 100 may be sized and configured to also avoid friction between moving magnetic ring assembly 76, suspension rings 79 and 80, posts 81 and lower housing portion 25 by sizing the channel such that clearances of at least 0.5 mm are maintained between all moving components. Similarly, magnetic ring assembly 76, suspension rings 79 and 80, and posts 81 all may be offset from stator assembly 72 by at least 0.5 mm to avoid friction between the stator assembly and the moving parts.

Figure 15A:
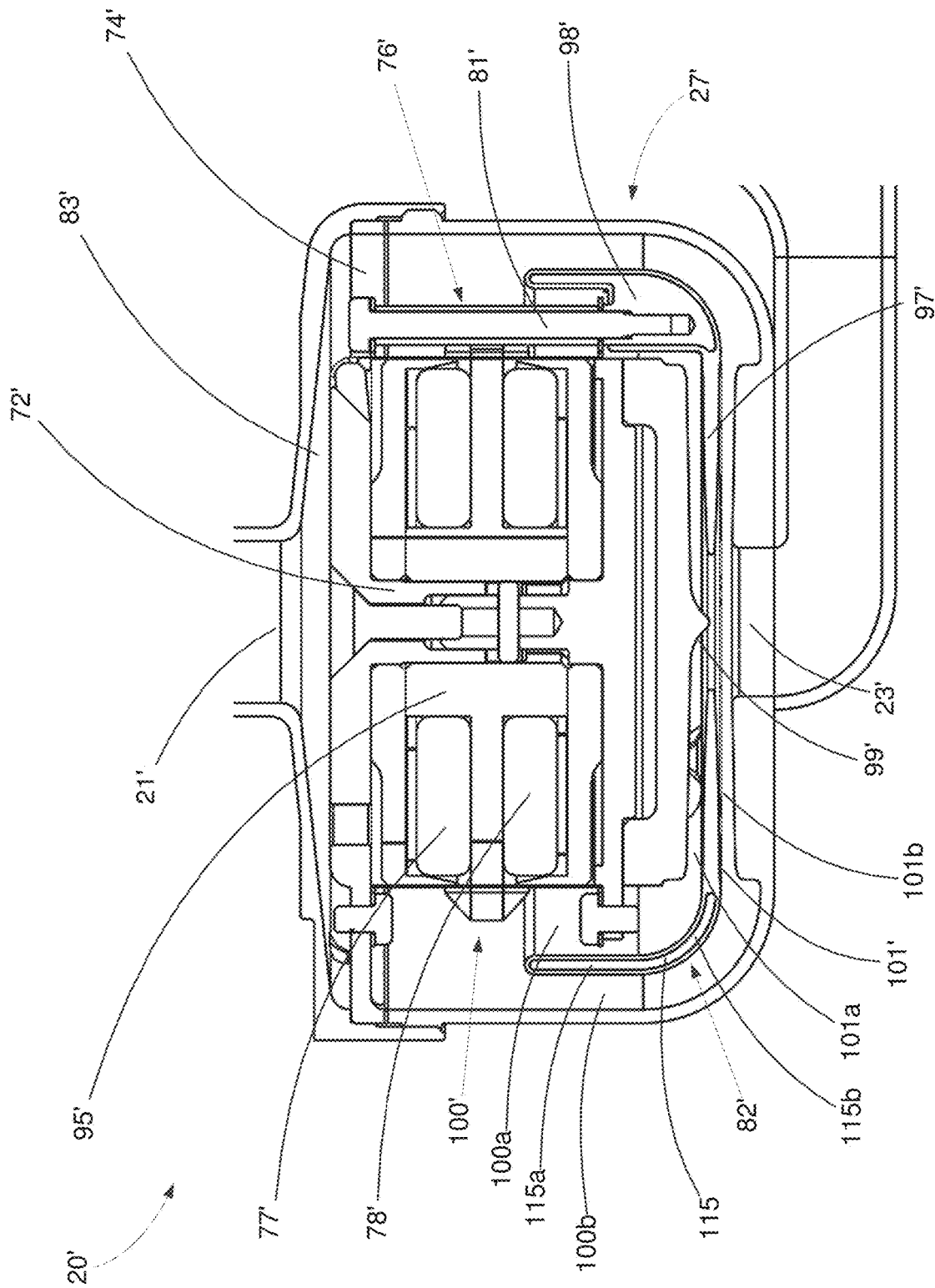
FIG. 15A is a cross-sectional view of an alternative exemplary embodiment of an implantable pump of the present invention with improved hydraulic performance for use in the pump system of FIG. 1.
Figure 15B:
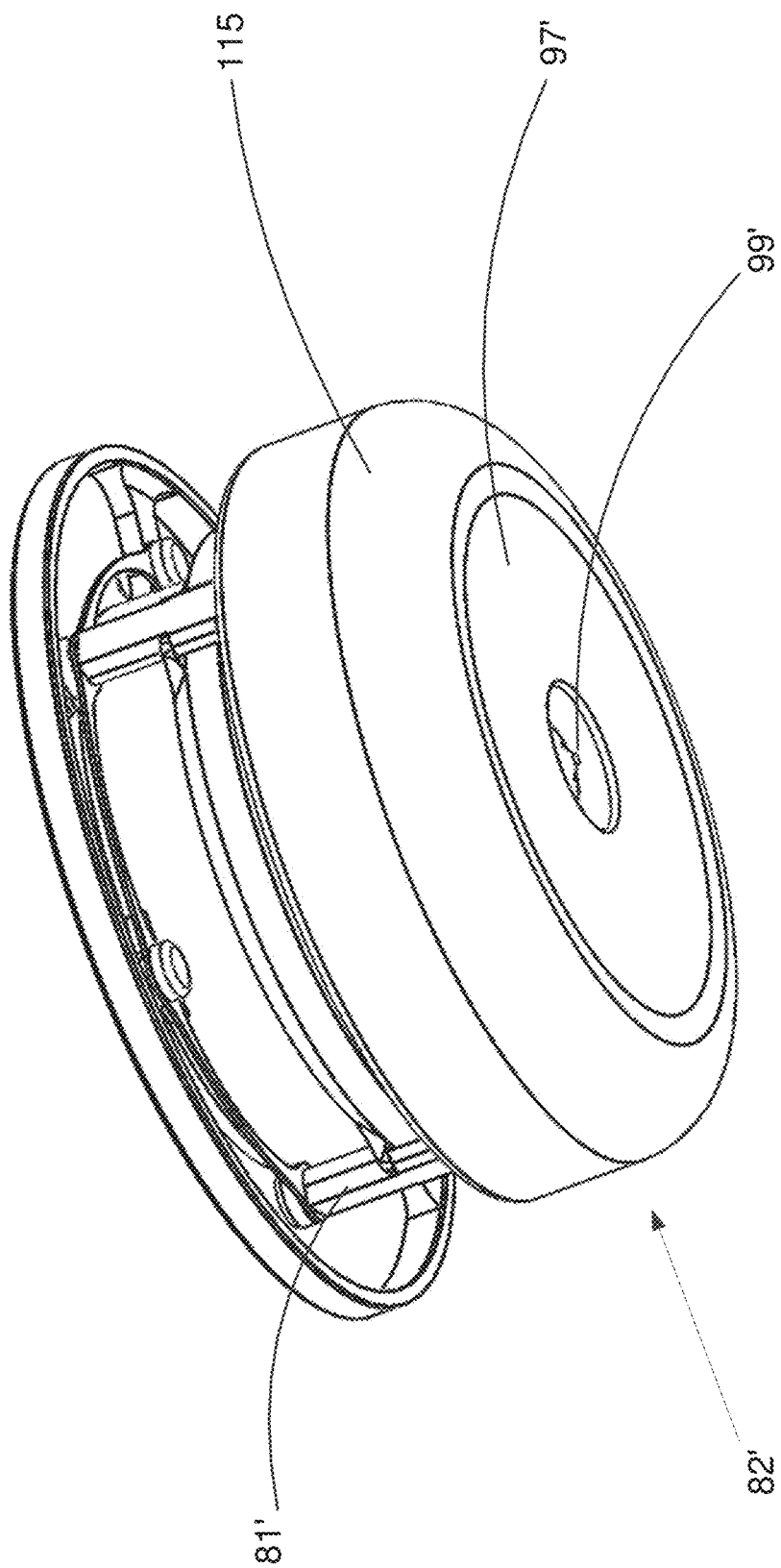
FIG. 15B is a perspective view of the implantable pump of FIG. 15A.

Referring now to FIGS. 15A and 15B, an alternative exemplary embodiment of the pump assembly of the present invention is described. Implantable pump 20' is constructed similar to implantable pump 20 described in FIGS. 7, 8, and 12, in which similar components are identified with like-primed numbers. Implantable pump 20' is distinct from implantable pump 20 in that membrane assembly 82' includes skirt 115 coupled to membrane 97'. Skirt illustratively includes first portion 115a and second portion 115b. First portion 115a of skirt 115 extends upward within delivery channel 100' toward inlet 21' in a first direction. e.g., parallel to the longitudinal axis of stator assembly 72' and/or to the central axis of pump housing 27'. Second portion 115b of skirt 115 curves toward outlet 23' such that second portion 115b is coupled to membrane 97' so that membrane 97' is oriented in a second direction. e.g., perpendicular to first portion 115a of skirt 115. For example, skirt 115 may have a J-shaped cross-section, such that first portion 115a forms a cylindrical-shaped ring about stator assembly 72' and second portion 115b has a predetermined radius of curvature which allows blood to flow smoothly from delivery channel 100' across skirt 115 to the outer edge of membrane 97' and into flow channel 101', while reducing stagnation of blood flow. Skirt 115 breaks flow recirculation of blood within delivery channel 100' and improves hydraulic power generated for a given frequency while minimizing blood damage. In addition, the J-shape of skirt 115 around stator assembly 72' may be stiffer than a planar rigid membrane ring, thereby reducing flexing and fatigue, as well as drag as the blood moves across membrane 97'.

Skirt 115 exhibits rigid properties under typical forces experienced during the full range of operation of the present invention and may be made of a biocompatible metal, e.g., titanium. Skirt 115 is preferably impermeable such that blood cannot flow through skirt 115. Post reception sites 98' may be formed into skirt 115 to engage membrane assembly 82' with posts 81'. Alternatively, posts 81' may be attached to skirt 115 in any other way which directly translates the motion of magnetic ring assembly 76' to skirt 115.

As magnetic ring assembly 76' moves up and down, the movement is rigidly translated by posts 81' to J-shape of skirt 115 of membrane assembly 82'. Given the rigidity of the posts, when magnetic ring assembly 76' travels a certain distance upward or downward, membrane assembly 82' may travel the same distance. For example, when magnetic ring assembly 76' travels 2 mm from a position near first electromagnetic coil 77' to a position near second electromagnetic coil 78', membrane assembly 82' may also travel 2 mm in the same direction. Similarly, the frequency at which magnetic ring assembly 76' traverses the space between the first and second electromagnetic coils may be the same frequency at which membrane assembly 82' travels the same distance.

Skirt 115 may be affixed to membrane 97' and hold membrane 97' in tension. Membrane 97' may be molded directly onto skirt 115 or may be affixed to skirt 115 in any way that holds membrane 97' uniformly in tension along its circumference. For example, skirt 115 may be coated with the same material used to form membrane 97' and the coating on skirt 115 may be integrally formed with membrane 97'.

Blood may enter implantable pump 20' from the left ventricle through inlet cannula 21' and flow downward along the pump assembly into delivery channel 100'. As the blood moves down tapered section 83', it is directed through gap 74' and into a vertical portion of delivery channel 100' in the area between pump housing 27' and actuator assembly 95'. As shown in FIG. 15A, skirt 115 divides delivery channel 100' into upper delivery channel 100a and lower delivery channel 100b such that blood flow through delivery channel 100' is divided into flow channel 101a via upper delivery channel 100a and flow channel 101b via lower delivery channel 100b, wherein flow channels 101a and 101b are separated by membrane 97'. As will be understood by one of ordinary skill in the art, the volume of blood flow through each of delivery channels 100a and 100b may depend on the diameter of first portion 115a of skirt 115. For example, the larger the diameter of first portion 115a of skirt 115, the larger the volume of delivery channel 100a and the smaller the volume of delivery channel 100b. The ratio of the volume of delivery channel 100a to the volume of delivery channel 100b may be, for example, 1:1, 1:2, 1:3, 1:4, 2:1, 3:1, 4:1, etc., depending on the amount of desired blood flow on each surface of membrane 97'.

Figure 16B:
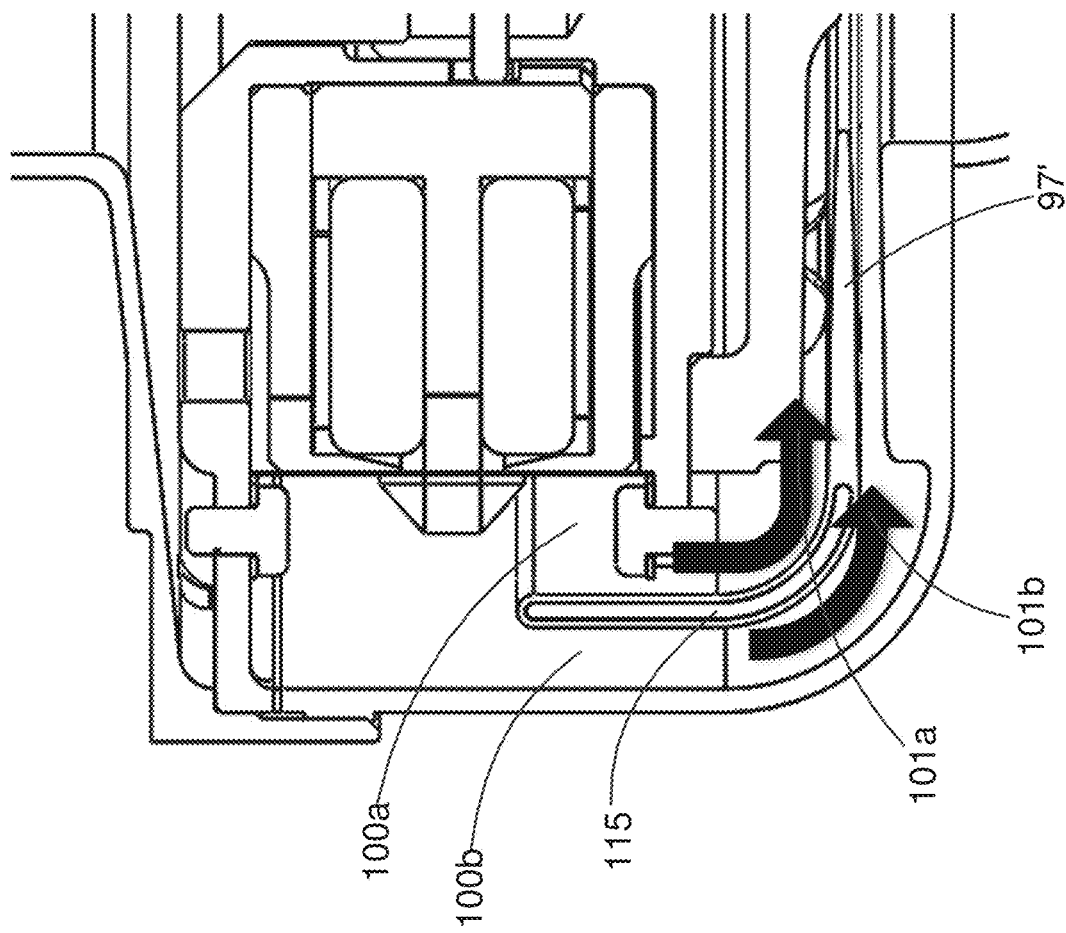
FIG. 16B illustrates blood flow using a pump assembly with a skirt in accordance with one aspect of the present invention.
Figure 16A:
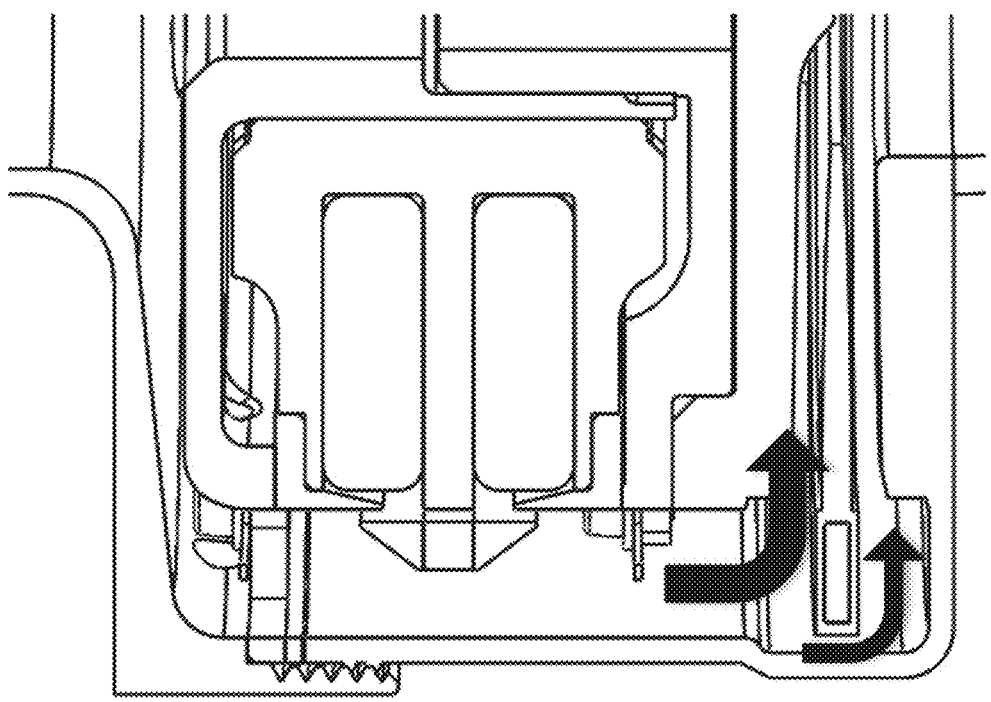

By directing blood from inlet cannula 21' across skirt 115 within delivery channel 100', blood flow is divided into delivery channel 100a and 100b and to flow channels 101a and 101b, respectively, such that blood flows across the upper and lower surfaces of membrane 97' of membrane assembly 82'. For example, as shown in FIG. 16A, blood flow through a pump having a planar rigid membrane ring spaced apart a relatively small distance from the pump housing may allow unrestricted blood flow across the upper surface of the flexible membrane while restricting blood flow across the lower surface of the flexible membrane. Whereas, as depicted in FIGS. 16B and 16C, blood flow through a pump having a J-shaped skirt or integrated portion may be distributed across both the upper and lower sides of the flexible membrane at a desired ratio.

Second portion 115b of skirt 115 curves toward outlet 23' such that second portion 115b is coupled to membrane 97' so that membrane 97' is oriented in a second direction, e.g., perpendicular to first portion 115a of skirt 115. For example, skirt 115 may have a J-shaped cross-section, such that first portion 115a forms a cylindrical-shaped ring about stator assembly 72' and second portion 115b has a predetermined radius of curvature which allows blood to flow smoothly from delivery channel 100' across skirt 115 to the outer edge of membrane 97' and into flow channel 101', while reducing stagnation of blood flow. Skirt 115 breaks flow recirculation of blood within delivery channel 100' and improves hydraulic power generated for a given frequency while minimizing blood damage. In addition, the J-shape of skirt 115 around stator assembly 72' may be stiffer than a planar rigid membrane ring, thereby reducing flexing and fatigue, as well as drag as the blood moves across membrane 97'.

Referring back to FIG. 15A, by actuating electromagnetic coils 77' and 78', membrane 97' may be undulated within flow channels 101a and 101b to induce wavelike formations in membrane 97' that move from the edge of membrane 97' towards circular aperture 99'. Accordingly, when blood is delivered to membrane assembly 82' from delivery channel 100', it may be propelled radially along both the upper and lower surfaces of membrane 97' towards circular aperture 99', and from there out of outlet 23'. The distribution of blood flow across the upper and lower surfaces of membrane 97' reduces recirculation of blood within delivery channel 101', and reduces repeated exposure of blood to high shear stress areas, which results in remarkably improved hydraulic performance of implantable pump 20'.

Referring now to FIG. 16C, implantable pump 400 is illustrated which is similar to implantable pump 20 and includes pump housing 402, integrated assembly 406, membrane 416 and actuator assembly 404 which may be the same or similar to actuator assembly 95. Integrated assembly 406 may be disposed around actuator assembly 404 and may include magnetic assembly 408 and transition portion 410. Magnetic assembly 408 may be similar to magnetic ring assembly 76 and/or may include one or more magnet 422 and/or iron portion 420. It is understood that magnetic assembly 408 may include a Halbach array. Integrated assembly 406 may further include outer cover 418 to permit hermetic sealing of the components in integrated assembly 406 (e.g., magnetic assembly 408) as well as magnet backing 424 to facilitate magnet alignment and assembly. Integrated assembly 406 may also include one or more bearing portions 419.

Integrated assembly 406 may be similar to skirt 115 in function, except that integrated assembly 406 may incorporate magnetic assembly 408. Integrated assembly 406 may extend upward within delivery channel 405 and further include transition portion 410 that extends toward membrane 416, which may be the same as or similar to membrane 97. Transition portion 410 may attach the integrated assembly 406 to membrane 416. Integrated assembly 406 may define a first blood channel 412 between integrated assembly 406 and pump housing 402 and may further define a second blood channel between integrated assembly 406 and actuator assembly 404. Similar to skirt 115, integrated assembly 406 may divert blood into first blood channel 412 and second blood channel 414 and ultimately to membrane 416.

Pump housing 402 may include one or more magnets 413 and one or more bearing portions 417. Bearing portion 417 may be in fluid communication (e.g., via blood in first blood channel 412) with bearing portion 419 and together may form a bearing that resists radial movement of moving assembly 406. Bearing portions 417 and 419 may be comprised of biocompatible materials, such as ceramics, alumina, zirconia, or zirconia-toughened alumina, or engineered plastics, such as poly-ether-ether-ketone (PEEK) and Delrin, or metallic alloys coated with tribologic coatings, such as titanium coated with titanium nitride (TiN) or zirconium nitride (ZrN). Magnets 413 and magnetic assembly 408 may interact to resist axial movement and cause moving assembly to return to a neutral position axially.

One or more magnets of magnetic assembly 408 may be enlarged to increase second blood channel 414, while maintaining attraction between one or more coils (e.g., coils 411) of actuator assembly 404 and magnetic assembly 408. The increased second blood channel 414 may reduce the risk of shear-induced damage to the blood and/or thermal injury. As shown in FIG. 16C, implantable pump 400 may having a single moving assembly (e.g., integrated assembly 406) in addition to membrane 416.

Figure 16D:
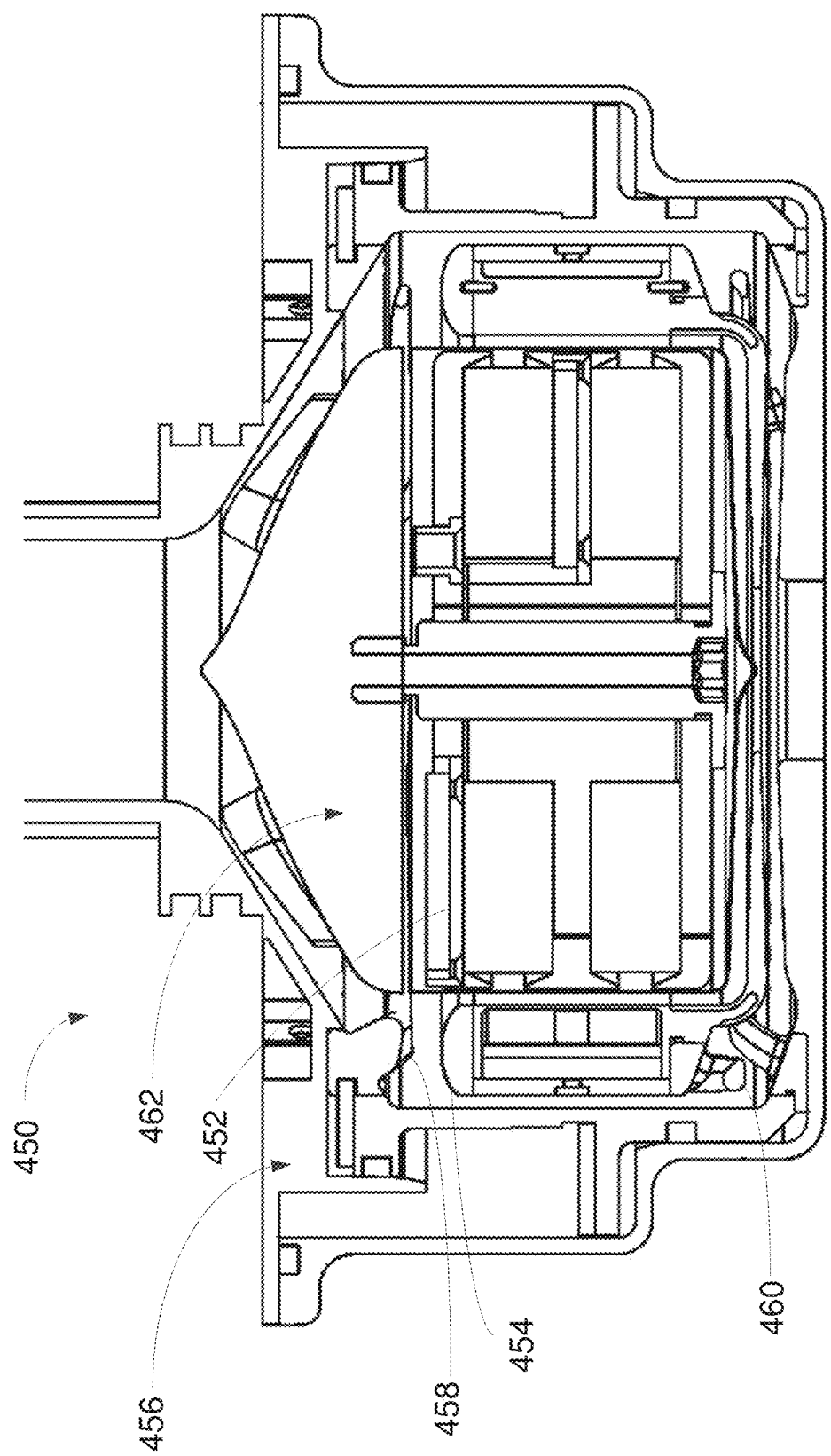
FIG. 16D illustrates a blood pump with an integrated portion incorporating a magnetic assembly and featuring mechanical springs.

Referring now to FIG. 16D, implantable pump 450 including inlet spring 458 and outlet spring 460 is illustrated. Implantable pump 450 may be similar to implantable pump 400 and may include actuator assembly 452, which may be similar to actuator assembly 404, pump housing 456, which may be similar to pump housing 402, and integrated assembly 454, which may be similar to integrated assembly 406. As shown in FIG. 16, integrated assembly 454 may be coupled to inlet spring 458 and outlet spring 460. Inlet spring 456 and outlet spring 460 may be coupled at one end to integrated assembly 454 and at the other end to pump housing 456. Inlet spring 458 and outlet spring 460 may be monobloc springs, for example, or any other well-known springs. Inlet spring 458 and outlet spring 460, may be comprised of biocompatible metals, such as stainless steel, titanium, or cobalt chromium, for example, and/or may be processed by methods to remove surface defects or cold work the materials to increase durability and hemocompatibility. Inlet spring 458 and outlet spring 460 may resist both radial and axial movement of moving assembly 456 and may cause moving assembly 456 to return to a neutral position. It is understood that inlet spring 458 and/or outlet spring 460 may be optional. As also shown in FIG. 16D, dampening structure 462 may be coupled to and/or extend from actuator assembly 452 and may facilitate in dampening vibration of implantable pump 450 (e.g., caused by moving assembly 454). Dampening structure 462 may be comprised of polymer materials, such as biocompatible polyurethane, for example, with Shore Hardness values from 20 to 80 A. It is understood that inlet spring 458 and outlet spring 460 may be the same or similar to suspension springs.

Figure 17:
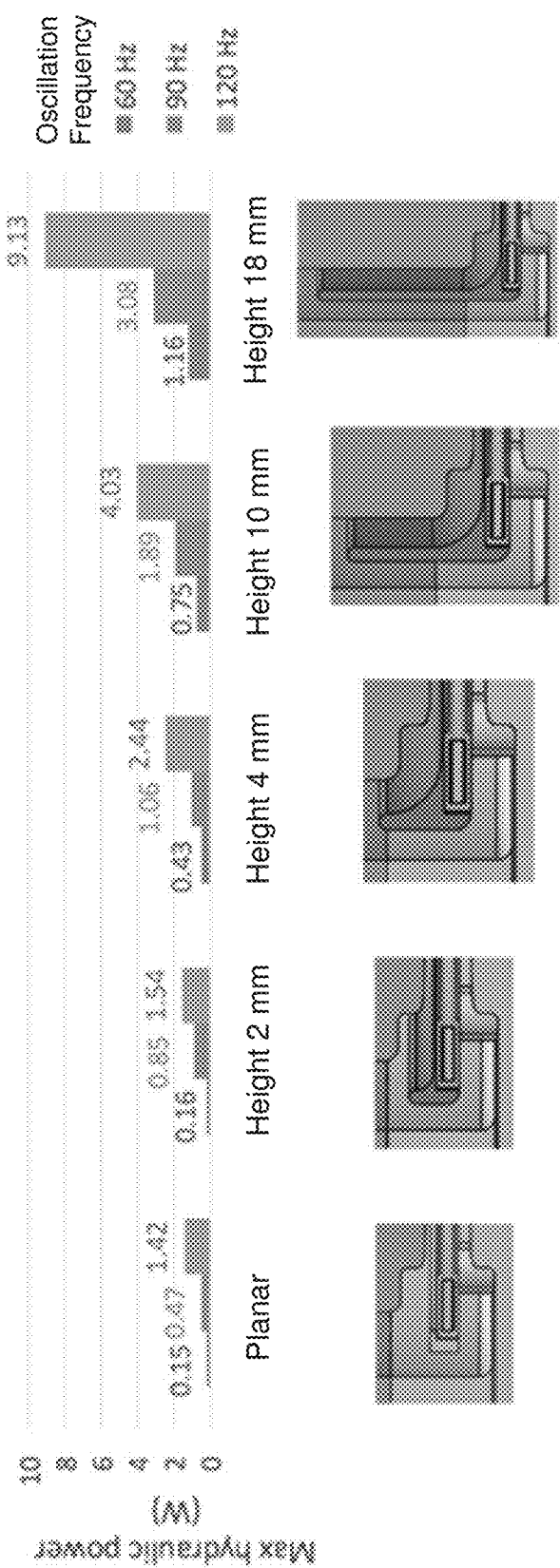
FIG. 17 shows graphs illustrating the relationship between max hydraulic power and the height of the skirt.

Referring now to FIG. 17, the relationship between the maximum hydraulic power of the pump system and the height of the J-shaped skirt is described. As the height of the vertical portion of the skirt increases, the maximum hydraulic power of the pump increases at a nonlinear rate. For example, as shown in FIG. 17, operation of a pump having a planar rigid membrane ring at 60 Hz results in a maximum of 0.15 W of hydraulic power, at 90 Hz results in a maximum of 0.47 W of hydraulic power, and at 120 Hz results in a maximum of 1.42 W of hydraulic power. Operation of a pump having a skirt with an extension height of 2 mm, measured from the top surface of the membrane ring to the top of the J-shaped skirt, at 60 Hz results in a maximum of 0.16 W of hydraulic power, at 90 Hz results in a maximum of 0.85 W of hydraulic power, and at 120 Hz results in a maximum of 1.54 W of hydraulic power. Operation of a pump having a skirt with an extension height of 4 mm at 60 Hz results in a maximum of 0.43 W of hydraulic power, at 90 Hz results in a maximum of 1.06 W of hydraulic power, and at 120 Hz results in a maximum of 2.44 W of hydraulic power. Operation of a pump having a skirt with an extension height of 10 mm at 60 Hz results in a maximum of 0.75 W of hydraulic power, at 90 Hz results in a maximum of 1.89 W of hydraulic power, and at 120 Hz results in a maximum of 4.03 W of hydraulic power. Operation of a pump having a skirt with an extension height of 18 mm at 60 Hz results in a maximum of 1.16 W of hydraulic power, at 90 Hz results in a maximum of 3.08 W of hydraulic power, and at 120 Hz results in a maximum of 9.13 W of hydraulic power. As such, height of skirt 115 is preferably at least 2 mm, and more preferably at least 4 mm, at least 10 mm, and/or at least 18 mm. Accordingly, implantable pump 20' may be operated at a significantly lower frequency to achieve the same hydraulic output as a pump having a planar rigid membrane ring operating at a higher frequency, while reducing blood damage and increasing fatigue life of membrane 97' and the springs.

Figure 18:
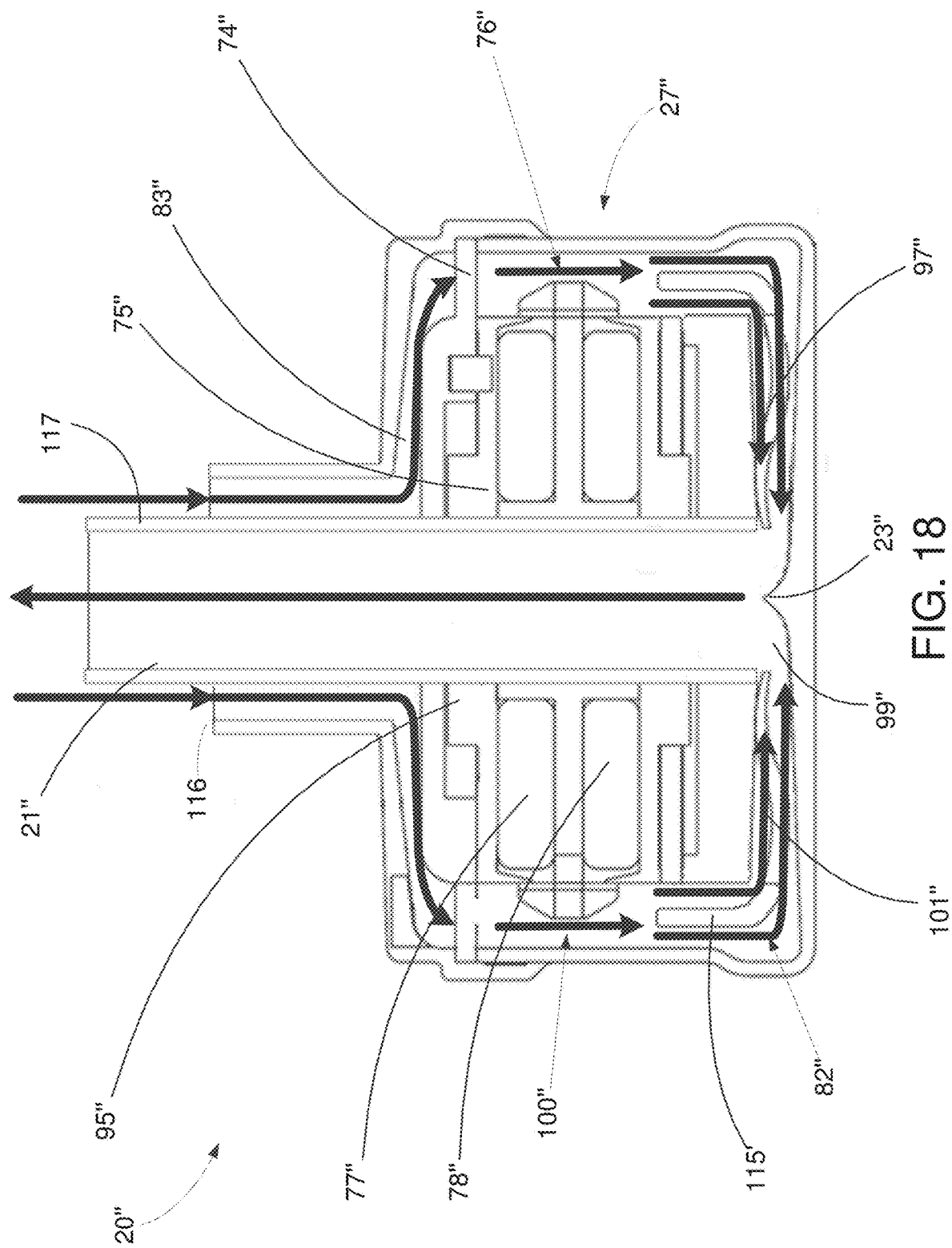
FIG. 18 is a cross-sectional view of yet another alternative exemplary embodiment of an implantable pump of the present invention with improved hydraulic performance, wherein the outflow cannula is disposed coaxially within the inflow cannula.

Referring now to FIG. 18, an alternative exemplary embodiment of the pump assembly of the present invention having a J-shaped skirt is described. Implantable pump 20" is constructed similar to implantable pump 20' described in FIG. 15A, in which similar components are identified with like-double primed numbers. In addition, implantable pump 20" includes skirt 115' which is constructed similar to skirt 115 of FIG. 15A. Implantable pump 20" is distinct from implantable pump 20' in that inlet 21" is coupled to inflow cannula 116, and outlet 23" is coupled to outflow cannula 117 such that outflow cannula 117 is disposed coaxially within inflow cannula 116, as described in U.S. Patent Publication No. 2017/0290967 to Botterbusch, the entire contents of which are incorporated herein by reference. Accordingly, during operation, blood flows into inlet 21" via inflow cannula 116, through delivery channel 100" into flow channel 101" across membrane 97", and exits through outlet cannula 117 via outlet 23".

Figure 19:
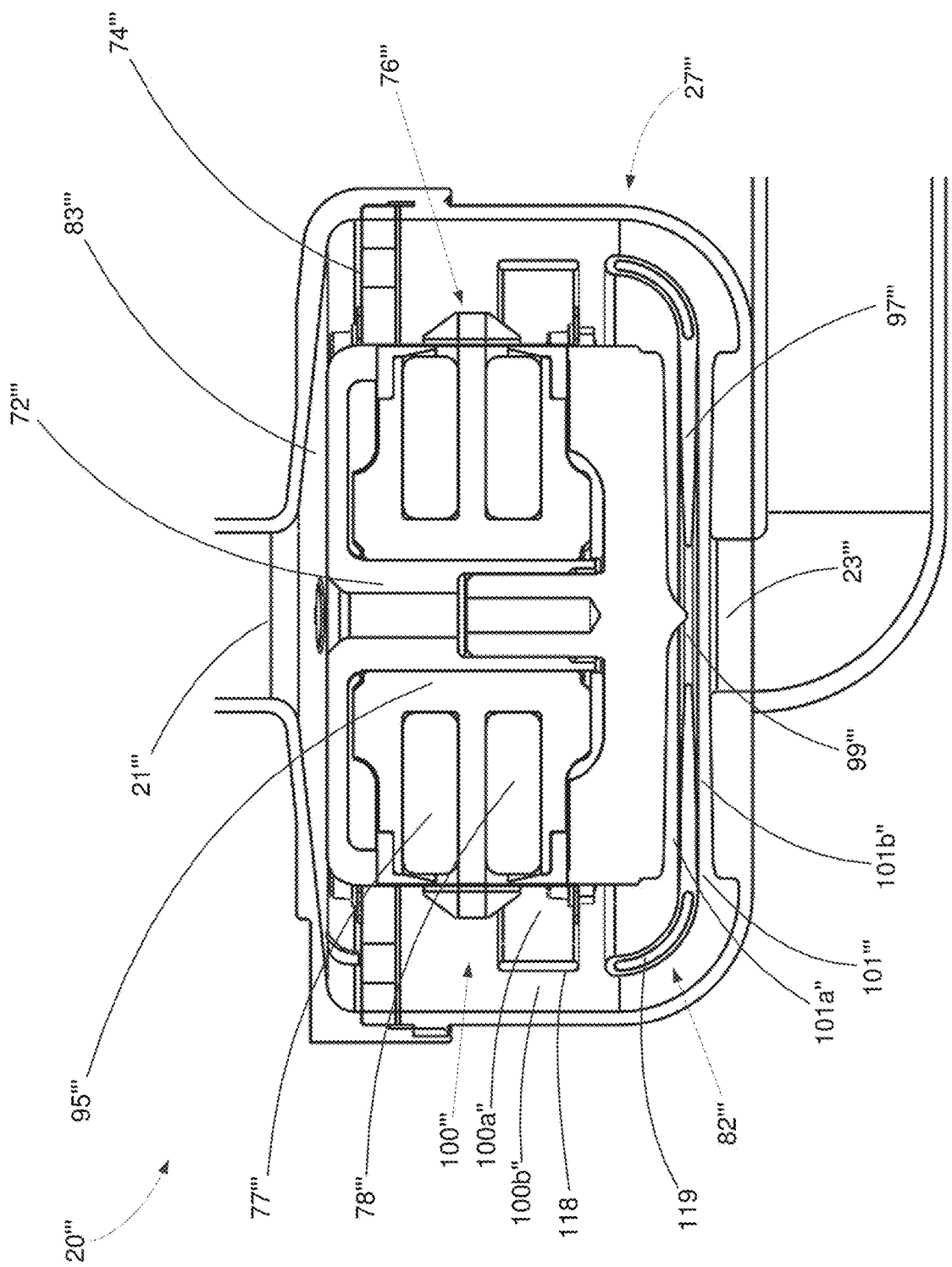
FIG. 19 is a cross-sectional view of yet another alternative exemplary embodiment of an implantable pump of the present invention having a ring and skirt with improved hydraulic performance for use in the pump system of FIG. 1.

Referring now to FIG. 19, another alternative exemplary embodiment of the pump assembly of the present invention is described. Implantable pump 20'" is constructed similar to implantable pump 20' described in FIGS. 15A and 15B, in which similar components are identified with like-double primed numbers and like-triple primed numbers. Implantable pump 20'" is distinct from implantable pump 20' in that implantable pump 20'" includes rigid ring 118 fixed about stator assembly 72'". Ring 118 extends longitudinally within delivery channel 100'", parallel to the longitudinal axis of stator assembly 72'" such that ring 118 forms a cylindrical-shaped ring about stator assembly 72'".

In addition, membrane assembly 82'" of implantable pump 20'" includes skirt 119 coupled to membrane 97'". The upper portion of skirt 119 is substantially parallel to ring 118, and the lower portion of skirt 119 curves toward outlet 23'" such that skirt 119 is coupled to membrane 97'", perpendicular to ring 118. For example, skirt 119 may have a J-shaped cross-section, having a predetermined radius of curvature which allows blood to flow smoothly from delivery channels 100a" and 100b" across skirt 119 to the outer edge of membrane 97'" within flow channel 101'", while reducing stagnation of blood flow. Together, ring 118 and skirt 119 breaks flow recirculation of blood within delivery channel 100'" and improves hydraulic power generated for a given frequency while minimizing blood damage. The distance between ring 118 and skirt 119 as skirt 119 reciprocates in response to the magnetic field generated by magnetic ring assembly 76'" as described in further detail below, is minimized to reduce leakage of blood between delivery channels 100a" and 100b", and to reduce blood damage. In addition, the J-shape of skirt 119 is significantly stiffer than a planar rigid membrane ring, thereby reducing flexing and fatigue, as well as drag as the blood moves across membrane 97'".

Skirt 119 is preferably impermeable such that blood cannot flow through skirt 119, and exhibits rigid properties under typical forces experienced during the full range of operation of the present invention and may be made of a biocompatible metal, e.g., titanium. Post reception sites may be formed into skirt 119 to engage membrane assembly 82'" with the posts. Alternatively, the posts may be attached to skirt 119 in any other way which directly translates the motion of magnetic ring assembly 76'" to skirt 119.

As magnetic ring assembly 76'" moves up and down, the movement is rigidly translated by the posts to skirt 119 of membrane assembly 82'". Given the rigidity of the posts, when magnetic ring assembly 76'" travels a certain distance upward or downward, membrane assembly 82'" may travel the same distance. For example, when magnetic ring assembly 76'" travels 2 mm from a position near first electromagnetic coil 77'" to a position near second electromagnetic coil 78'", membrane assembly 82'" may also travel 2 mm in the same direction. Similarly, the frequency at which magnetic ring assembly 76'" traverses the space between the first and second electromagnetic coils may be the same frequency at which membrane assembly 82'" travels the same distance.

Skirt 119 may be affixed to membrane 97'" and hold membrane 97'" in tension. Membrane 97'" may be molded directly onto skirt 119 or may be affixed to skirt 119 in any way that holds membrane 97'" uniformly in tension along its circumference. For example, skirt 119 may be coated with the same material used to form membrane 97'" and the coating on skirt 119 may be integrally formed with membrane 97'".

Blood may enter implantable pump 20'" from the left ventricle through inlet 21'" and flow downward along the pump assembly into delivery channel 100'". As the blood moves down tapered section 83'", it is directed through gap 74'" and into a vertical portion of delivery channel 100'" in the area between pump housing 27'" and actuator assembly 95'". As shown in FIG. 19, ring 118 divides delivery channel 100'" into upper delivery channel 100a" and lower delivery channel 100b" such that blood flow through delivery channel 100'" is divided into flow channel 101a" via upper delivery channel 100a" and flow channel 101b" via lower delivery channel 100b" and across skirt 119 with minimal leakage between delivery channel 100a" and delivery channel 100b", wherein flow channels 101a" and 101b" are separated by membrane 97'".

As will be understood by one of ordinary skill in the art, the volume of blood flow through each of delivery channels 100a" and 100b" may depend on the diameter of ring 118 and the curvature of radius of skirt 119. For example, the larger the diameter of ring 118, the larger the volume of delivery channel 100a" and the smaller the volume of delivery channel 100b". The ratio of the volume of delivery channel 100a" to the volume of delivery channel 100b" may be, for example, 1:1, 1:2, 1:3, 1:4, 2:1, 3:1, 4:1, etc., depending on the amount of desired blood flow on each surface of membrane 97'". By directing blood from inlet cannula 21" across ring 118 within delivery channel 100'", blood flow is divided into delivery channels 100a" and 100b" and across skirt 119 to flow channels 101a" and 101b", respectively, such that blood flows across the upper and lower surfaces of membrane 97'" of membrane assembly 82'".

By actuating electromagnetic coils 77'" and 78'", membrane 97'" may be undulated within flow channels 101a" and 101b" to induce wavelike formations in membrane 97'" that move from the edge of membrane 97'" towards circular aperture 99'". Accordingly, when blood is delivered to membrane assembly 82'" from delivery channel 100'", it may be propelled radially along both the upper and lower surfaces of membrane 97'" towards circular aperture 99'", and from there out of outlet 23'". The distribution of blood flow across the upper and lower surfaces of membrane 97'" reduces recirculation of blood within delivery channel 101'" and reduces repeated exposure of blood to high shear stress areas, which results in remarkably improved hydraulic performance of implantable pump 20'".

Figure 20:
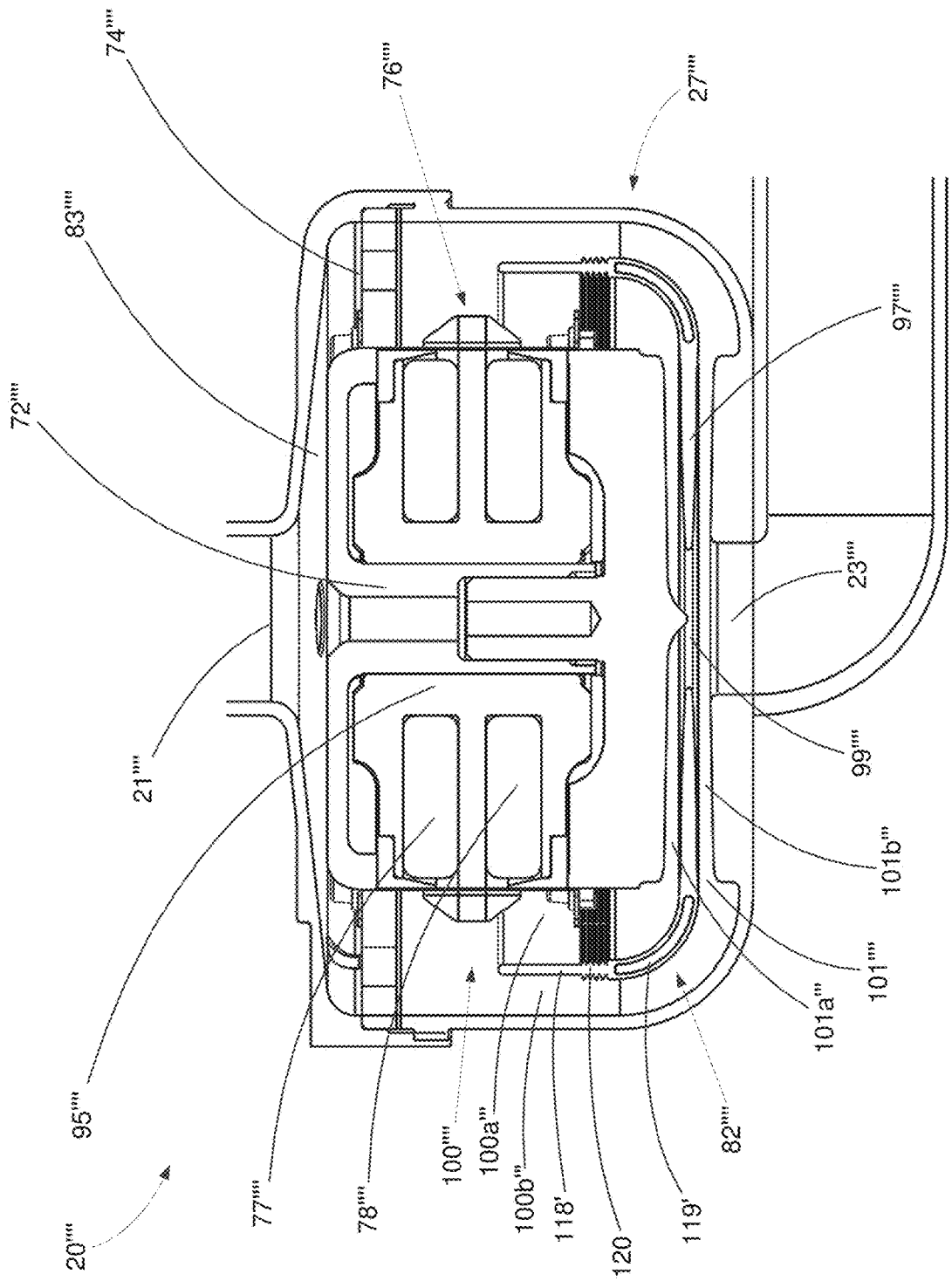
FIG. 20 is a cross-sectional view of yet another alternative exemplary embodiment of an implantable pump of the present invention having a ring, skirt, and expandable portion with improved hydraulic performance for use in the pump system of FIG. 1.

Referring now to FIG. 20, yet another alternative exemplary embodiment of the pump assembly of the present invention is described. Implantable pump 20'''' is constructed similar to implantable pump 20''' described in FIG. 19, in which similar components are identified with like-primed, like-triple primed, and like-quadruple primed numbers. Implantable pump 20'''' is distinct from implantable pump 20''' in that implantable pump 20'''' includes expandable portion 120 coupled between ring 118' and the upper portion of skirt 119'. Expandable portion 120 is impermeable and prevents leakage between delivery channels 100a''' and 100b'''. Preferably, expandable portion 120 has a pleated configuration that may expand and contract to permit efficient reciprocation of skirt 119' relative to ring 118'. For example, expandable portion 120 may comprise a plurality of bellows having a first end coupled to ring 118' and a second end coupled to skirt 119'.

Expandable portion 120 may be molded directly onto skirt 119' or may be affixed to skirt 119' in any way that holds expandable portion 120 uniformly along its circumference. Similarly, expandable portion 120 may be molded directly onto ring 118' or may be affixed to ring 118' in any way that holds expandable portion 120 uniformly along its circumference. Skirt 119' may be coated with the same material used to form membrane 97'''' and/or expandable portion 120 and the coating on skirt 119' may be integrally formed with membrane 97'''' and/or expandable portion 120.

As shown in FIG. 20, expandable portion 120 extends longitudinally within delivery channel 100'''', parallel to the longitudinal axis of stator assembly 72''''. Thus, during operation, blood is directed from inlet cannula 21'''' across ring 118' and expandable portion 120 within delivery channel 100'''' and divided into delivery channels 100a''' and 100b''' and across skirt 119' to flow channels 101a''' and 101b''', respectively, such that blood flows across the upper and lower surfaces of membrane 97'''' of membrane assembly 82''''.

As magnetic ring assembly 76'''' moves up and down, the movement is rigidly translated by the posts to skirt 119' of membrane assembly 82'''', and thereby to expandable portion 120. For example, when magnetic ring assembly 76'''' travels a certain distance upward or downward, membrane assembly 82'''' travels the same distance causing expandable portion 120 to expand and contract within delivery channel 100'''' parallel to the longitudinal axis of stator assembly 72'''' by the same distance. Similarly, the frequency at which magnetic ring assembly 76'''' traverses the space between the first and second electromagnetic coils may be the same frequency at which membrane assembly 82'''' travels the same distance.

Referring now to FIGS. 21A-21H, various configurations for energizing the implantable pumps of the present invention. e.g., implantable pumps 20, 20'', 20''', and 20'''', described above are provided. As shown in FIG. 21A, controller 30 includes output port 33 which is electrically coupled to cable 29 as described above, which in turn is coupled to the implantable pump. Controller 30 also includes power connector 103, which may be electrically coupled to a battery, an extension port electrically coupled to a battery, or an AC/DC power supply. For example, power connector 103 may be male, while the connector of the corresponding battery or extension port is female.

In one embodiment, as shown in FIG. 21B, controller 30 includes two power connectors, e.g., first power connector 103 and second power connector 104. As described above, first power connector 103 may be electrically coupled to a first battery, a first extension port electrically coupled to a first battery, or a first AC/DC power supply, and second power connector 103 may be electrically coupled to a second battery, a second extension port electrically coupled to a second battery, or a second AC/DC power supply. In this embodiment, first power connector 103 and second power connector 104 may both be male. In addition, controller 30 includes circuitry for switching between power sources such that energy is selectively transmitted to controller 30 from at least one of the first or second battery/power supply. For example, the circuitry may switch between a first and second battery intermittently, or after the remaining power level of one of the batteries reaches a predetermined threshold.

Referring now to FIGS. 21C-E, configurations are illustrated wherein controller 30 is directly electrically coupled to battery 40, such that controller 30 and battery 40 may be worn by the patient together, e.g., via a purse, shoulder bag, or holster. As shown in FIG. 21C, controller 30 of FIG. 21A may be electrically coupled to battery 40 via power connector 103, wherein power connector 103 is male and battery 40 has a corresponding female connector. For example, FIG. 21D illustrates controller 30 electrically coupled to battery 40, wherein battery 40 has a smaller size, and therefore lower capacity, and FIG. 21E illustrates controller 30 electrically coupled to battery 40, wherein battery 40 has a larger size, and therefore higher capacity. As will be understood by a person of ordinary skill in the art, battery 40 may have various sizes depending on the need of the patient.

Referring now to FIGS. 21F-H, configurations are illustrated wherein controller 30 is remotely electrically coupled to battery 40, such that the weight and volume of controller 30 and battery 40 are distributed and may be worn by the patient separately, e.g., via a belt or a vest. As shown in FIG. 21F, cable 41, which electrically couples controller 30 to battery 40, is electrically coupled to first power connector port 105 via strain relief 106, which is a hardwired junction between cable 41 and first power connector port 105. Power connector port 105 includes power connector 107, which may be electrically coupled to a battery. For example, power connector 107 may be male, while the connector of the corresponding battery is female.

As shown in FIG. 21G, controller 30 may be remotely electrically coupled to battery 40 via cable 41. Cable 41 is electrically coupled at one end to controller 30 via second power connector port 108 and strain relief 114, which is a hardwired junction between cable 41 and second power connector port 108, and electrically coupled at another end to battery 40 via first connector port 105 and strain relief 106. For example, power connector 103 of controller 30 may be male while the connector of corresponding second power connector port 108 is female, and power connector 107 of first power connector port 105 may be male while the connector of corresponding battery 40 is female.

In one embodiment, as shown in FIG. 21H, controller 30 may be remotely electrically coupled to multiple batteries, e.g., battery 40A and battery 40B, via a single second power connector port 108. As shown in FIG. 21H, second power connector port 108 includes first strain relief 114A and second strain relief 114B, such that controller 30 is remotely electrically coupled to battery 40A via cable 41A and remotely electrically coupled to battery 40B via cable 41B. Specifically, cable 41A is electrically coupled at one end to controller 30 via second power connector port 108 and first strain relief 114A, and electrically coupled at another end to battery 40A via first connector port 105A and strain relief 106A, and cable 41B is electrically coupled at one end to controller 30 via second power connector port 108 and second strain relief 114B, and electrically coupled at another end to battery 40B via first connector port 105B and strain relief 106B. In this embodiment, controller 30 may include circuitry for switching between battery 40A and battery 40B such that energy is selectively transmitted to controller 30 from at least one of battery 40A and battery 40B. For example, the circuitry may switch between battery 40A and battery 40B intermittently, or after the remaining power level of one of the batteries reaches a predetermined threshold. Alternatively, controller 30 may receive energy from battery 40A and battery 40B simultaneously.

In another embodiment, as shown in FIG. 21I, controller 30 is electrically coupled to AC/DC power supply 109, which may be plugged into an electrical outlet via AC plug 113, e.g., when the patient is resting bedside. Specifically, AC/DC power supply 109 is electrically coupled to controller 30 via cable 41, such that cable 41 is electrically coupled at one end to controller 30 via second power connector port 108 and strain relief 114, and electrically coupled at another end to AC/DC power supply 109 via first power supply port 110. In addition, AC/DC power supply 109 is electrically coupled to plug 113 via cable 112 and second power supply port 111.

Controller 30 may include an internal battery, such that the internal battery powers controller 30 and the implantable pump during the time required for battery 40 to be replaced and/or recharged. Accordingly, controller 30 may include circuitry for switching between power sources such that energy is transmitted to controller 30 from the internal battery while battery 40 is disconnected from controller 30, and from battery 40 when battery 40 is electrically coupled to controller 30. In addition, the circuitry may allow battery 40 to charge the internal battery while also energizing the implantable pump until the internal battery is recharged to a desired amount, at which point the circuitry allows battery 40 to solely energize the implantable pump. Similarly, when controller 40 is electrically coupled to AC/DC power supply 109, the circuitry may allow AC/DC power supply 109 to charge the internal battery while also energizing the implantable pump until the internal battery is recharged to a desired amount, at which point the circuitry allows AC/DC power supply 109 to solely energize the implantable pump.

In accordance with the principles of the present invention, systems and methods for controlling an implantable pump constructed in accordance with the principles of the present invention, e.g., implantable pumps 20, 20", 20''', and 20"", without requiring position, velocity, or acceleration sensors are provided. Specifically, an exemplary controller, e.g., controller 30, for the implantable pump only relies on the actuator's current measurement. The controller is robust to pressure and flow changes inside the pump head, and allows fast change of pump's operation point. For example, the controller includes, a two stage, nonlinear position observer module based on a reduced order model of the electromagnetic actuator. As the actuator is very small regarding its performance requirements, linear approximation of the equivalent electric circuit is insufficient. To meet the required operational range of the controller, the controller includes parameters' variations regarding state variables. Means to identify the actuator's model are given by a recursive least squares (RLS) so they can be incorporated in a sensible way into the position observer module of the controller. A forgetting factor is further included in the RLS to capture model parameters' variations regarding state variables.

Figure 22:
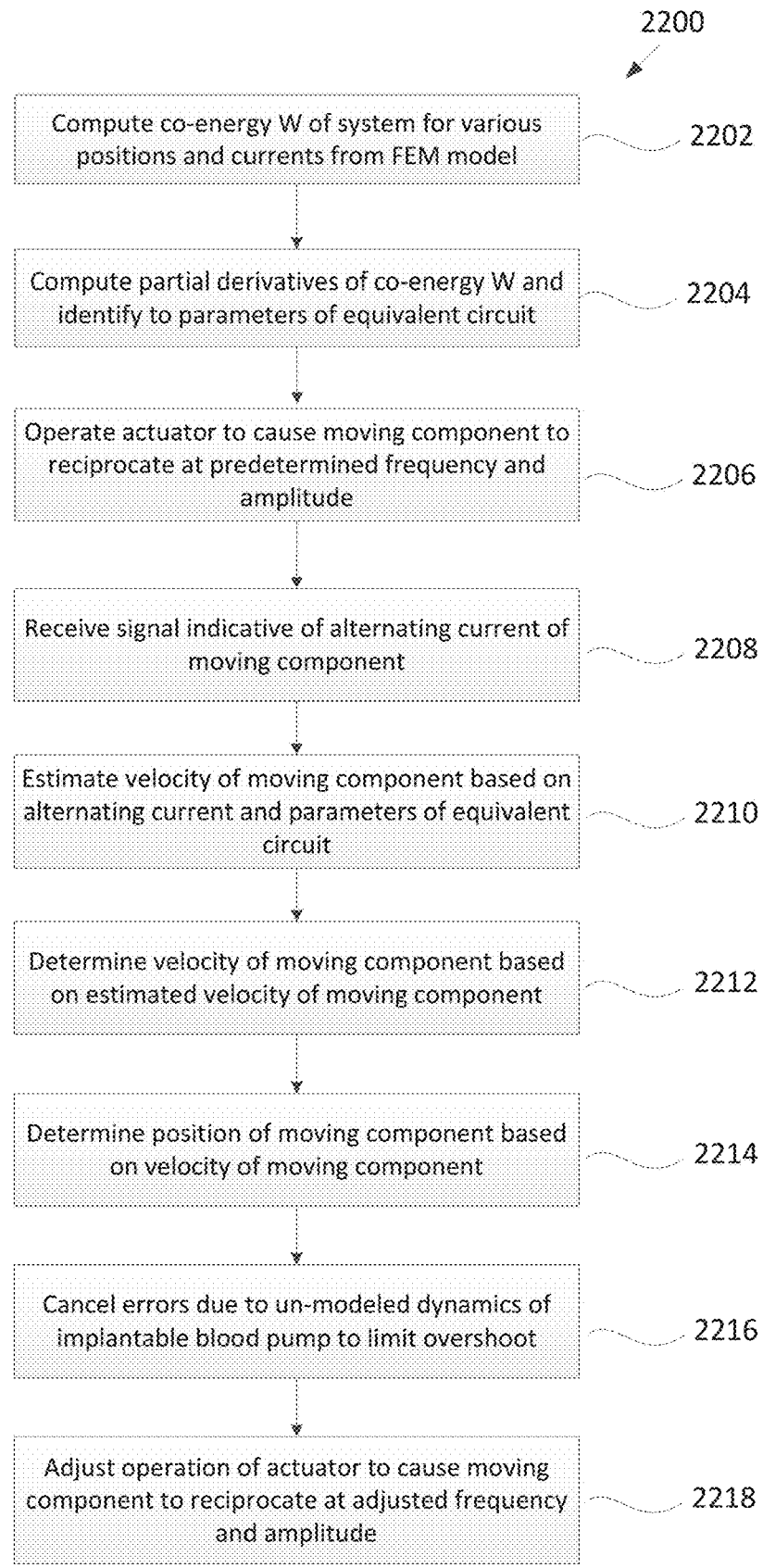
FIG. 22 is a flow chart illustrating steps of an exemplary method for controlling an implantable pump constructed in accordance with the principles of the present invention.
Figure 23:
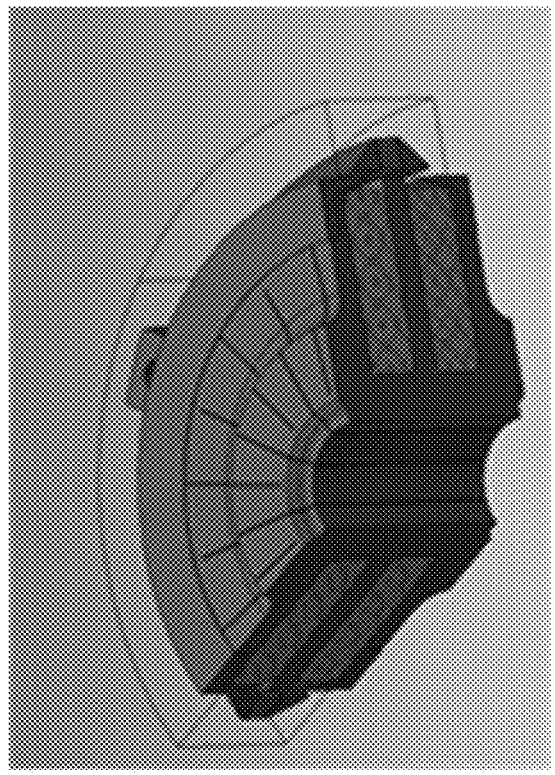
FIG. 23 is a FEM model of a subset of an actuator assembly of an implantable pump constructed in accordance with the principles of the present invention.
Figure 24A:
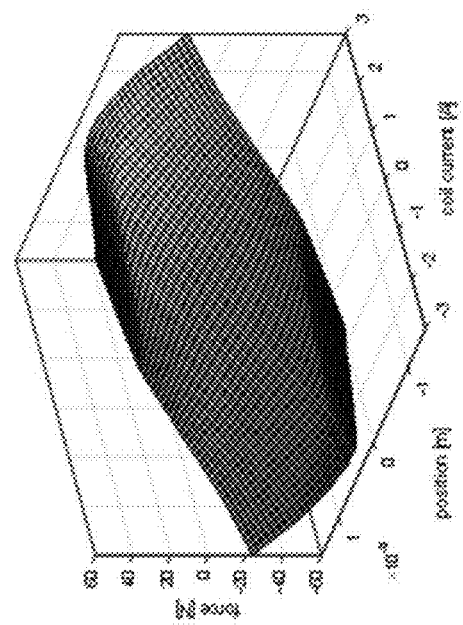
FIG. 24A displays co-energy as a function of magnetic ring position and coil current.

Referring now to FIG. 22, a flow chart illustrating steps of exemplary method 2200 for controlling an implantable pump constructed in accordance with the principles of the present invention. e.g., implantable pumps 20, 20", 20''', and 20"". First, a finite element method (FEM) model of an electromagnetic actuator. e.g., electromagnet assembly 91 and magnetic ring assembly 76, is transformed into a lumped parameters model represented by a system of ordinary differential equations (ODEs). The FEM model is set up by creating a subset of the actuator's geometry to save computing time as illustrated in FIG. 23. At step 2202, co-energy W of the implantable blood pump system is computed for various magnetic ring positions and coil currents, as illustrated in FIG. 24A. For example, co-energy W may be approximated by a lookup table that stores the output co-energy W values of the FEM model simulation.

At step 2204, partial derivatives of co-energy W are computed and identified to the parameters of an equivalent circuit which is expressed as:

$$V_{in}(t) = RI + L(x, I)\frac{dI}{dt} + E(x, I)\frac{dx}{dt}$$

where:

$$L(x, I) = \frac{\partial^2 W(x, I)}{\partial I^2}$$

$$E(x, I) = \frac{\partial^2 W}{\partial x \partial I}$$

The one degree-of-freedom motion equation of the magnetic ring of the implantable pump gives:

$$m\ddot{x}(t) = F_{mag}(x,I) + F_{springs}(x) + F_{membrane}(t)$$

where:

$$F_{mag} = \frac{\partial W(x, I)}{\partial x}$$

$$F_{springs} = ax^3 + bx$$

Figure 24B:
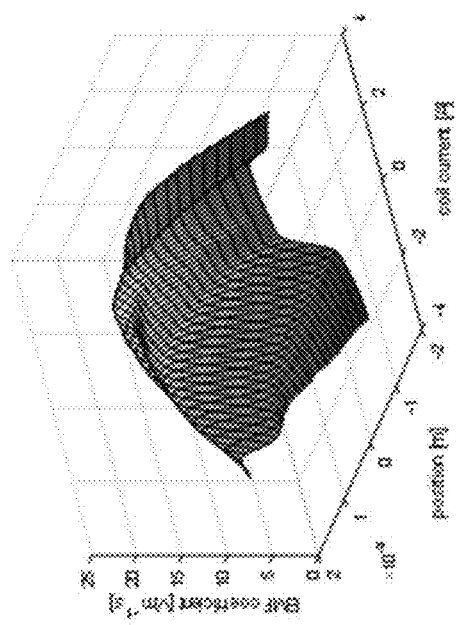
FIG. 24B displays force as a function of magnetic ring position and coil current, FIG. 24C displays circuit inductance of an equivalent circuit as a function of magnetic ring position and coil current, and FIG. 24D displays circuit EMF coefficient of an equivalent circuit as a function of magnetic ring position and coil current.
Figure 24C:
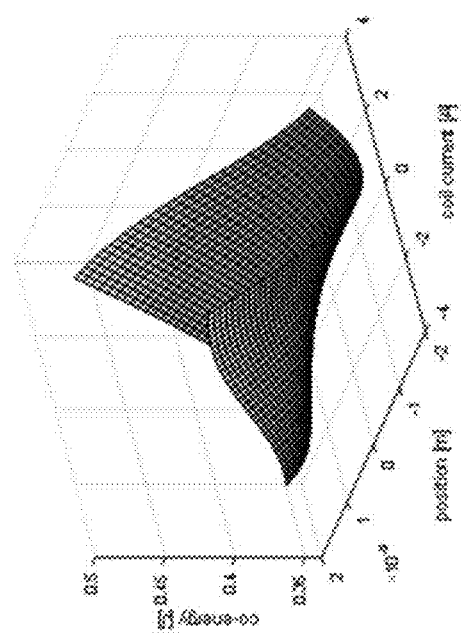
Figure 24D:
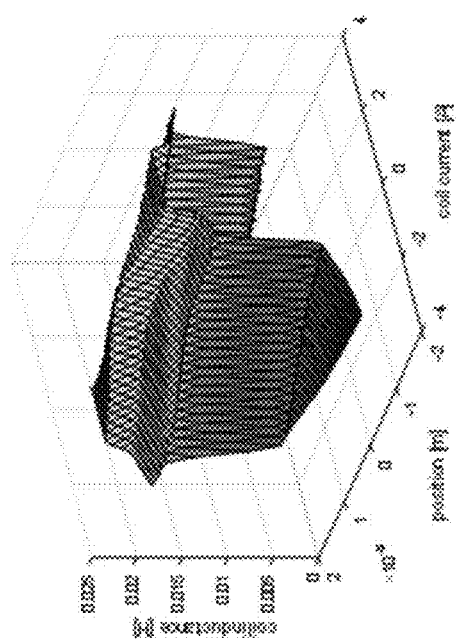
Figure 25:
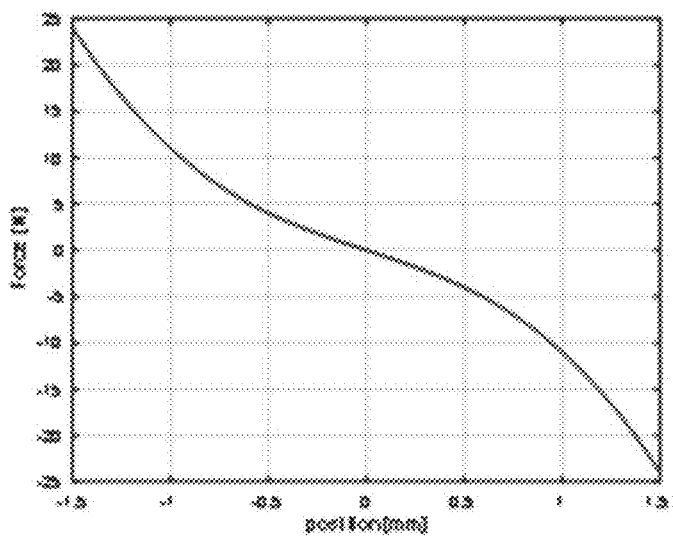
FIG. 25 is a graph illustrating spring reaction force of as a function of position of an implantable pump.
Figure 26:
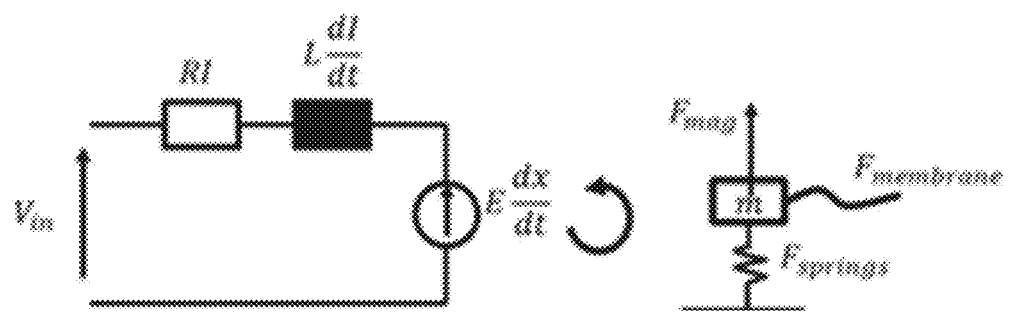
FIG. 26 is a schematic of the parameters of an equivalent circuit in accordance with the principles of the present invention.

$V_{in}$=input voltage
x=magnetic ring position
I=coil current
R=coil resistance
L=coil inductance
E=back EMF factor FIGS. 24B, 24C, and 24D illustrate the force derived from the co-energy W as a function of the magnetic ring's position and coil current, the equivalent circuit's inductance derived from the co-energy W as a function of the magnetic ring's position and coil current, and the equivalent circuit's EMF coefficient derived from the co-energy W as a function of the magnetic ring's position and coil current, respectively. FIG. 25 is a graph illustrating the relationship between spring reaction force and position of the magnetic ring of the implantable pump. FIG. 26 is a schematic representation of the parameters of the equivalent circuit and the one degree-of-freedom motion equation of the magnetic ring of the implantable pump described above.

Springs reaction force $F_{springs}$ is identified to a third-degree polynomial to take into account design-induced nonlinearities that are measured by the manufacturer of the electromagnetic actuator. Membrane force $F_{membrane}$ is supposed bounded and piecewise continuous. This vague description of the membrane force is motivated by the lack of sufficient knowledge of the fluid-structure interaction that takes place between pump's membrane and fluid, as well as the possibility to synthetize a controller that will not require more hypothesis of this force than what has been given.

At step 2206, the controller operates the electromagnetic actuator of the implantable pump to cause the moving component, e.g., magnetic ring assembly 76, to reciprocate at a predetermined stroke, e.g., frequency and amplitude. At step 2208, the controller receives a signal indicative of the alternating current of the system, e.g., coil current, from a current sensor positioned, for example, inside the power electronics of the implantable pump system.

Figure 27A:
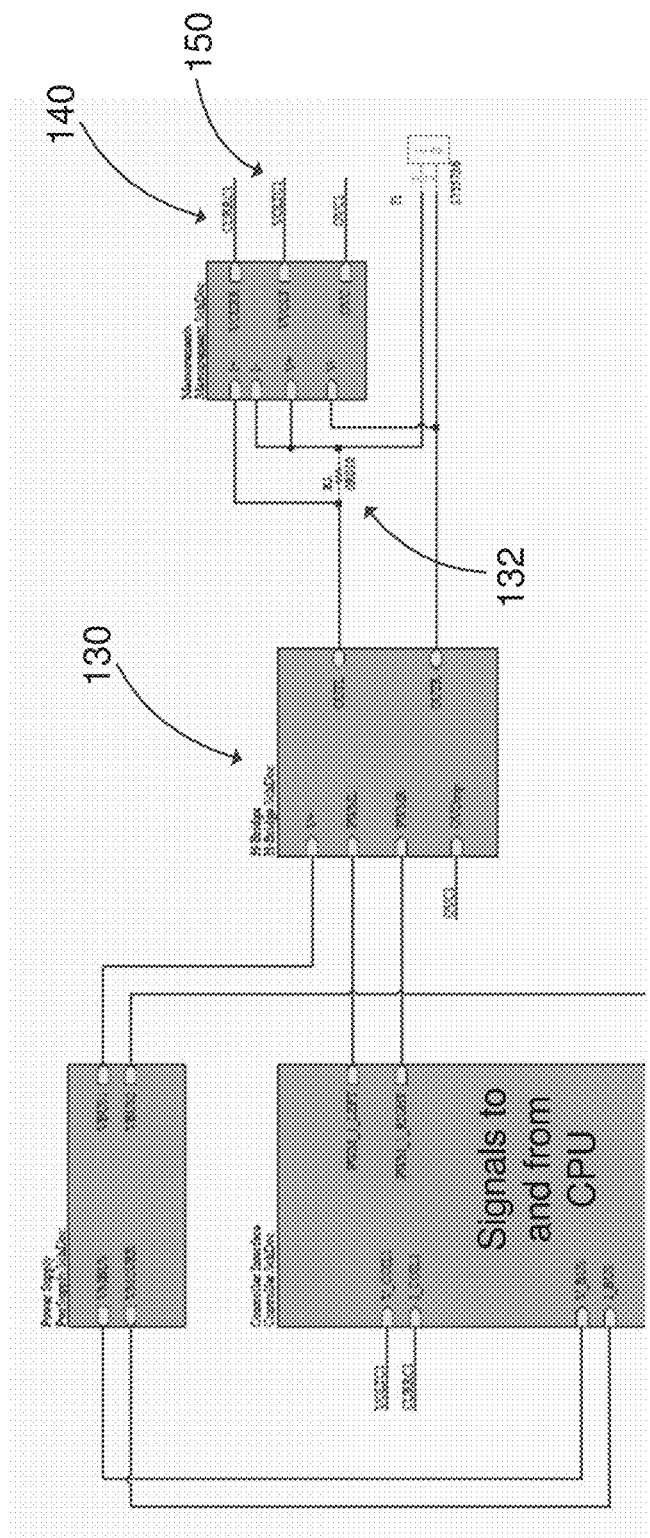
FIGS. 27A-27D is a schematic of the power electronics constructed in accordance with the principles of the present invention.
Figure 27B:
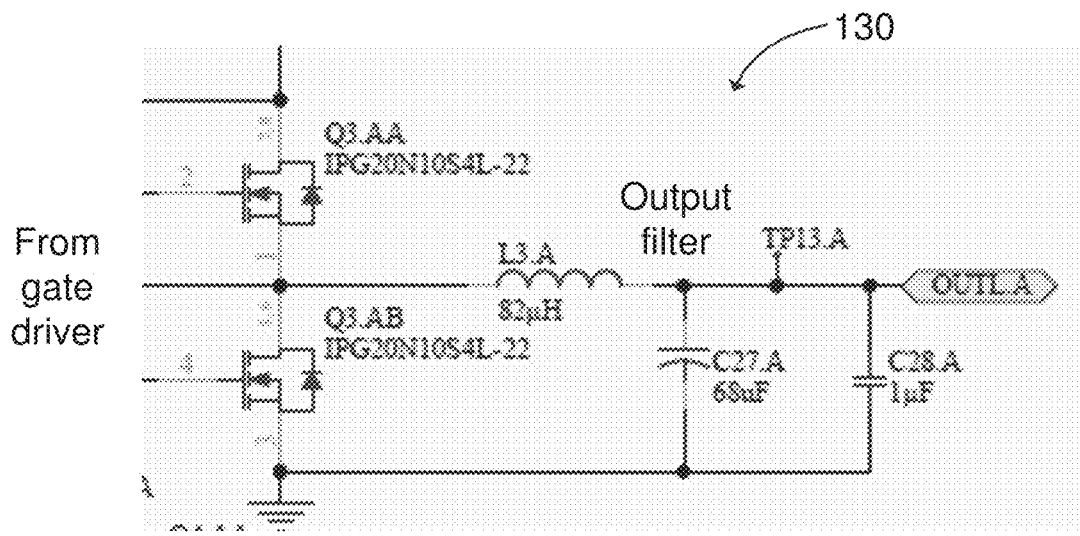

For example, as illustrated in FIG. 27A, the implantable blood pump, which can be considered an inductive load, may be driven with an H bridge configuration. As illustrated in schematic of the power electronics of FIG. 27A, the power electronics may include H bridge 130, shunt resistor 132, current sensor 140, and optional voltage sensor 150. The H bridge, illustrated in FIG. 27B, is driven to generate a certain voltage waveform, while powered from a power supply, e.g., battery 40, directly or through a DC/DC voltage converter. As will be understood by a person having ordinary skill in the art, the power electronics could include a single H bridge, with both coils in series or in parallel, or two H bridges, with one H bridge per coil.

Figure 27C:
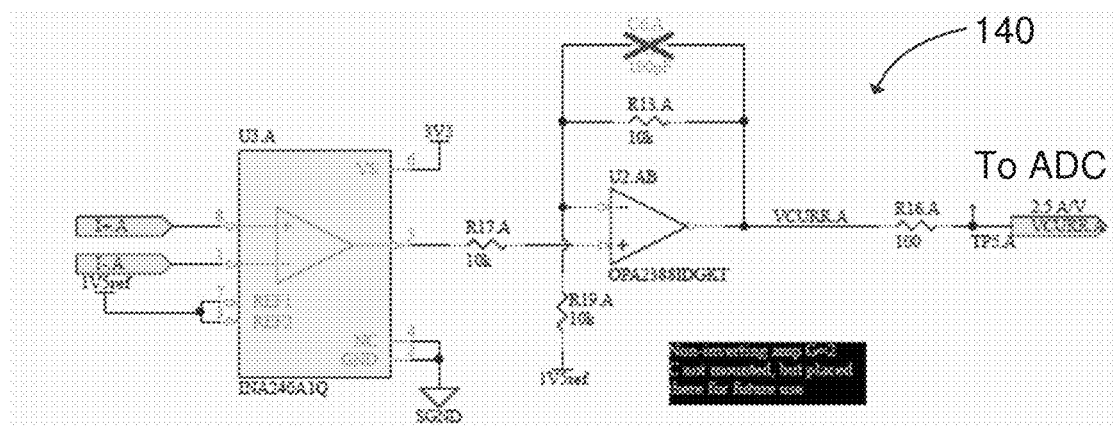
Figure 27D:
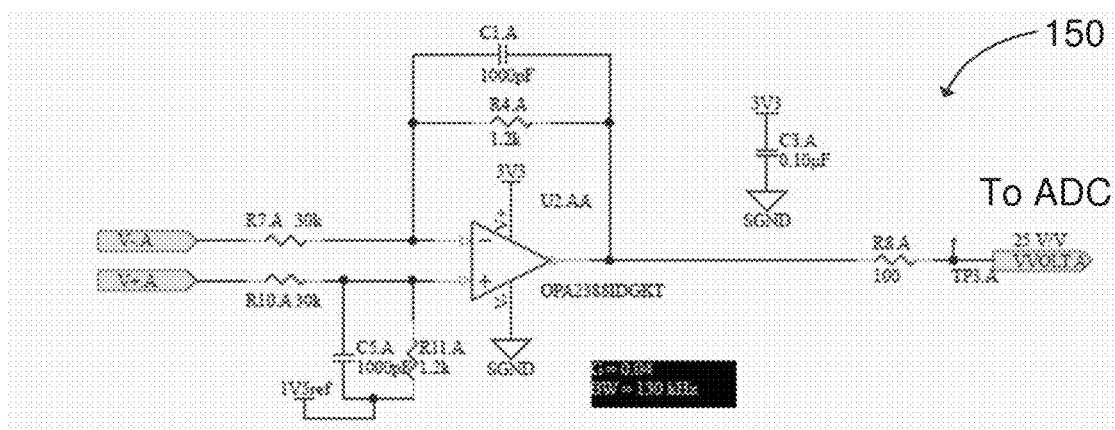
Figure 28:
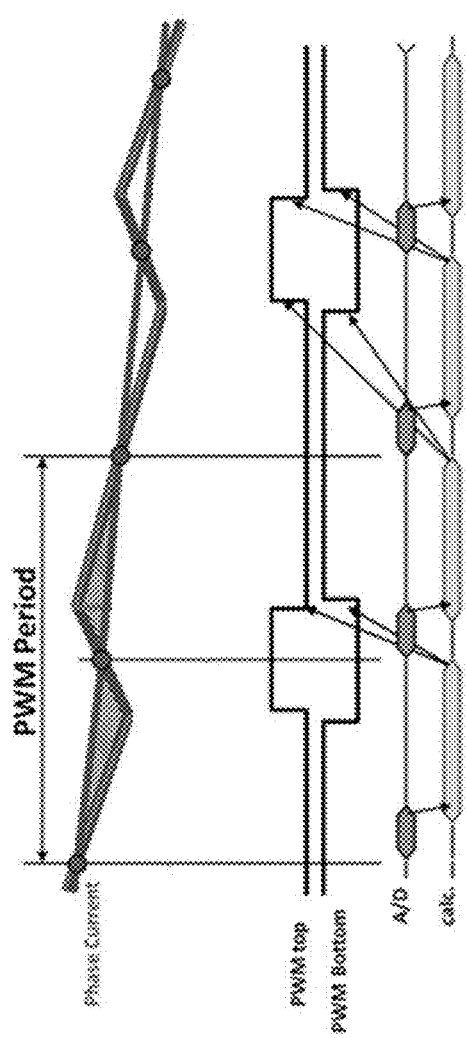
FIG. 28 illustrates ADC sampling for measuring current in accordance with the principles of the present invention.

FIG. 27C is a schematic of the current sensor for measuring the current of the actuator. FIG. 27D is a schematic of an optional voltage sensor for measuring the voltage of the actuator. The use of the voltage feedback is optional, given that the algorithm controls the H bridge, and therefore, knows the imposed voltage. As illustrated in FIG. 28. Analog to Digital Converter (ADC) sampling is synchronized with the middle point of the transistors' pulse-width modulation (PWM) signals to remove the transistors' switching glitch noise from both the current and voltage measurements. Accordingly, the current and/or pump voltage measurements are sent to the algorithm running on the controller, and the algorithm estimates the position of the actuator and determines the H bridge voltage required to impose a certain position oscillation.

Specifically, from the current measurement, the controller is able to control the excitation of the deformable membrane, e.g., membrane 97, while being robust to the almost un-modelled force of the deformable membrane $F_{membrane}$. Thus, the implantable pump system does not require position, velocity, or acceleration sensors. For example, the controller includes a position observer module that has two stages. During the first stage (step 2210), the position observer module estimates the velocity of the magnetic ring based on the alternating current measurement and the parameters of an equivalent circuit using the equation described above:

$$V_{in}(t) = RI + L(x, I)\frac{dI}{dt} + E, (x, I)\frac{dx}{dt}$$

For example, the estimated velocity may be expressed as:

$$\hat{\dot{x}} = \frac{1}{E(x, I)}\left(V_{in} - RI - L(x, I)\frac{dI}{dt}\right)$$

The derivative in of the above equation will make the estimation extremely sensitive to measurement noise if left as it is. To deal with this estimation problem a derivate estimator is developed:

$$\widehat{\frac{dI}{dt}}(t) = -\frac{6}{T^3}\int_{t-T}^{t}(T - 2\tau)I(t - \tau)d\tau$$

where T is the length of an integration window. This estimation is straightforward to implement as a discrete finite impulse response (FIR) filter by using the trapezoidal method:

$$\widehat{\frac{dI}{dt}}(kT_s) = -\frac{6}{(NT_s)^3}\sum_{i=0}^{N}w_i(NT_s - 2iT_s)I(kT_s - iT_s)d\tau$$

where N is an integer chosen so that $T=NT_s$, $$w_0 = w_N = \frac{T_s}{2}$$

and $w_i=T_s$, i=1, ... N-1.

Next, the second stage of the position observer module is implemented (step 2212), where the position observer module determines the velocity of the magnetic ring based on the estimated velocity calculated during step 2210. For example, it follows that, if $\tilde{x}$ and $\tilde{\dot{x}}$ are the observed position and velocity, the position observer module could be expressed as:

$$\begin{bmatrix}\tilde{\dot{x}}\\\tilde{\ddot{x}}\end{bmatrix} = A\begin{bmatrix}\tilde{x}\\\tilde{\dot{x}}\end{bmatrix} + \begin{bmatrix}0\\F(t)\end{bmatrix} + \begin{bmatrix}k_1\\k_2\end{bmatrix}(\hat{\dot{x}} - \tilde{\dot{x}})$$

where A is a constant square matrix regrouping the linear terms of the estimated velocity above and F(t) is the function regrouping the nonlinear elements, and $k_1$ and $k_2$, two gains to be chosen to guarantee:

$$\lim_{t\to\infty}\begin{bmatrix}x - \tilde{x}\\\dot{x} - \tilde{\dot{x}}\end{bmatrix} = 0$$

Figure 29:
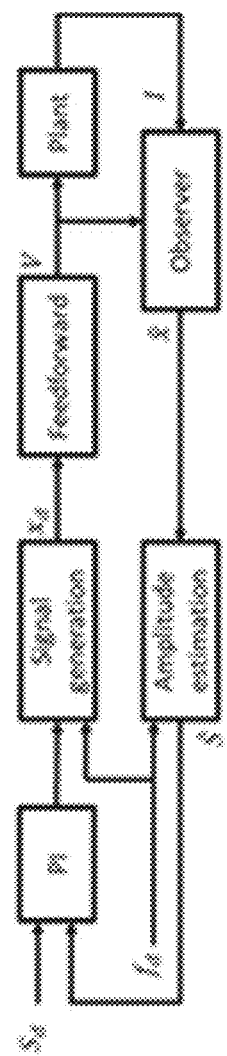
FIG. 29 is a diagram illustrating multistage control of a controller constructed in accordance with the principles of the present invention.

At step 2214, the position observer module of the controller determines the position of the magnetic ring based on the determined velocity above. Accordingly, from the observed position of the magnetic ring, the stroke controller will be able to set the excitation of the deformable membrane via the electromagnetic actuator to a desired frequency and amplitude, while limiting overshoot. Thus, at step 2216, the controller cancels errors due to un-modeled dynamics of the implantable pump to limit overshoot. For example, as illustrated in FIG. 29A, the controller may include a feedforward module and a PI controller module. The feedforward module takes as input the desired position $x_d$ at each time step to compute input voltage as:

$$V_{in} = RI_d + L\frac{dI_d}{t} + E\frac{dx_d}{dt}$$

-continued $$F_{mag}(x_d, I_d) = m\ddot{x}_d - F_{springs} - \alpha \frac{dx_d}{dt}$$

where $I_d$ can be computed as:

$$I_d = \Phi(x_d, F_{mag})$$

The reference signal $x_d$ is generated as:

$$x_d(t) = S(t)\sin(\varphi(t))$$

$$\varphi(t) = 2\pi f(t)$$

$$H(s) = \frac{k_f^3}{(s+k_f)^3} = \frac{S}{S_d}(s) = \frac{f}{f_d}(s)$$

where $k_f$ is a positive, real number that guarantee the stability of H(s).

Then, the remaining errors due to un-modeled dynamics are cancelled by PI controller module by adjusting the excitation signal. This could be implemented using various methods. For example, its instantaneous value could be directly modified, or alternatively, another method is to modify its amplitude, or both its amplitude and its instantaneous value, on different feedback loops as illustrated in FIG. 29B. If the amplitude modification is used, one way to estimate it is to define an amplitude estimator $\hat{S}(t)$ that is valid if x(t) is sufficiently close to a sinus function:

$$\hat{S}(t) = \sqrt{\hat{x}(t)^2 + \hat{x}\left(t - \frac{1}{4f}\right)^2}$$

At step 2218, the controller adjusts operation of the electromagnetic actuator to cause the magnetic ring to reciprocate at an adjusted frequency and/or amplitude, thereby causing the deformable membrane to produce an adjusted predetermined blood flow across the implantable pump.

To capture the variations of inductance and back EMF coefficient with magnetic ring's position and coil current, a recursive least square estimator is used by the controller.

The parameters R, L and E described above are unknown and slowly time varying. The variables $V_{in}$, l and x are piecewise continuous and bounded, and all equal to zero at t=0. The problem is set by integrating (1) over t:

$$I = \frac{1}{L}\int V_{in} + \frac{R}{L}\int I - + \frac{E}{L}x$$

which can be expressed as:

$$y = \Psi^T \theta$$

$$\Psi^T = \left[\int V_{in} \quad \int Ix\right]$$

$$\theta = \left[\frac{1}{L} \quad \frac{R}{L} \quad \frac{E}{L}\right]$$

For each sample n>0:

$$\hat{\theta}_n = \hat{\theta}_{n-1} + K_n(y_n - \hat{y}_n)$$

$$\hat{y}_n = \Psi_n^T \hat{\theta}_{n-1}$$

$$K_n = \Psi_n Q_n$$

$$Q_n = \frac{P_{n-1}}{\lambda + \Psi_n^T P_{n-1}\Psi_n}$$

$$P_n = \frac{1}{\lambda}\left(P_{n-1} - \frac{P_{n-1}\Psi_n \Psi_n^T P_{n-1}}{\lambda + \Psi_n^T P_{n-1}\Psi_n}\right)$$

where $\lambda$ is a forgetting factor chosen so $\lambda<1$, $P_0$ is the initial covariance matrix, and $\hat{\theta}_0$ is the initial estimate of the parameters.

The resulting estimation data is then fit to polynomials of appropriate degree that are to be used in the velocity estimator:

$$\hat{L}(x, I), \hat{E}(x, I) = [1 \; \ldots \; x^m]\begin{bmatrix} \alpha_{00} & \ldots & a_{0,n} \\ \vdots & \ddots & \vdots \\ a_{m,0} & \ldots & a_{m,n} \end{bmatrix}\begin{bmatrix} 1 \\ \vdots \\ I^n \end{bmatrix}$$

Experimental Results

A numerical model of the implantable pump and the controller was built under Matlab/Simulink to test the implementation of the controller and model parameters' identification. The actuator model is compared to measurement and adjusted accordingly. The springs' reaction force is measured by using a pull tester, which is also used to measure the magnetic force of the actuator by applying an arbitrary constant electric current on the electromagnetic coils of the actuator while measuring force. The back EMF coefficient was derived from the force measured at different electric currents and magnetic ring positions. Electric inductance and resistance may be estimated with a LRC meter when the magnetic ring's motion is blocked to cancel the effect of the back EMF. As LRC meters' input current is limited (<20 mA), inductance may only be estimated in this limited area. In general, the performances of the real actuator are reduced compared to the model (lower inductance, magnetic force and EMF). This may be due to an imperfect manufacturing process. e.g., the winding of the coils. The membrane force may be emulated by a viscous friction term that is a sensible first approximation:

$$F_{membrane}(t) = \mu(t)\dot{x}$$

With these verifications, the parameters' variations are identified and the controller structure is tested. In particular, different position observer implementations are compared to show the interest of using varying electric parameters instead of linear approximations.

Figure 30A:
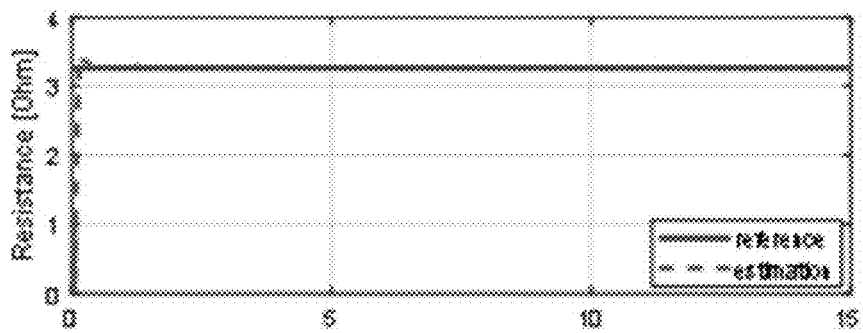
FIGS. 30A-30C illustrate identification of variations of resistance, inductance, and EMF coefficient, respectively, with magnetic ring position and coil current in accordance with the principles of the present invention.
Figure 30B:
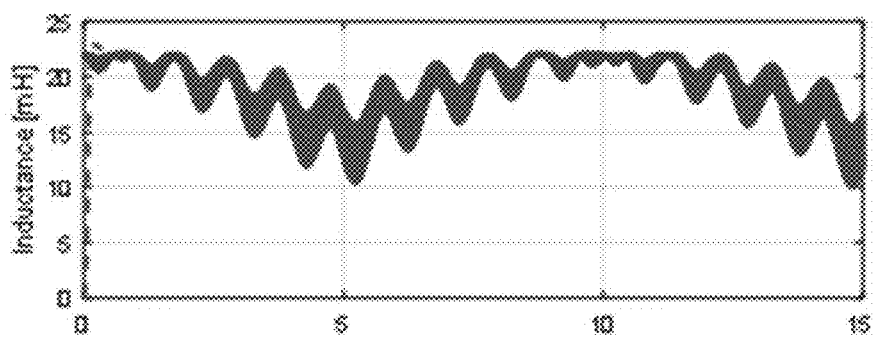
Figure 30C:
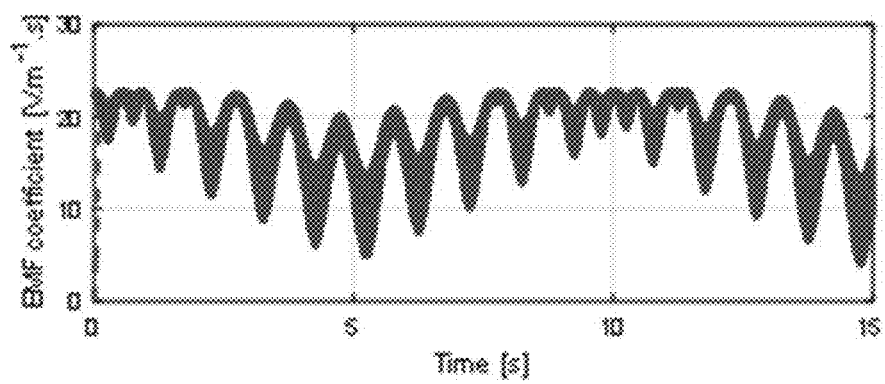

The results of the identification are shown in FIGS. 30A-30C. To guarantee a quick convergence, two excitation signals are applied to the actuator. A voltage excitation that contains a high frequency (500 Hz) square wave voltage makes the inductance's voltage to never be close to zero, and a low frequency (0.1 Hz) sinus component for the resistance's voltage reach every position. To ensure that back EMF is represented in the response, an external sinusoidal force is simulated at 50 Hz. To filter out high frequency variations as well as eventual noise, while capturing the low frequency variations of the parameters. λ is set to 0.999 via a trial-and-error approach. The recursive least square identification was run with different initial conditions. Measurement errors (noises, bias, gain) were simulated to verify that their effects would not hinder convergence and help to diagnostic future experimental issues. The RLS algorithm filters out high frequency noises very easily, but gain errors lead to over or underestimation of parameters while bias and low frequency noise increase estimation error over time.

Figure 31A:
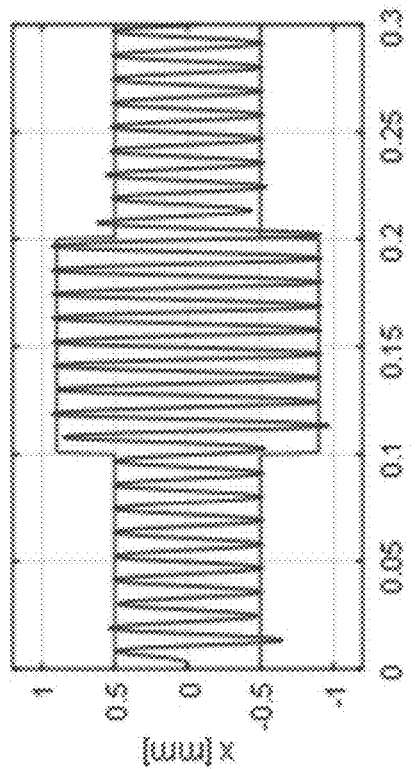
FIGS. 31A and 31B illustrate the system response to a desired stroke with respect to coil current and magnetic ring position, respectively.
Figure 31B:
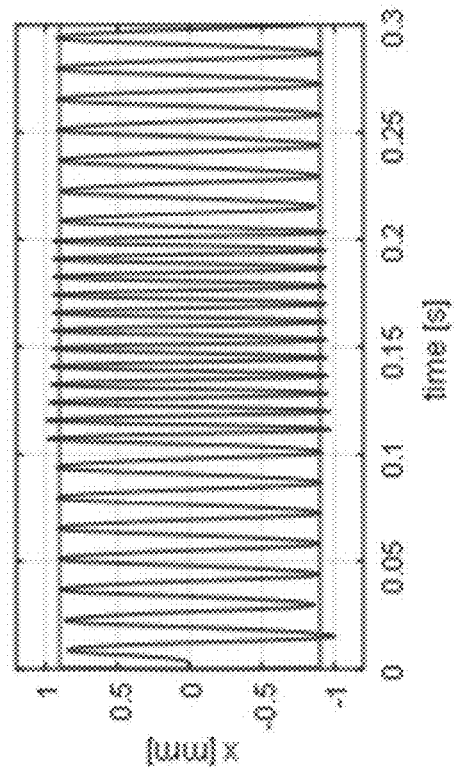

A discrete version of the controller is implemented on Simulink to emulate what would be done by compiling it on a hardware target. As the frequency response of the derivative estimator described above depends on the length of the integration window and the sampling rate, and the signals to derivate may have frequency up to 100 Hz. We set $T_s=2\times 10^{-5}$ s and N=6 (i.e., integration window of $1.2\times 10^{-4}$ s), which is a good trade between noise attenuation and performance. FIGS. 31A and 31B shows the response of the actuator from startup at t=0 s to a nominal constant operation point, i.e., a constant amplitude and frequency. Current and magnetic ring position are both reasonably sinusoidal, and after a transition period, the amplitude of position reaches the desired amplitude, and the position observer module output keeps track of the variation of position.

Figure 32A:
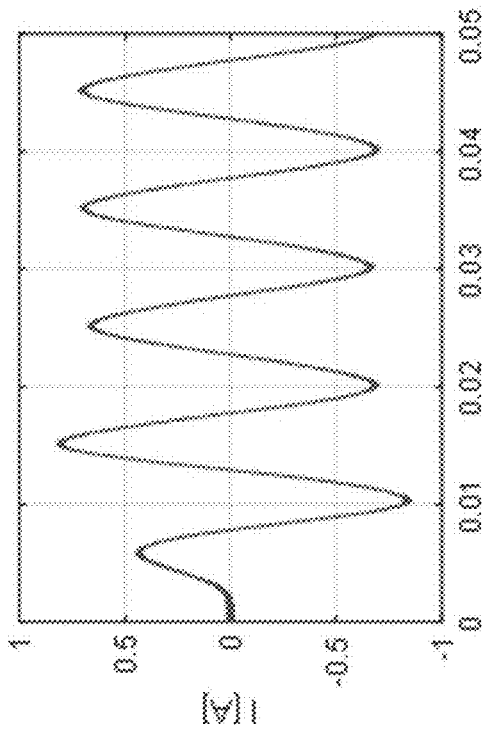
FIGS. 32A and 32B illustrate the system response to change of operation points with respect to amplitude and frequency, respectively.
Figure 32B:
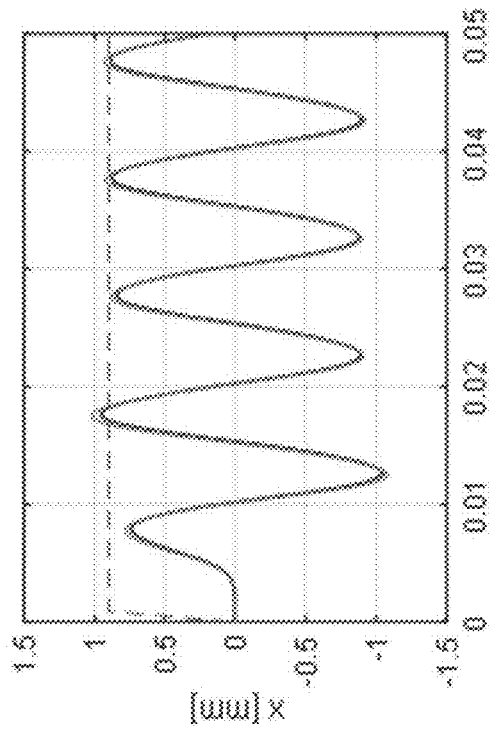
Figure 33B:
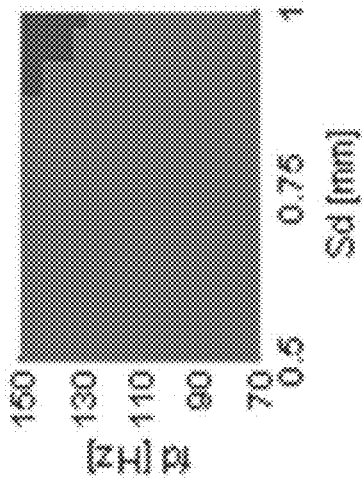
FIGS. 33A-33D illustrate stroke output error maps of the system in accordance with the principles of the present invention.
Figure 33D:
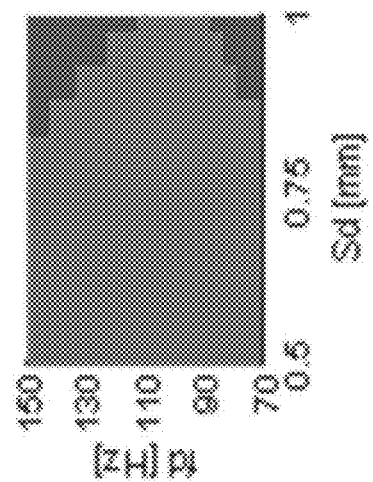
Figure 33A:
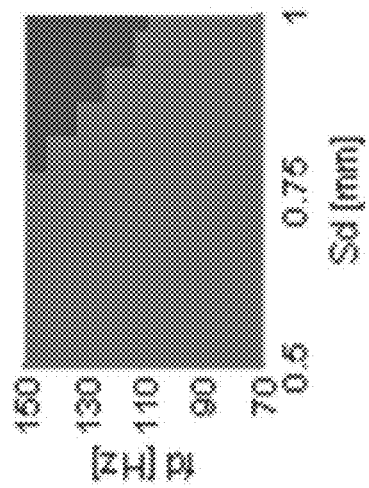
Figure 33C:
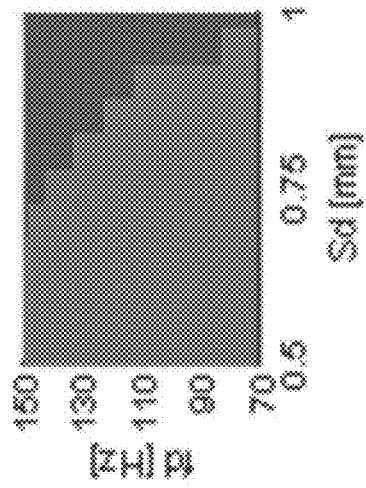

FIGS. 32A and 32B shows two cases of change of operation points: a change of frequency and a change of stroke, which are two ways to increase or decrease blood flow through by the pump. As shown in FIGS. 32A and 32B, overshoots appear during the change of stroke. If not kept below a safe level, the overshoots could create overstress that could damage the membrane and the springs. Overshoot may be avoided by making the desired stroke signal change smoother.

FIGS. 33A-33D is a comparison between 4 position observer modules which are different through their first stage. In each case, inductance and back EMF are implemented as constant approximation and as functions. As the controller must maintain stroke over a wide range of strokes and frequencies, and as different reaction forces of the membrane are unknown, combinations of those three parameters must be tested to evaluate the performance of the controller. To do so the variation of the membrane force is emulated according to flow and pressure inside the pump head by varying μ, and an error variable e is created that is evaluated over a range of strokes, frequency and μ:

$$e(S_d, f_d) = \max_{\mu}(|S_d - 0.5(\max x - \min x)|)$$

where max x & min x are computed from one period of oscillation. This formulation of e can be compared to a maximal admissible error ε: every operation point $[S_d, f_d]$ which presents e<ε can be reached safely (stroke will be maintained to deliver the required flow without the risk of damaging the device by an overshoot). With this performance indicator, it is observed that taking into account the variations of the inductance and back EMF in the velocity estimator results in an increase of the operation range of the stroke controller.

Referring now to FIG. 34A, an exemplary embodiment of the pump assembly of the present invention is described. The pump assembly is similar to the pump assembly described above with respect in FIG. 15A, in which similar components are identified with like numbers. Membrane assembly 202 is similar to membrane assembly 82' in that it includes skirt 203 similar to skirt 115 coupled to membrane 204 similar to membrane 97'. Skirt 203 illustratively includes first portion 205 similar to first portion 115a and second portion 206 similar to second portion 115b. First portion 205 of skirt 203 extends upward within delivery channel 207, similar to delivery channel 100' toward inlet 208 similar to inlet 21' in a first direction, e.g., parallel to the longitudinal axis of actuator assembly 217, stator assembly 211 and/or to the central axis of pump housing 200. Second portion 206 of skirt 203 curves toward outlet 209 similar to outlet 23' such that second portion 206 is coupled to membrane 204 so that membrane 204 is oriented in a second direction. e.g., perpendicular to first portion 205 of skirt 203. For example, skirt 203 may have a J-shaped cross-section, such that first portion 205 forms a cylindrical-shaped ring about stator assembly 211, and second portion 206 has a predetermined radius of curvature which allows blood to flow smoothly from delivery channel 207 across skirt 203 into delivery channel 214, similar to delivery channel 100a, and delivery channel 219, similar to delivery channel 100b. From delivery channel 214 blood flows into flow channel 213 and from delivery channel 219 blood flows in flow channel 212. In this manner delivery channel 207 reduces flow recirculation and improves hydraulic power generated for a given frequency while minimizing blood damage. In addition, the J-shape of skirt 203 may optionally be stiffer than a planar rigid membrane ring, thereby reducing flexing and fatigue as the blood moves across membrane 204.

Pump housing 200 may be the same or similar to pump housing 27. Skirt 203 may be coupled to moving assembly 215 (e.g., via one or more post 216, which may be elastic or rigid). Moving assembly 215 may be similar to magnetic ring assembly 76' and thus may move up and down relative to actuator assembly 217 which may include stator assembly 211 and magnetic assembly 218. As moving assembly 215 moves up and down, the movement is translated to skirt 203 and membrane 204. When the moving assembly travels a certain distance upward or downward, membrane assembly 202 may travel the same distance or may travel a proportional distance. For example, when moving assembly 215 travels 2 mm, membrane assembly 202 may also travel 2 mm in the same direction. Similarly, the frequency at which moving assembly 215 moves up and down may be the same frequency at which membrane assembly 202 travels up and down.

Moving assembly 215 may include at least one magnet 225 that may extend continuously within moving assembly or may include multiple discrete segments. Moving assembly 215 may further include bearing portion 223 and bearing portion 224 disposed on an exterior wall of moving assembly 215. Bearing portion 223 and bearing portion 224 may, together with bearing portion 226 on actuator assembly 217, form bearing 227. Bearing 227 may be a hydrodynamic or thin-film bearing, for example. Bearing portion 223, bearing portion 224, and/or bearing portion 226 may be designed to reduce friction between moving assembly 215 and actuator assembly 217 and otherwise resist abrasion. In one example, bearing portion 223, bearing portion 224, and/or bearing portion 226 may be a ceramic, such as such as Yttria-stabilized tetragonal zirconia polycrystal (Y-TZP) or zirconium-toughen alumina (ZTA), engineered plastics, such as poly-ether-ether-ketone (PEEK), poly-ether-ketone-ketone (PEKK) or Delrin, metals treated with low friction, wear-resistant coatings, such as diamond-like carbon (DLC) or titanium nitride, or any other similar low friction material. For example, bearing portion 223, bearing portion 224, and/or bearing portion 226 may form bearing pads on moving assembly 215 and actuator assembly 217, respectively.

Blood may enter from the left ventricle through inlet cannula 228 and flow downward along the pump assembly into delivery channel 207. The blood may move into a vertical portion of delivery channel 207 in the area between pump housing 200 and actuator assembly 217. As shown in FIG. 34A, skirt 203 divides delivery channel into upper delivery channel 214 and lower delivery channel 219 such that blood flow through delivery channel 207 is divided into upper flow channel 213 via upper delivery channel 214 and lower flow channel 212 via lower delivery channel 219, wherein flow channels 213 and 212 are separated by membrane 204. As depicted in FIG. 34A, blood flow through a pump having a J-shaped skirt may be distributed across both the upper and lower sides of the flexible membrane at a desired ratio and ultimately out outlet 209.

As moving assembly 215 moves linearly up and down with respect to actuator assembly 217, blood introduced at inlet 208 may flow between moving assembly 215 and actuator assembly 217 and thus may flow between moving assembly 215 and actuator assembly 217. As moving assembly 215 moves up and down, a pressure may build up between moving assembly 215 and actuator assembly 217, generating an opposing pressure force that acts upon an interior wall of moving assembly 215 and an exterior wall of stator assembly 217, such that moving assembly 215 is forced a certain distance away from stator assembly 217. The opposing force thus offsets and centers moving assembly 215 with respect actuator assembly 217. As moving assembly 215 moves linearly up and down, a high pressure force is generated between bearing portion 223 and bearing portion 224 and bearing portion 226 such that blood and/or plasma positioned between bearing portion 223 and bearing portion 224 and bearing portion 226 may experience shear-thinning causing cells to be excluded from the high pressure area. As a result, the viscosity of the blood between moving assembly 215 and actuator assembly 217 may be between 1.0 to 5.5 cp or 1.3 to 1.7 cP, for example. As blood cells may escape a gap between moving assembly 215 and actuator assembly 217, blood damage is likely to be reduced or eliminated.

As shown in FIG. 34A, magnetic assembly 218 may involve one or more electromagnetic (e.g., coils 77 and 78) that may be made of any electrically conductive metallic material such as copper and further may comprise of one or more smaller metallic wires wound into a coil. In the example illustrated in FIG. 34A, magnetic assembly 218 involves two distinct coils that may have the same or similar functionality as coils 77 and 78 described above with respect to FIGS. 8 and 9. Alternatively, magnetic assembly 218 may involve a single coil, three distinct coils or four or more coils.

As explained above with respect to coils 77 and 78, the electromagnetic coils may be individually activated by controller applying an electrical signal; thus, inducing current in the electromagnetic coils and generating a magnetic field surrounding the electromagnetic coils. The direction of the current in the electromagnetic coils and the polarity of magnet 225 of moving assembly 215 may be configured such that the first electromagnetic coil magnetically attracts or repels magnet 225 as desired. Similarly, a magnetic field may be created in the second electromagnetic coil by introducing a current in the second electromagnetic coil to attract or repel magnet 225 as desired. As also explained above, electromagnetic coils may be energized separately, or alternatively, may be connected in series to cause the electromagnetic coils to be activated simultaneously. In this configuration, a first magnetic coil may be configured to experience a current flow direction opposite that of the second electromagnetic coil. Accordingly, when current is induced to a first electromagnetic coil of the moving assembly to attract the moving assembly, the same current applied to the second electromagnetic coil may induce a current that causes the second electromagnetic coil to repel the moving assembly. Similarly, when current is induced to the second electromagnetic coil to attract the moving assembly, the current applied to the first electromagnetic coil may cause the first electromagnetic coil to repel the moving assembly. In this manner, the electromagnetic coils work together to cause deflection of the moving assembly.

By manipulating the timing and intensity of the electrical signals applied to the electromagnetic coils, the frequency at which moving assembly reciprocates up and down may be altered. For example, by alternating the current induced in the electromagnetic coils more frequently, the moving assembly may be caused to cycle up and down more times in a given period. By modifying the current, the magnetic force generated may be modified.

Implantable pump 201 may include resistance magnet 221 and resistance magnet 222 which may be coupled to actuator assembly 217 and positioned above and below moving assembly 215 and magnet 215. Resistance magnet 221 and resistance magnet 222 may be arranged and/or oriented such that each of resistance magnet 221 and resistance magnet 222 exert an opposing magnetic force against magnet 225 and thus moving assembly 215. For example, the north pole of resistance magnet 221 may be closest in proximity to the north pole of magnet 225 and the south pole of magnet 225 may be closest in proximity to the south pole of resistance magnet 222. Accordingly, resistance magnet 221 and resistance magnet 222 may repel magnet 225. As magnet 225 moves upward (e.g., as it is attracted to the first electromagnetic coil), the opposing force of resistance magnet 221 may increase. The same is true with respect to resistance magnet 222 as magnet 225 moves downward toward the second electromagnetic coil. In this arrangement, resistance magnet 221 and resistance magnet 222 may equally oppose magnet 225 causing magnet 225 to find a neutral position between resistance magnet 221 and resistance magnet 222. Accordingly, resistance magnet 221 and resistance magnet 222 may restrain moving assembly 215 with respect to linear movement and bearing 227 may restrain moving assembly 215 with respect to lateral movement. It is understood that resistance magnet 221 and/or resistance magnet 222 could be disposed on or coupled to other portions of implantable pump 201 (e.g., pump housing 200). It is understood that size, proximity and proportions the components in FIG. 34A may vary and that the system illustrated may not be to scale. For example, resistance magnets 221 and 222 may be significantly large than those shown in FIG. 34A.

Referring now to FIG. 34B, moving assembly 230, actuator assembly 217, magnetic assembly 218, skirt 203, post 216 and membrane 204 are illustrated. As explained above, actuator assembly 217 may include resistance magnet 221 and resistance magnet 222 as well bearing portion 226. Moving assembly 230 is similar to moving assembly 215 except that moving assembly 230 may be tapered an on an interior wall in fluid communication with actuator assembly 217. Specifically, bearing portion 223 and bearing portion 224 may be tapered such that channel 231 extending between moving assembly 215 and actuator assembly 217 may be wider at the top and bottom of channel 231. As moving assembly 230 moves up and down, the tapered configuration shown in FIG. 34B may result in a higher pressure in channel 231 than would occur for a non-tapered configuration (e.g., moving assembly 251 shown in FIG. 36). While magnetic assembly 218 may include a first electromechanical coil and a second electromechanical coil, it is understood only one electromechanical coil or more than two electromechanical coils (e.g., three electromechanical coils) may be used.

As shown in FIG. 34B, magnet 225 may have a north pole near the top of magnet 225 and a south pole near the bottom of magnet 225. A current in coil 77 of magnetic assembly 218 may be induced such that the north pole of magnet 225 is repelled from coil 77. Further, a current in coil 78 may be induced such that the south port of magnet 225 is attracted to coil 78. As explained above, coils 77 and 78 may be independently activated and may generate magnetic forces of different polarities. It is understood that the current induced in coils 77 and 78 may be reversed to attract magnet 225 toward coil 77. By alternating the direction of the current in coils 77 and 78, magnet 225 and thus moving assembly 230 may be selectively moved up and down. Alternatively, only one of coil 77 or coil 78 may be activated at a time. A mechanical spring may optionally be coupled to moving assembly 230 to restrict moving assembly 230 within a certain range of motion and/or return moving assembly 230 to a neutral position.

Referring now to FIG. 35A-B, moving assembly 241, similar to moving assembly 215, and actuator assembly 217 of implantable pump 201 are illustrated. FIG. 35B is a detailed view of FIG. 35A, showing channel 244 and bearing portion 243 and bearing portion 226 forming bearing 242. Bearing 242 is similar to bearing 227 but involves bearing portion 243 which extends the length of actuator assembly 217. Accordingly, bearing portion 243 and bearing portion 226 extend the entire length of bearing channel 244. The extended length of bearing portion 243 may improve the functionality of bearing 242 by reducing friction between moving assembly 241 and actuator assembly 217. While magnetic assembly 218 may include a first electromechanical coil and a second electromechanical coil, it is understood only one electromechanical coil or more than two electromechanical coils (e.g., three electromechanical coils) may be used.

Referring now to FIG. 35C, a configuration similar to that shown in FIGS. 35A-B is illustrated, except that bearing portion 243 and bearing portion 226 may be reduced or non-existent in an area between top portion 249 and bottom portion 248 of bearing portion 243 and top portion 246 and bottom portion 247 of bearing portion 226. Only top portion 249 of bearing portion 243 and top portion 246 of bearing portion 226 may make contact and only bottom portion 248 of bearing portion 243 and bottom portion 247 of bearing portion 226 may make contact.

Referring now to FIG. 36, moving assembly 251, actuator assembly 252, magnetic assembly 253, skirt 203, post 216 and membrane 204 are illustrated. Actuator assembly 252 may include magnet assembly 253 and stator assembly 254, which may be similar to stator assembly 217. Magnet assembly 253 may include coil 256, coil 257, and coil 258 which may each be similar to coils 77 and 78. Alternatively, coil 257 may be a permanent magnet. Actuator assembly 252 may further include bearing portion 259 on an outer wall of actuator assembly 252, similar to bearing portion 226. Moving assembly 251 may include magnet 261 and magnet 262 which may be equally spaced apart and set a certain distance from a center point of moving assembly 251. Magnet 261 and magnet 262 may have a polarity oriented in the same direction. Moving assembly 251 may further include bearing portion 263, similar to bearing portion 243, positioned on interior wall of moving portion 251 and in fluid communication with bearing portion 259. Bearing portion 263 and bearing portion 259 may together form bearing 264.

Magnet 261 and magnet 262 may be positioned relative to actuator assembly 252, and have an equal magnetic intensity such that magnet 261 and magnet 262 are equally attracted to coil 257 and may assume a neutral position with respect to coil 257, barring other electromagnetic forces. Coil 256 and coil 258 may be selectively and/or individually actuated. A current may be induced in coil 256 and 258 to cause an electromagnetic force in a first direction. The current may be reversed to cause an electromagnetic force in a second direction, opposite the first direction. It is understood that coil 256 and coil 258 may have a current in the same direction or in opposite directions. Coil 257 may have the same functionality as coils 256 and 258 or may exhibit functionality similar to a permanent magnet.

As shown in FIG. 36, magnet 261 and magnet 262 may each have a north pole near the top of each respective magnet and a south pole near the bottom. Current in coil 256 may be induced in to attract magnet 261. For example, coil 256 may attract a north pole positioned near the bottom of coil 256. Further, current in coil 258 may be induced to repel magnet 262. For example, coil 258 may repel a south pole positioned near the top of coil 258. In this manner, coil 256 may attract moving assembly 251 in a upward direction and/or coil 258 may repel moving assembly 251 in an upward direction. Coil 257 may simultaneously exert an attraction force on both magnet 261 and magnet 262. For example, coil 257 may be a coil or a permanent magnet that attracts a south pole near the top of coil 257 and attracts a north pole near the bottom of coil 257. In the configuration shown in FIG. 36, coils 256 and 258 may attract moving assembly 251 upward and coil 257 may resist upward movement of moving assembly 251 in favor of a neutral position of moving assembly 251 between coil 256 and coil 258. In this manner, coil 257 may exert a force on moving assembly 251 similar to a spring force to bias moving assembly 251 to return to a neutral position adjacent to coil 257, between coils 256 and 258. As the electromagnetic force exerted by coil 256 and 258 is reduced and/or terminated, moving assembly may return to a neutral position adjacent to coil 257.

Alternatively, current induced in coil 256 and coil 258 may be reversed. Specifically, the current induced in coil 256 may be reversed such that a magnetic north pole may be repelled from the coil 256 near the bottom of coil 256. Further, the current induced in coil 258 may be reversed such that a south pole may be attracted near the top of coil 258. Coil 257 may remain constant and thus may attract a south pole near the top of coil 257 and attract a north pole near the bottom of pole 257. In this configuration, coils 256 and 258 may force moving assembly 251 downward and coil 257 may resist downward movement in favor of a neutral position between coil 256 and coil 258. As the electromagnetic force exerted by coil 256 and 258 is reduced and/or terminated, moving assembly may return to a neutral position adjacent to coil 257.

By alternating activation of coils 256 and 258 and/or reversing current in coils 256 and 258, moving assembly 251 may be caused to move up and down in a reciprocating fashion. Coil 257 may restrict the range of motion of moving assembly 251 and may cause moving assembly 251 to return to a neutral position adjacent coil 257. For example, when coils 256 and 258 are deactivated, moving assembly 251 may return to a neutral position adjacent coil 257. While moving assembly 251 is illustrated as having a rectangular shape, it is understood that moving assembly 251 may have any other shape, including but not limited to the shape of moving assembly 230 and the shape of moving assembly 215. Moving assembly 251, bearing portion 263 and/or bearing portion 259 may include one or more axially orientated slots to increase blood washing of the surfaces of the bearing portion 263 and/or bearing portion 259.

Figure 37B:
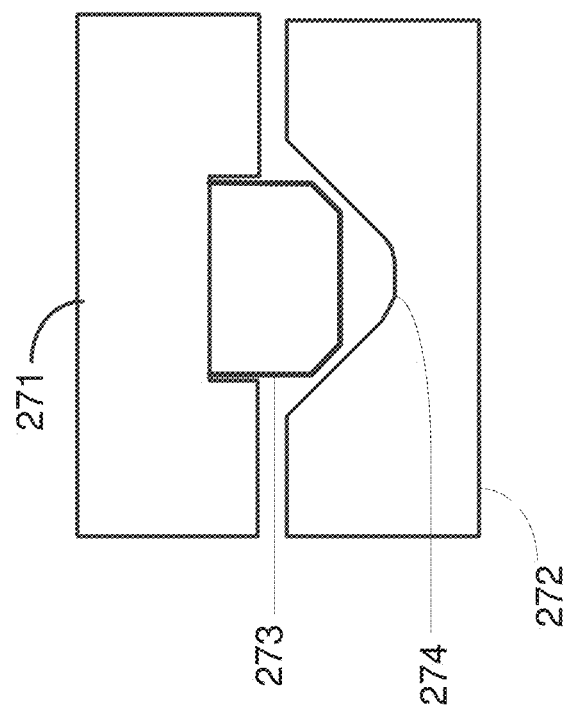
FIGS. 37A-37B illustrate the moving assembly and actuator assembly with rails on the moving assembly in accordance with the principles of the present invention.
Figure 37A:
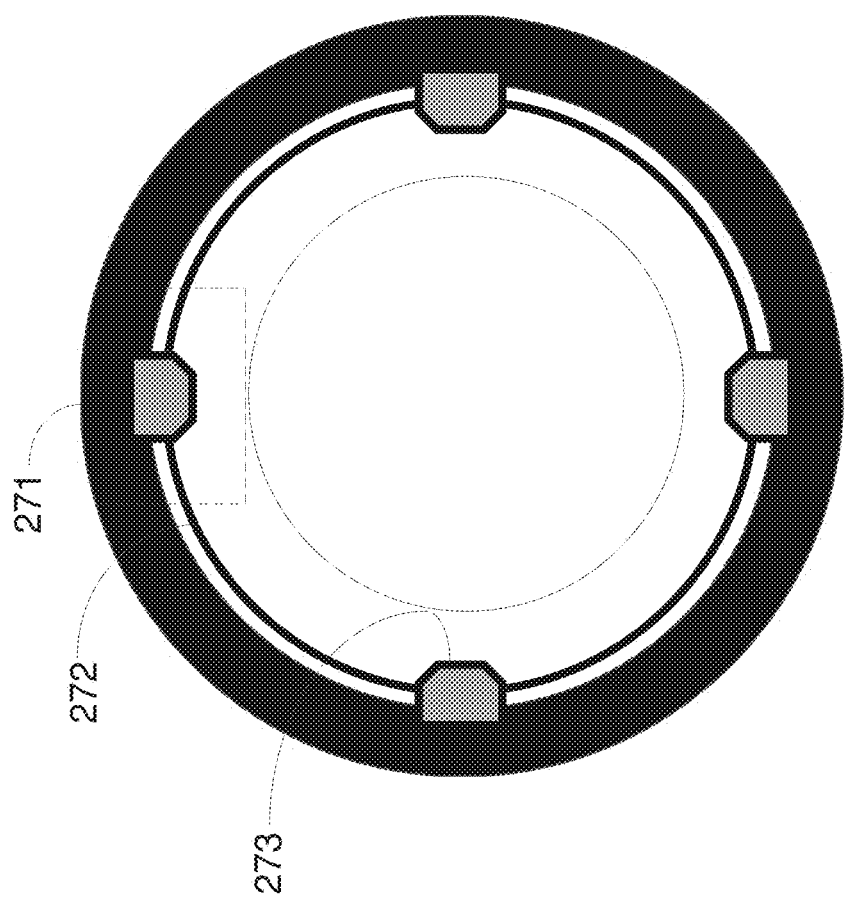

Referring now to FIGS. 37A-B, moving assembly 271 and actuator assembly 272 are illustrated. FIG. 37B is a close up view of a portion of FIG. 37A. Moving assembly 271 is substantially similar to moving assembly 251 and actuator assembly 272 is substantially similar to actuator assembly 252. As shown in FIG. 37A-B, moving assembly 271 may be coupled to or otherwise incorporate rail 273. Actuator assembly 272, at an exterior surface of actuator assembly 272, may include indentation 274 sized and configured to receive rail 273 or a portion thereof and may guide rail 273 along actuator assembly 272. Rail 273 and/or indentation 274 may extend the length of moving assembly 271 and/or actuator assembly 272, respectively. Rail 273 is preferably positioned parallel to a central axis of moving assembly 271 and/or parallel to the range of motion of moving assembly 271. As shown in FIG. 37A, moving assembly 271 may include 4 rails 273 that are equally spaced apart. Alternatively, any number of rails 273 may be incorporated on moving assembly 271 that may or may not be equally spaced apart. For example, 3-12 rails mays be incorporated on moving assembly 271. Rail 273 and/or indentation 274 may be or incorporate a ceramic, such as Yttria-stabilized tetragonal zirconia polycrystal (Y-TZP) or zirconium-toughen alumina (ZTA), engineered plastics, such as poly-ether-ether-ketone (PEEK), poly-ether-ketone-ketone (PEKK) or Delrin, metals treated with low friction, wear-resistant coatings, such as diamond-like carbon (DLC) or titanium nitride, or similar low friction materials to reduce friction between rail 273 and indentation 274, if rail 273 comes into contact with indentation 274. Rail 273 and indentation 274 may function as a bearing or a portion of a bearing, such as a hydrodynamic or thin film bearing.

Figure 38B:
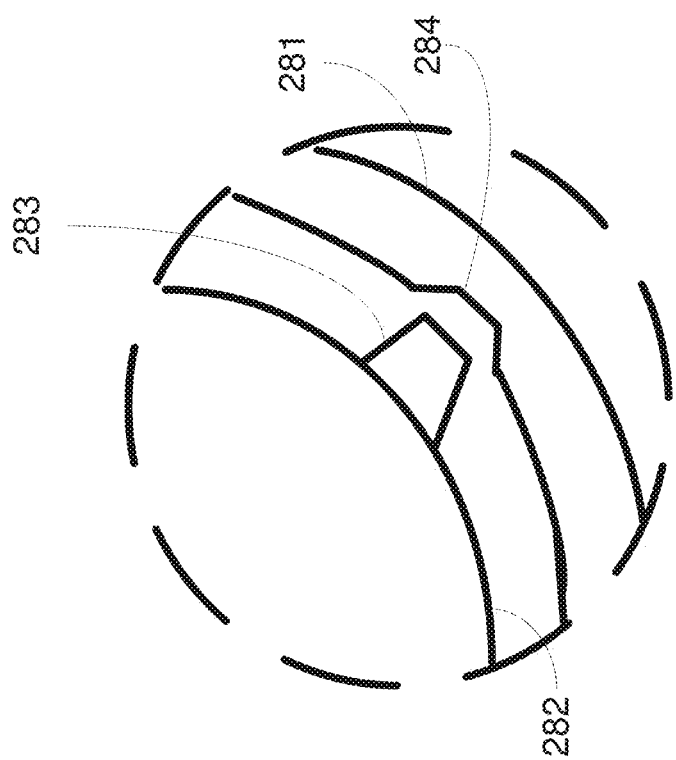
FIGS. 38A-38B illustrate the moving assembly and actuator assembly with rails on the actuator assembly in accordance with the principles of the present invention.
Figure 38A:
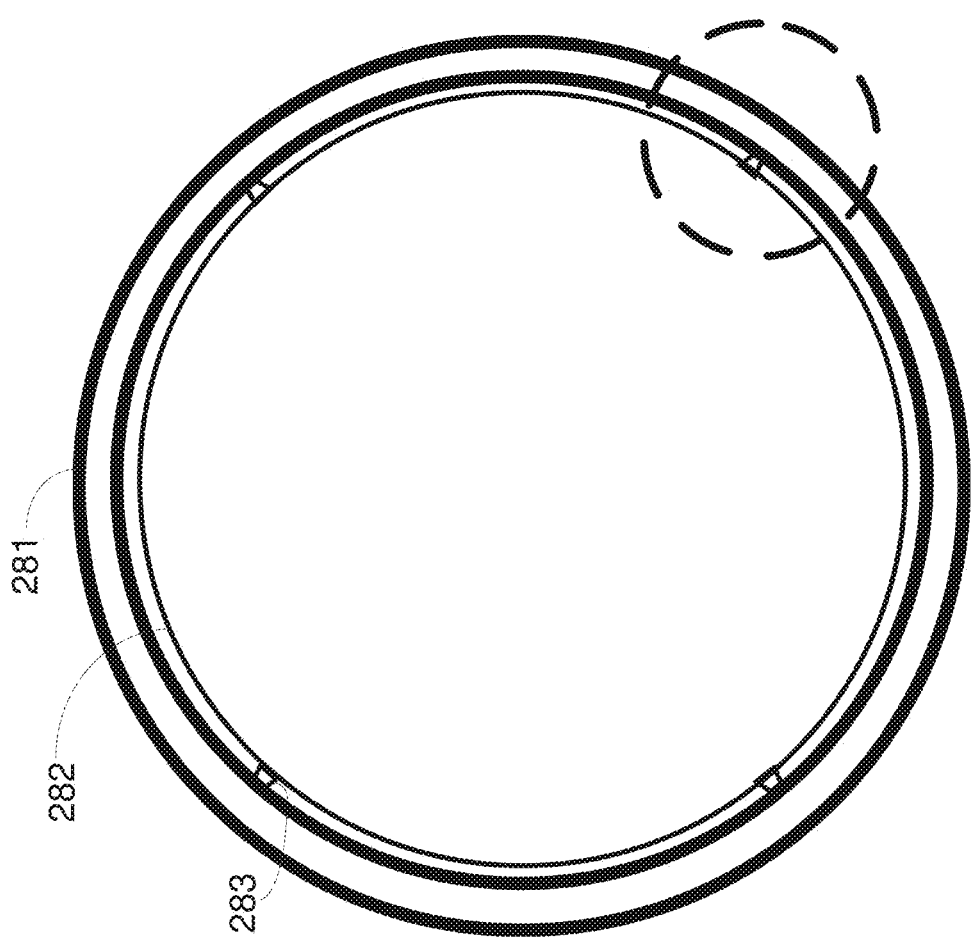

Referring now to FIGS. 38A and 38B, moving assembly 281 and actuator assembly 282 are illustrated. FIG. 38B is a close up view of FIG. 38A. Moving assembly 281 is substantially similar to moving assembly 251 and actuator assembly 282 is substantially similar to actuator assembly 252. As shown in FIG. 38A-B, actuator assembly 282 may be coupled to or otherwise incorporate rail 283 on an exterior surface. Moving assembly 281, at an exterior surface of moving assembly 281, may involve indentation 284 sized and configured to receive rail 283 or a portion thereof and may guide rail 283 along moving assembly 281. Rail 283 and/or indentation 284 may extend the length of actuator assembly 282 and/or moving assembly 281, respectively. Rail 283 is preferably positioned parallel to a central axis actuator assembly 282 and/or parallel to the range of motion of moving assembly 281. As shown in FIG. 38A, actuator assembly 282 may include 4 rails 283 that are equally spaced apart. Alternatively, any number of rails 283 may be incorporated into actuator assembly 282 that may or may not be equally spaced apart. For example, 3-12 rails may be incorporated into actuator assembly 282. Rail 283 and/or indentation 284 may be or incorporate a ceramic, such as Yttria-stabilized tetragonal zirconia polycrystal (Y-TZP) or zirconium-toughen alumina (ZTA), engineered plastics, such as poly-ether-ether-ketone (PEEK), poly-ether-ketone-ketone (PEKK) or Delrin, metals treated with low friction, wear-resistant coatings, such as diamond-like carbon (DLC) or titanium nitride, or similar low friction materials to reduce friction between rail 283 and indentation 284, if rail 283 comes into contact with indentation 284. Rail 283 and indentation 284 may function as a bearing or a portion of a bearing, such as a hydrodynamic or thin film bearing.

Referring now to FIG. 39, moving assembly 230, actuator assembly 293, magnetic assembly 291, skirt 203, post 216 and membrane 204 are illustrated. As explained above, moving portion 230 may include bearing portion 223, bearing portion 224, and magnet 225. Bearing 223 and bearing portion 224 may be in fluid communication with bearing portion 226 of actuator assembly 293. Magnet assembly 291 may be similar to magnet assembly 218 but may only include coil 292 which may be a singular coil. For example, coil 218 may be longer than coil 77 and 78. A current may be induced in coil 292 such that a magnetic force is generated. The magnetic force generated may vary depending upon the intensity of the current induced. By varying the intensity and/or direction of the current induced in coil 292, magnet 225 and thus moving assembly 251 may be caused to move up and down. For example, magnet 255 may be caused to move up or down along actuator assembly 293. With increased magnetic force caused by coil 292, moving assembly 230 may be caused to move a greater distance from a neutral position (e.g., near a center point of coil 292). The intensity of the magnetic force caused by coil 292 may be varied and/or selected to vary a frequency that moving assembly 251 reciprocates up and down. Actuator assembly 293 may be similar to actuator assembly 217 but may or may not include resistance magnets. Moving assembly 230 and/or post 216 may optionally be coupled to a mechanical spring to dampen movement of moving assembly 230, restrict the range of motion of moving assembly 230, and/or cause moving assembly 230 to return to a neutral position.

Figure 40B:
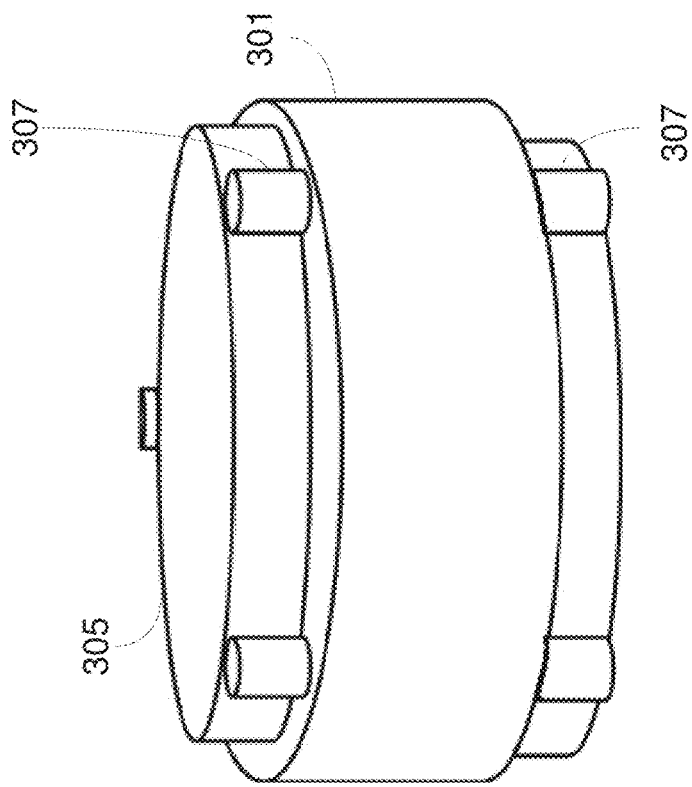
FIGS. 40A-40B illustrate the moving assembly and an actuator assembly with mechanical springs and at least one linear bearing portion in accordance with the principles of the present invention.
Figure 40A:
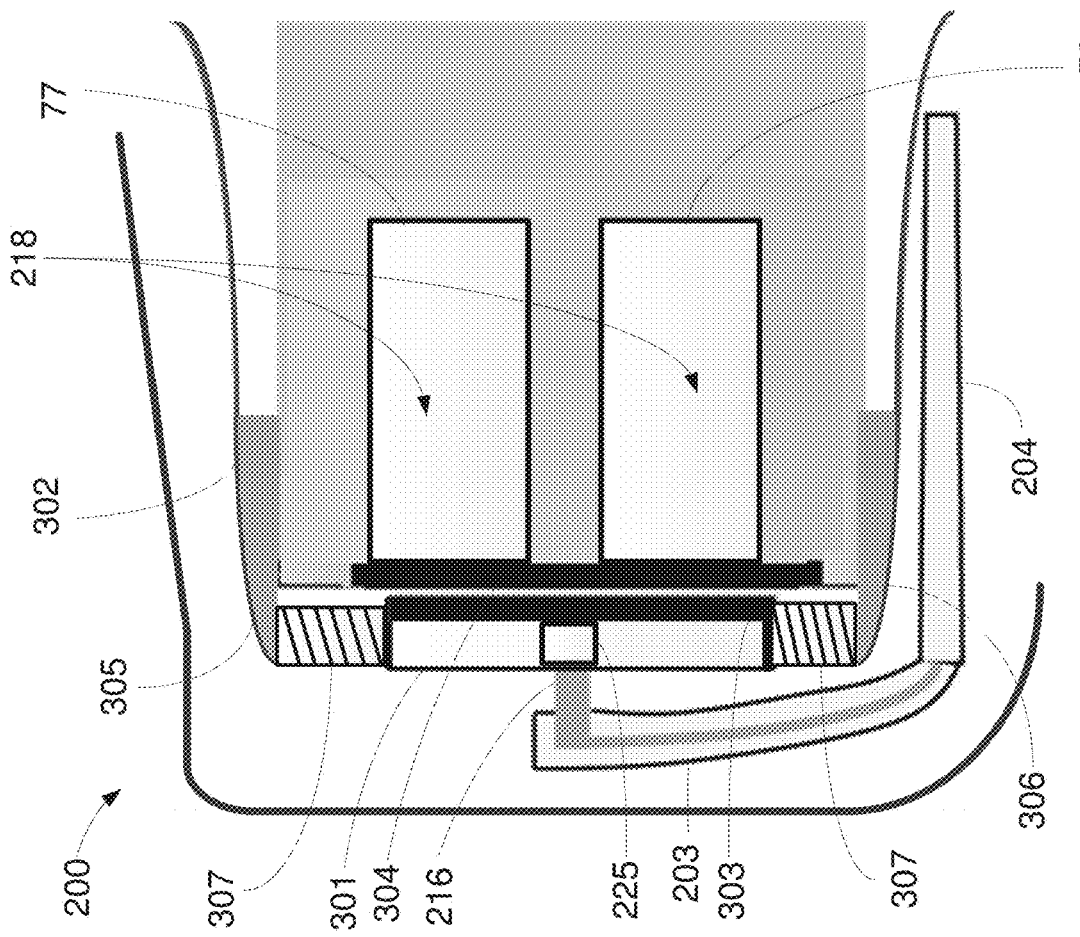

Referring now to FIG. 40A, pump housing 200, moving assembly 301, actuator assembly 302, mechanical springs 307, magnetic assembly 218, skirt 203, post 216 and membrane 204 are illustrated. Magnet assembly 218 may include a first coil (e.g., coil 77) and a second coil (e.g., coil 78). Moving assembly 301 is similar to moving assembly 230 but may have a tapered or non-tapered shaped. A tapered shape may be preferable to minimize damage to the blood and maintain the concentricity of moving assembly 301 with respect to the actuator assembly 302 by development of hydrodynamic forces. It is understood that moving assembly 301 may form any other shape, including but not limited to curved portions. Moving assembly 301 may include magnet 225 and bearing portion 303, similar to bearing portion 243. Actuator assembly 302 may be similar to actuator assembly 293 except that actuator assembly 302 may include bearing portion 304, which may the same as bearing portion 226, and may further include extended top portion 305 and extended bottom portion 306 which may protrude beyond an exterior wall of actuator assembly 301. Mechanical springs 307 may be coupled at one end to extended top portion 305 or extended bottom portion 306 and may be coupled to moving assembly 301 at the other end. Mechanical springs 307 may be coil springs or any other mechanical springs or dampers. Mechanical springs 307 may dampen movement of moving assembly 301, restrict the range of motion of moving assembly 301, and/or cause moving assembly 301 to return to a neutral position.

Referring now to FIG. 40B, a simplified drawing of actuator assembly 305, moving assembly 301, and mechanical springs 307 is illustrated. As shown in FIG. 40B, the pump assembly may include three pairs of mechanical springs 307, each pair including a top spring and a bottom spring coupled to moving assembly 301. It is understood, however, that any number of mechanical springs 307 may be used, such as four pairs of mechanical springs. While pairs of mechanical springs are illustrated in FIG. 40B with the top spring and bottom spring being coaxial, it is understood that top springs and bottom springs may not be coaxial. Mechanical springs 307 may or may not be spaced equally around actuator assembly 305.

Referring now to FIG. 41A, pump housing 200, moving assembly 301, actuator assembly 302, coil springs 308, magnetic assembly 218, skirt 203, post 216 and membrane 204 are illustrated. Moving assembly 301 may include magnet 225 and bearing portion 303. Magnet assembly 218 may include a rust coil (e.g., coil 77) and a second coil (e.g., coil 78). Actuator assembly 302 may include bearing portion 304 and may further include extended top portion 305 and extended bottom portion 306, which may protrude beyond an exterior wall of actuator assembly 301. Coil springs 308 may be coupled at one end to extended top portion 305 or extended bottom portion 306 and may be coupled to moving assembly 301 at the other end. Coil springs 308 may be singular large coil spring that completes one revolution around actuator assembly 305. Alternatively coil spring 308 may make multiple revolutions around actuator assembly 305. Coil springs 308 may dampen movement of moving assembly 301, restrict the range of motion of moving assembly 301, and/or cause moving assembly 301 to return to a neutral position.

Referring now to FIG. 41B, a simplified schematic of actuator assembly 305, moving assembly 301 and coil springs 308 is illustrated. As shown in FIG. 41B, the pump assembly may include two coil springs 308, one top spring and one bottom spring coupled to moving assembly 301. While coil springs 308 may be coupled to moving assembly 301 near the same point on moving assembly 301, it is understood that coil springs 308 may be coupled to moving assembly 301 and/or actuator assembly 305 at any point. It is further understood that coils springs 308 may not complete a full rotation around actuator assembly 305 and that more than two coil springs may be coupled to actuator assembly 305 and moving assembly 301.

Figure 42A:
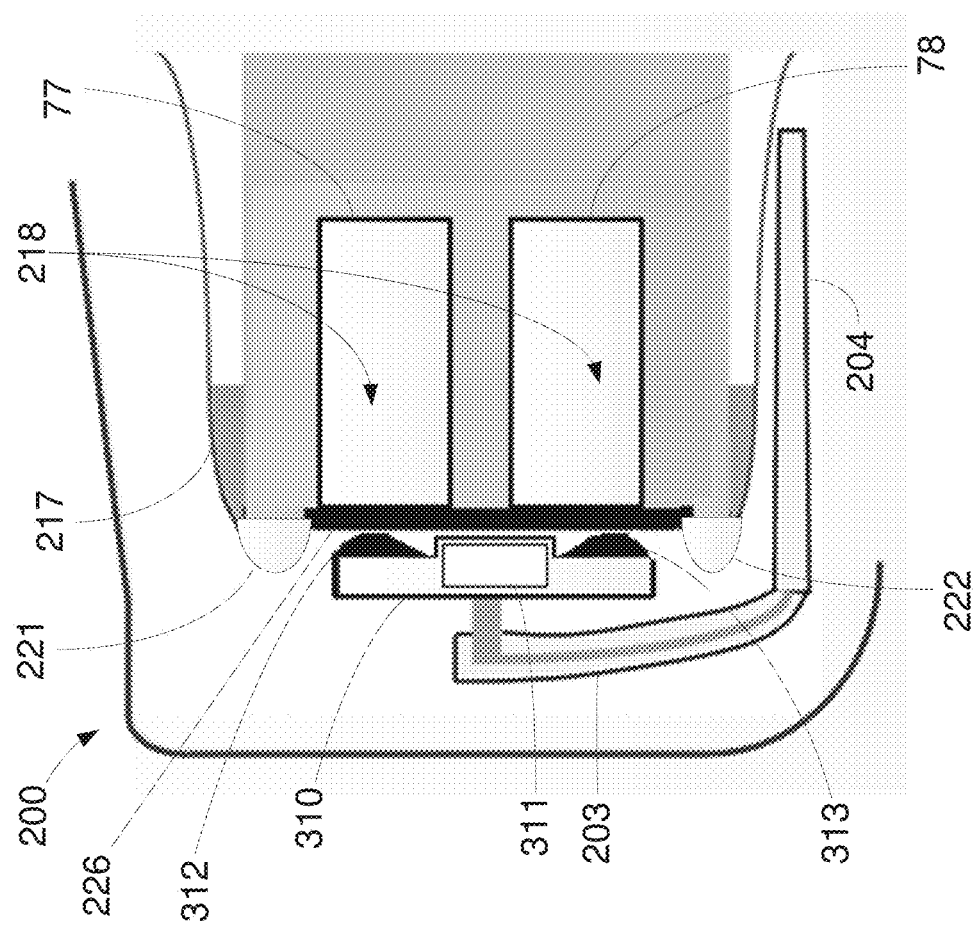
FIGS. 42A-42C illustrate a moving assembly with at least one bearing portion and an actuator assembly with at least one bearing portion, in accordance with the principles of the present invention.
Figure 42B:
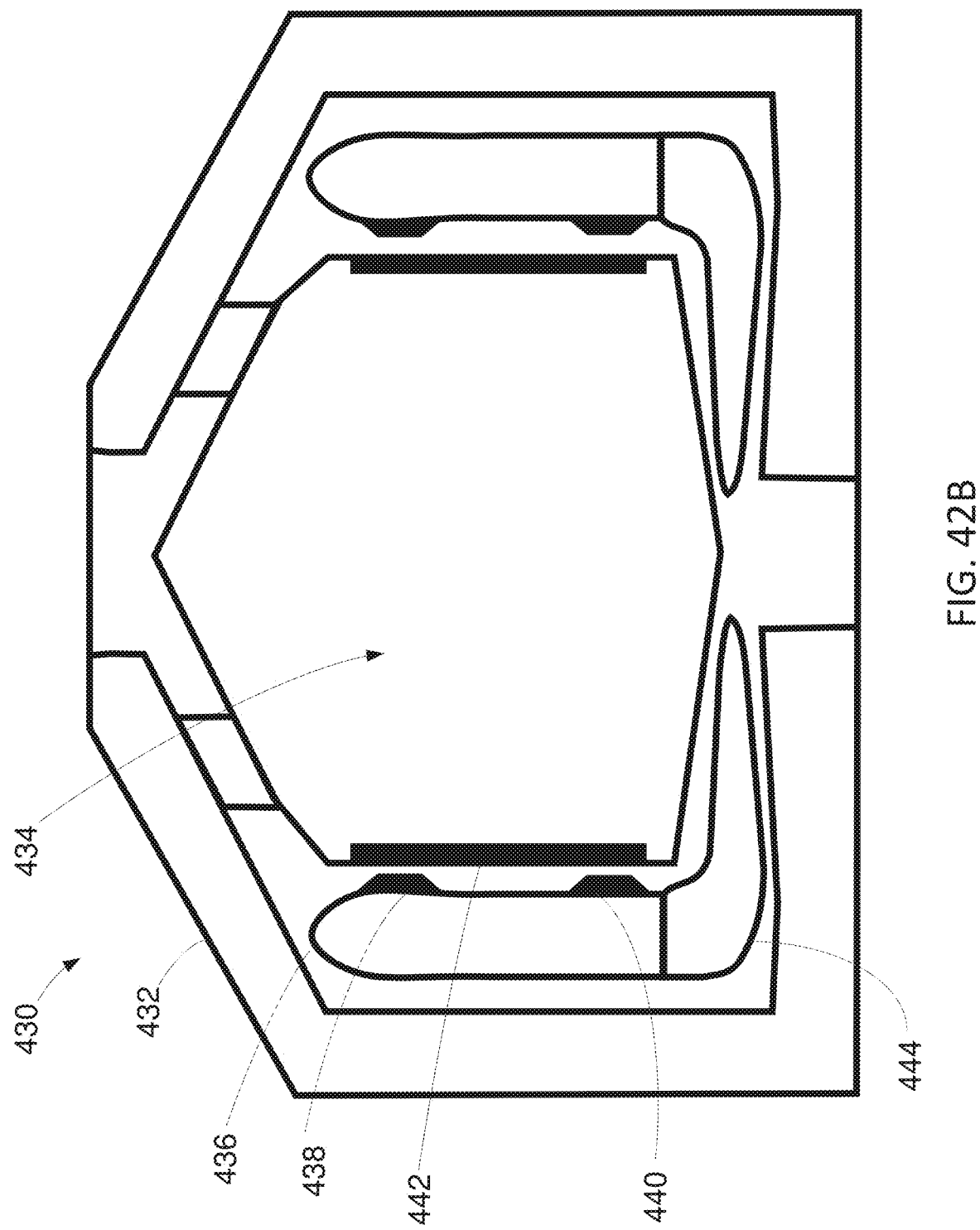
Figure 42C:
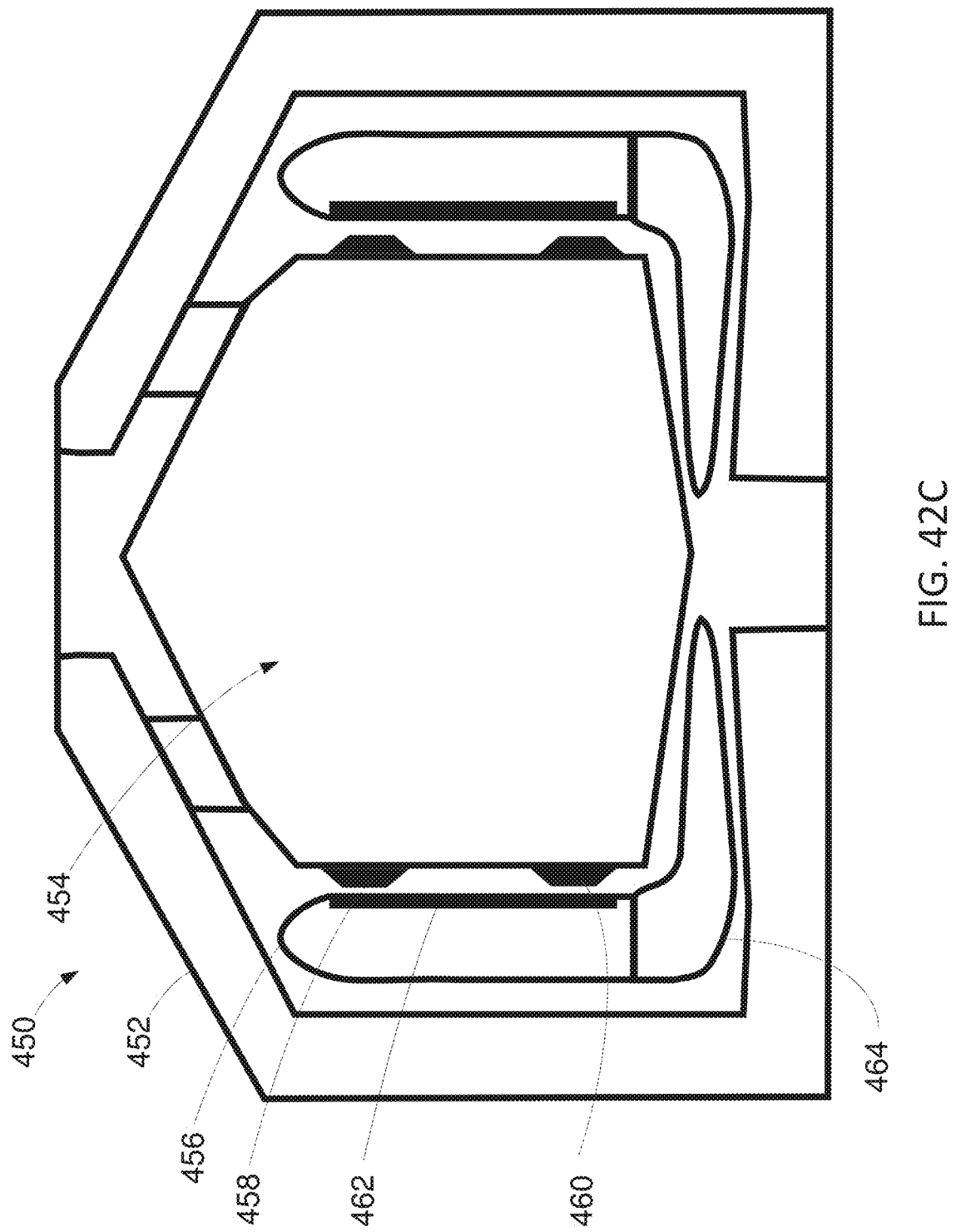

FIGS. 42A-C illustrate an implantable pump with one or more bearing portions on the actuator assembly. Referring now to FIG. 42A, pump housing 200, moving assembly 310, actuator assembly 217, magnetic assembly 218, skirt 203, post 216 and membrane 204 are illustrated. Actuator assembly 217 may include resistance magnet 221 and resistance magnet 222. Magnet assembly 218 may include coils 77 and 78. Moving assembly 310 may include magnet 311 which may be the same or similar to magnet 225 or may include one or more magnet portions. Bearing portions 312 and bearing portion 313 may be similar to bearing portion 223 and bearing portion 224 but may be dome-shaped, tapered and/or the shape of semi-circle. Bearing portion 312 and bearing portion 313 may protrude beyond an interior wall of moving assembly 310 housing magnet 311 or may protrude the same distance as the interior. Bearing portion 312 and bearing portion 313 may be in fluid communication with bearing portion 226 on actuator assembly 217.

Referring now to FIG. 42B, implantable pump 430 may include pump housing 432, similar to pump housing 200, and may further include actuator assembly 434 which may include one or more coils. Implantable pump 430 may further include moving assembly 436, which may be the same or similar to integrated assembly 406 of FIG. 16C, and may include a magnetic assembly. Moving assembly 436 may include bearing portion 438 and bearing portion 440, which may extend from moving assembly 436 and may be similar to bearing portions 223 and 224. For example, bearing portions 438 and 440 may be dome-shaped and/or tapered land bearings. Bearing portion 438 and bearing portion 440 may be in fluid communication with bearing portion 442, integrated into actuator assembly 434. Bearing portion 442 may be similar to bearing portion 226 and or may be a smooth and/or curved surface that extends along one or more portions of the outer wall of the actuator assembly 434. Bearing portions 442, 438 and 440 may maintain the radial distance between moving assembly 436 and actuator assembly 434. Any number of bearing portions may be arranged on the moving assembly and/or actuator assembly and the bearing portions may be arranged in any well-known pattern. In one example, 3-12 bearing portions may be arranged about the moving assembly and/or bearing portions may be arranged between 1-25 degrees circumferentially. As explained above, the bearing portions may be a tapered land bearing and/or dome shaped or alternatively smooth and/or curved.

Referring now to FIG. 42C, implantable pump 450 may include pump housing 452, similar to pump housing 200, and may further include actuator assembly 454 which may include one or more coils. Implantable pump 450 may further include moving assembly 456, which may be the same or similar to integrated assembly 406 of FIG. 16C, and may include a magnetic assembly (e.g., including a Halbach array). Moving assembly 456 may include bearing portion 462 which may be similar to bearing portion 226 and/or may be a smooth and/or curved surface that extends along one or more portions of the inner wall of the moving assembly 456. Bearing portion 462 may be in fluid communication with bearing portions 458 and 460, which may extend from actuator assembly 454. Bearing portions 458 and 460 may be similar to bearing portions 223 and 224. For example, bearing portions 458 and 460 may be dome-shaped and/or a tapered land bearing. Any number of bearing portions may be arranged on the actuator assembly and the bearing portions may be arranged with respect to the actuator assembly in any well-known pattern. In one example, 3-12 bearing portions may be arranged about the actuator assembly and/or bearing portions may be arranged between 1-25 degrees circumferentially. As explained above, the bearing portions may be tapered and/or dome shaped.

Figure 43A:
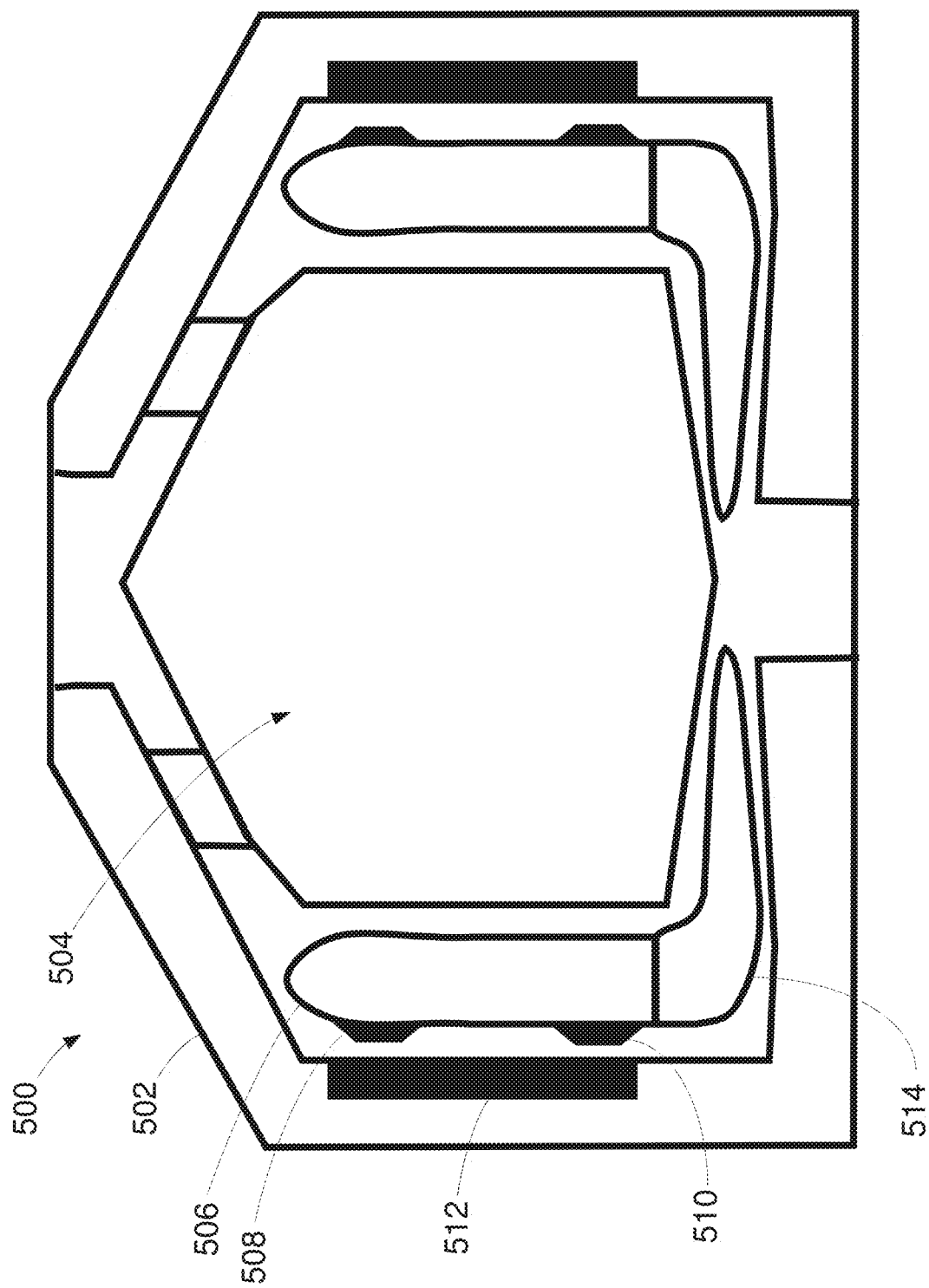
FIGS. 43A-43C illustrate the implantable pump with bearing portions arranged on the moving assembly, in accordance with the principles of the present invention.
Figure 43B:
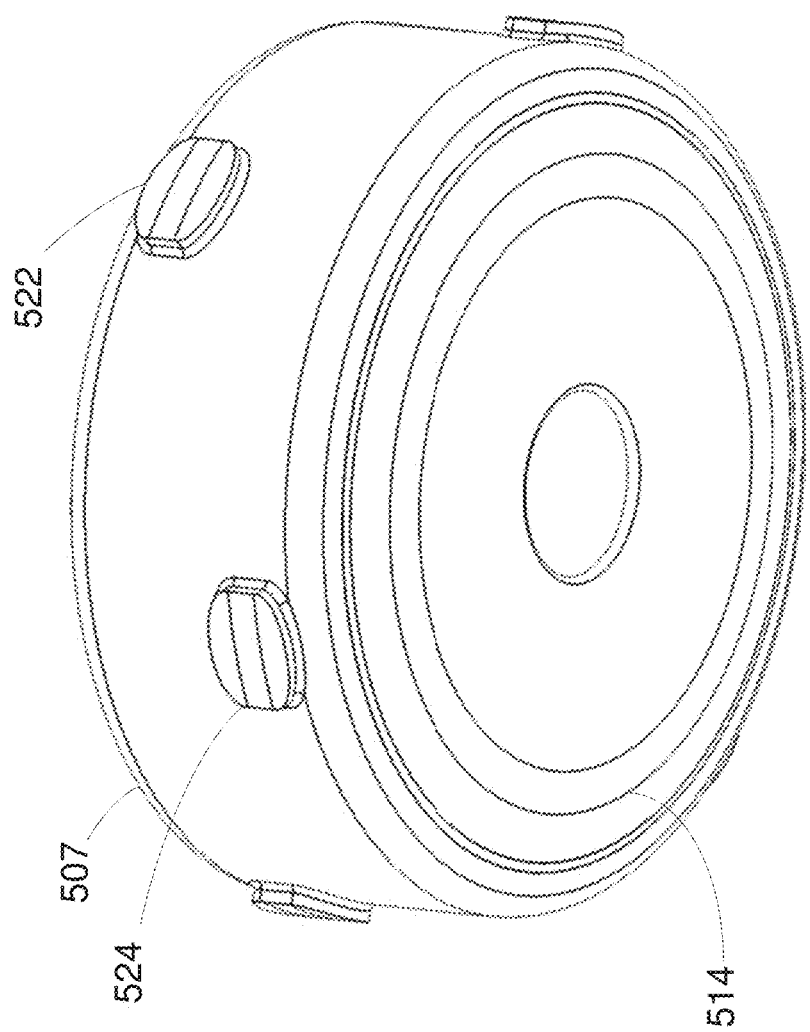
Figure 43C:
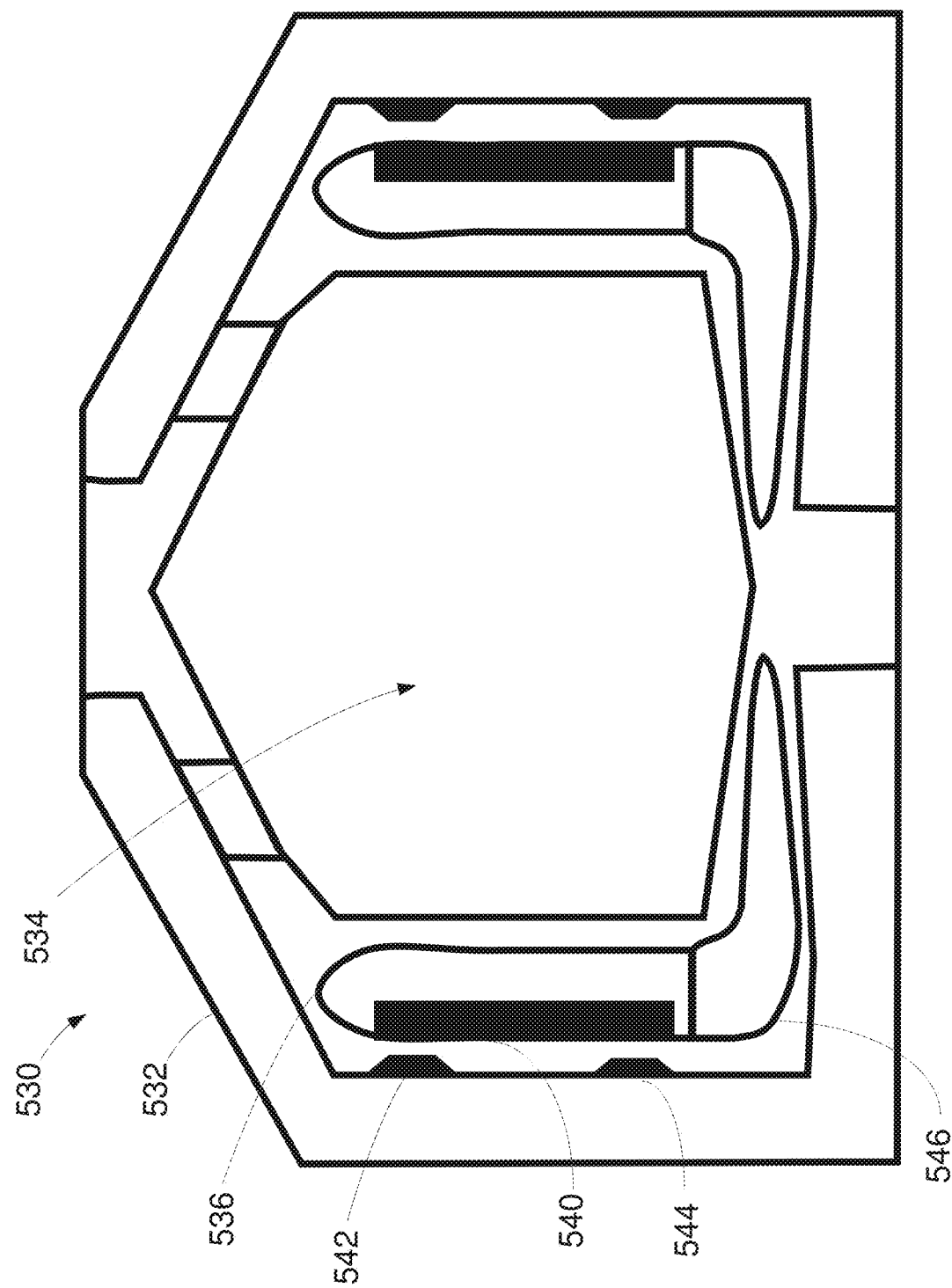

Referring now to FIGS. 43A-C, implantable pump 500 with bearing portions on the moving assembly and on the pump housing is illustrated. Like the implantable pump in FIG. 42A, implantable pump 500 may include pump housing 502, similar to pump housing 200, and may further include actuator assembly 504 which may include one or more coils. Implantable pump 500 may further include moving assembly 506, which may be the same or similar to integrated assembly 406 of FIG. 16C, and may include a magnetic assembly. Moving assembly 506 may include bearing portion 508 and bearing portion 510 which may extend from moving assembly 506 and may be similar to bearing portions 223 and 224. For example, bearing portions 508 and 510 may be dome-shaped and/or tapered land bearings. Bearing portion 508 and bearing portion 510 may be in fluid communication with bearing portion 512, integrated into pump housing 502. Bearing portion 512 may be similar to bearing portion 226 and or may be a smooth and/or curved surface that extends along one or more portions of the inner wall of the pump housing 502. Bearing portions 512, 508 and 510 may maintain the radial distance between moving assembly 506 and pump housing 502.

Referring now to FIG. 43B, a perspective view of a moving assembly 507 and membrane 514 is illustrated. As is shown in FIG. 43B, moving assembly 507 may be similar to moving assembly 506 but with bearing portions that are offset from one another. For example, bearing portion 522 and bearing portion 524 may be similar to bearing portions 508 and bearing portion 510, but may be circumferentially and axially distanced from one another. It is understood that any number of bearing portions may be arranged on the moving assembly and that the bearing portions may be arranged with respect to the moving assembly in any well-known pattern. In one example, 3-12 bearing portions may be arranged about the moving assembly and/or bearing portions may be arranged between 1-25 degrees circumferentially. As explained above, the bearing portions may be tapered and/or dome shaped.

Referring now to FIG. 43C, implantable pump 530 with bearing portions on the moving assembly and on the pump housing is illustrated. Like the implantable pump in FIG. 42A, implantable pump 530 may include pump housing 532, similar to pump housing 200, and may further include actuator assembly 534 which may include one or more coils. Implantable pump 530 may further include moving assembly 536, which may be the same or similar to integrated assembly 406 of FIG. 16C, and may include a magnetic assembly. Moving assembly 536 may include bearing portion 540 which may be incorporated into moving assembly 536 and may be similar to bearing portion 226. Specifically, bearing portion 540 may be a smooth and/or curved surface that extends along one or more portions of the outer wall of the moving assembly 546. Pump housing 532 may include bearing portions 542 and bearing portions 544, which may be similar to bearing portions 223 and 224. For example, bearing portions 542 and 544 may be dome-shaped and/or tapered land bearings. Bearing portions 542 and 544 may be in fluid communication with bearing portion 540 integrated into moving assembly 536. Bearing portions 542, 544 and 540 may be in fluid communication and may maintain the radial distance between moving assembly 536 and pump housing 532. Any number of bearing portions may be arranged on the pump housing. Further, the bearing portions may be arranged with respect to the moving assembly in any well-known pattern. In one example, 3-12 bearing portions may be arranged about the moving assembly and/or bearing portions may be arranged between 1-25 degrees circumferentially.

Figure 44A:
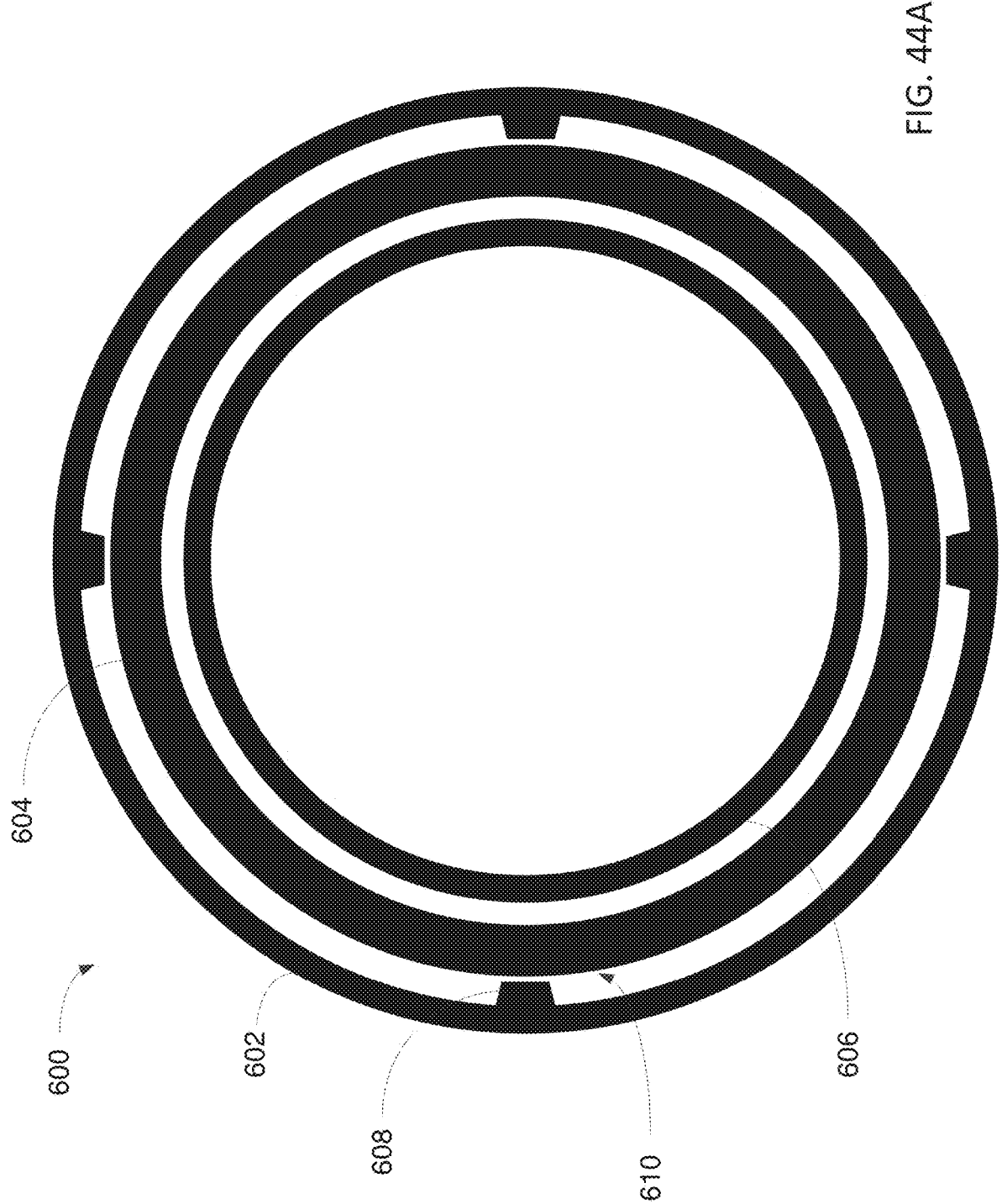
FIGS. 44A-44D illustrate top views of the implantable pump with various bearing configurations.

FIGS. 44A-D depict top views of various exemplary bearing arrangements of an implantable pump, which may be any implantable pump described herein. Referring now to FIG. 44A, implantable pump 600 is illustrated with bearing portions on pump housing 602 and moving assembly 604 (e.g., an integrated assembly). As shown in FIG. 44A, moving assembly 604 may be disposed around actuator assembly 606 and may be disposed within and adjacent to pump housing 602. Pump housing 602 may include one or more bearing portions 608 that may be may be similar to bearing portions 223 and 224 and/or may be dome-shaped and/or tapered land bearings. Additionally, moving assembly 604 may include bearing portion 610 which may be incorporated onto an outer surface of moving assembly 604 and may be similar to bearing portion 226. Specifically, bearing portion 610 may be smooth and/or curved surface that extends along one or more portions of the outer wall of moving assembly 604. Bearing portions 608 and 610 may be in fluid communication and may maintain the radial distance between moving assembly 604 and pump housing 602.

Figure 44B:
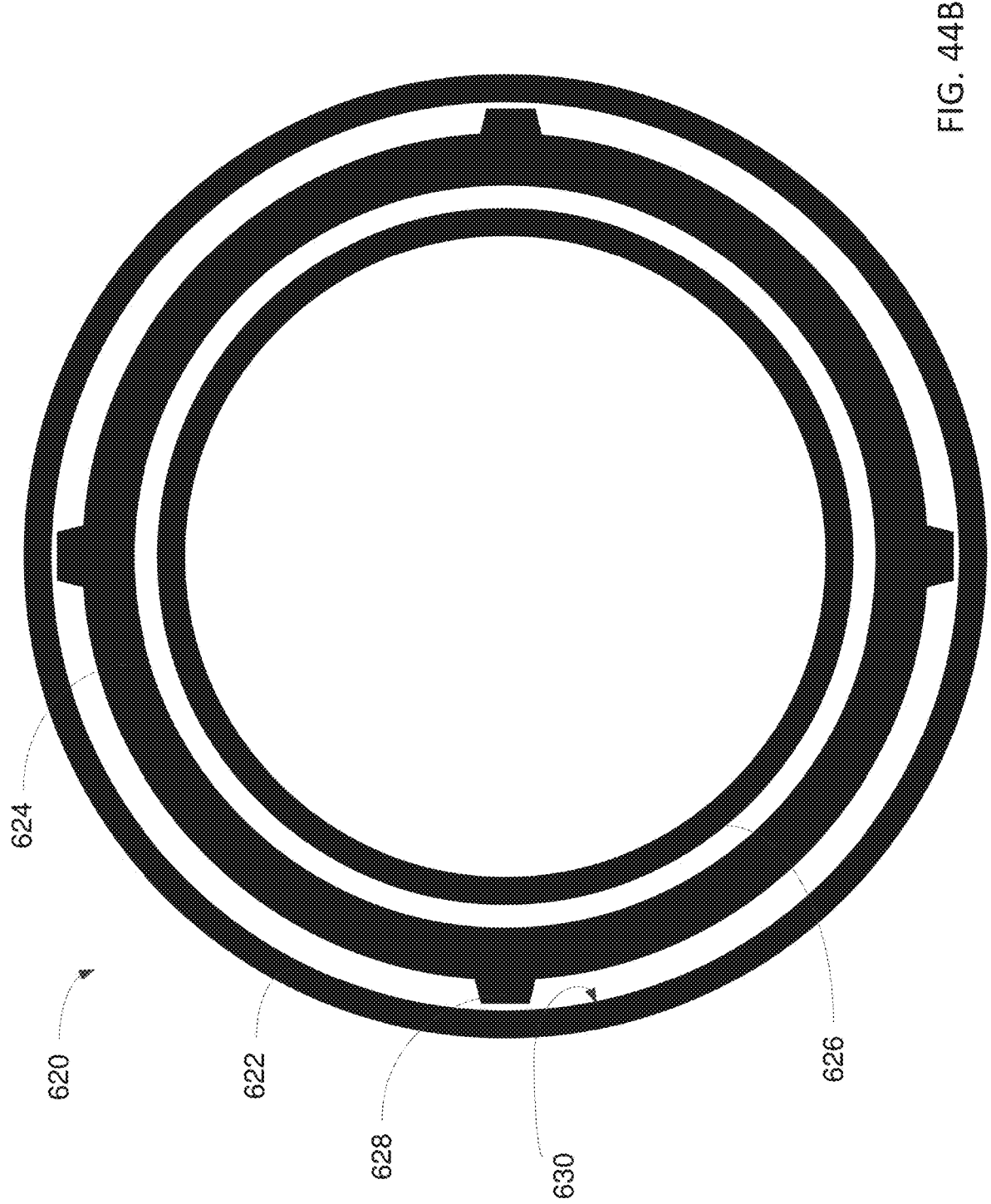

Referring now to FIG. 44B, implantable pump 620 is illustrated with bearing portions on pump housing 622 and moving assembly 624 (e.g., an integrated assembly). As shown in FIG. 44B, moving assembly 624 may be disposed around actuator assembly 626 and may be disposed within and adjacent to pump housing 622. Moving assembly 624 may include one or more bearing portions 628 on its outer surface that may be similar to bearing portions 223 and 224 and/or may be dome-shaped and/or tapered land bearings. Additionally, pump housing 622 may include bearing portion 630 which may be incorporated into an inner surface of pump housing 622 and may be similar to bearing portion 226. Specifically, bearing portion 630 may be a smooth and/or curved surface that extends along one or more portions of the inner wall of pump housing 622. Bearing portions 628 and 630 may be in fluid communication and may maintain the radial distance between moving assembly 624 and pump housing 622.

Figure 44C:
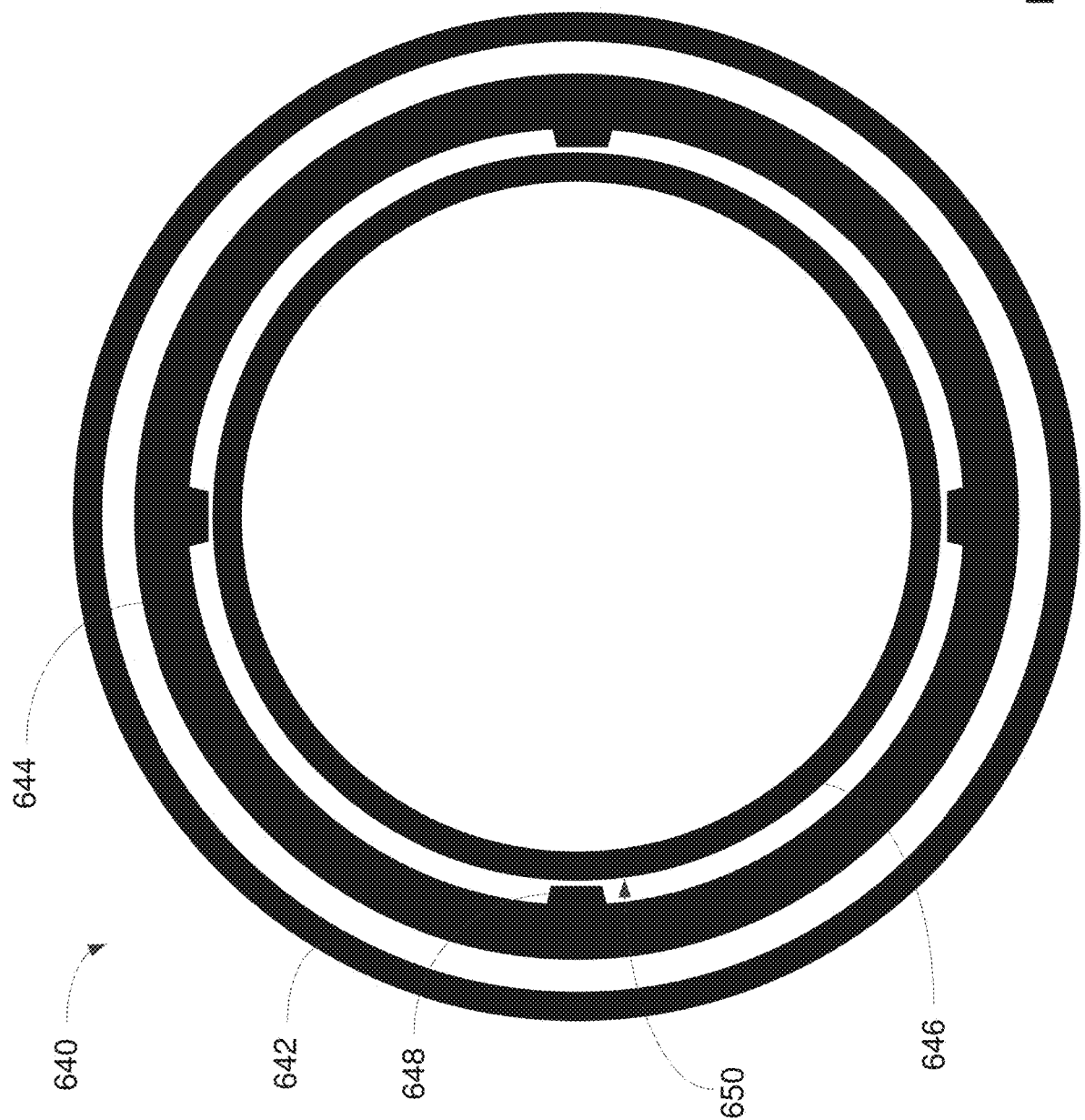

Referring now to FIG. 44C, implantable pump 640 is illustrated with bearing portions on actuator assembly 646 and moving assembly 644 (e.g., an integrated assembly). As shown in FIG. 44C, moving assembly 644 may be disposed around actuator assembly 646 and may be disposed within and adjacent to pump housing 642. Moving assembly 644 may include one or more bearing portions 648 on its inner surface that may be similar to bearing portions 223 and 224 and/or may be dome-shaped and/or tapered. Additionally, actuator assembly 646 may include bearing portion 650 which may be incorporated into an outer surface of actuator assembly 646 and may be similar to bearing portion 226. Specifically, bearing portion 650 may be a smooth and/or curved surface that extends along one or more portions of the outer wall of actuator assembly 646. Bearing portions 648 and 650 may be in fluid communication and may maintain the radial distance between moving assembly 644 and actuator assembly 646.

Figure 44D:
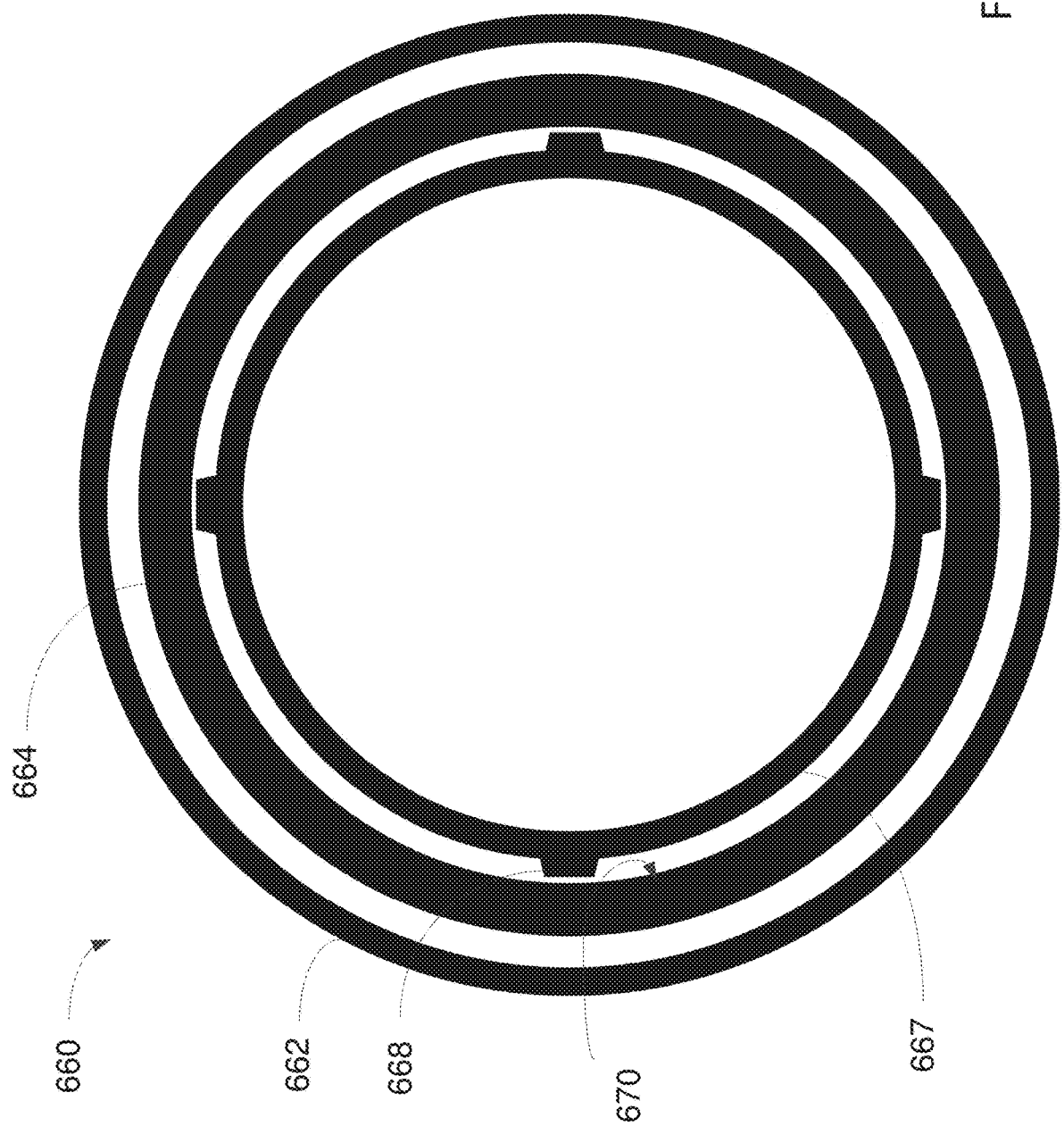

Referring now to FIG. 44D, implantable pump 660 is illustrated with bearing portions on actuator assembly 667 and moving assembly 664 (e.g., an integrated assembly). As shown in FIG. 44D, moving assembly 664 may be disposed around actuator assembly 667 and may be disposed within and adjacent to pump housing 662. Actuator assembly 667 may include one or more bearing portions 668 that may be may be similar to bearing portions 223 and 224 and/or may be dome-shaped and/or tapered. Additionally, moving assembly 664 may include bearing portion 670 which may be incorporated onto to an inner surface of moving assembly 664 and may be similar to bearing portion 226. Specifically, bearing portion 670 may be smooth and/or curved surface that extends along one or more portions of the inner wall of moving assembly 664. Bearing portions 668 and 670 may be in fluid communication and may maintain the radial distance between moving assembly 664 and actuator assembly 667.

While various illustrative embodiments of the invention are described above, it will be apparent to one skilled in the art that various changes and modifications may be made therein without departing from the invention. For example, pump assembly 70 shown in FIG. 9 may be ordered differently and may include additional or fewer components of various sizes and composition. The appended claims are intended to cover all such changes and modifications that fall within the true spirit and scope of the invention.

What is claimed:

1. A blood pump, comprising:
    a housing comprising an inlet and an outlet configured to be in fluid communication with a patient's circulatory system; and
    a pump assembly disposed within the housing, the pump assembly comprising an actuator assembly, a moving assembly, and a linear bearing, the pump assembly configured to cause linear reciprocating movement using the linear bearing to pump blood from the inlet to the outlet;
    wherein the linear reciprocating movement causes a pressure in the linear bearing that offsets the moving assembly from the actuator assembly.

2. The blood pump of claim 1, wherein the actuator assembly comprises a magnetic assembly, the magnetic assembly configured to selectively generate a magnetic field to cause the linear reciprocating movement.

3. The blood pump of claim 2, wherein the pump assembly further comprises a membrane coupled to the moving assembly, the moving assembly comprising at least one magnet configured to reciprocate responsive to the magnetic field generated by the actuator assembly.

4. The blood pump of claim 3, wherein the moving assembly comprises at least two magnets with polarity oriented in the same direction.

5. The blood pump of claim 3, wherein the moving assembly is concentrically suspended around the actuator assembly.

6. The blood pump of claim 3, wherein the housing further comprises at least one housing magnet configured to interact with the at least one magnet of the moving assembly to bias the moving assembly towards a neutral position.

7. The blood pump of claim 3, wherein:
    the linear bearing comprises a moving assembly bearing portion disposed on the moving assembly;
    the actuator assembly comprises an actuator assembly bearing portion disposed on the actuator assembly; and
    the actuator assembly bearing portion is in fluid communication with the moving assembly bearing portion and is positioned relative to the moving assembly bearing portion such that an opposing pressure force is generated between the moving assembly bearing portion and the actuator assembly bearing portion when the moving assembly moves with respect the actuator assembly.

8. The blood pump of claim 7, wherein the opposing pressure force causes the moving assembly bearing portion to assume an offset position a certain distance from the actuator assembly bearing portion as the moving assembly moves with respect the actuator assembly.

9. The blood pump of claim 7, wherein, during operation, blood enters the inlet and flows between the moving assembly bearing portion disposed on the moving assembly and the actuator assembly bearing portion disposed on the actuator assembly.

10. The blood pump of claim 3, wherein:
    the linear bearing comprises a moving assembly bearing portion disposed on the moving assembly;
    the housing comprises a housing bearing portion disposed on an interior of the housing; and
    the housing bearing portion is in fluid communication with the moving assembly bearing portion and is positioned relative to the moving assembly bearing portion such that an opposing pressure force is generated between the moving assembly bearing portion and the housing bearing portion when the moving assembly moves with respect the housing.

11. The blood pump of claim 10, wherein the opposing pressure force causes the moving assembly bearing portion to assume an offset position a certain distance from the housing bearing portion as the moving assembly moves with respect the housing.

12. The blood pump of claim 10, wherein, during operation, blood enters the inlet and flows between the moving assembly bearing portion disposed on the moving assembly and the housing bearing portion disposed on the housing.

13. The blood pump of claim 3, wherein the actuator assembly comprises at least one rail indentation and the moving assembly comprises at least one moving assembly bearing portion in fluid communication with the at least one rail indentation, the at least one rail indentation configured to guide the moving assembly with respect to the actuator assembly and to radially and circumferentially constrain the moving assembly with respect to the actuator assembly.

14. The blood pump of claim 3, wherein the moving assembly comprises at least one rail indentation and the actuator assembly comprises at least one actuator assembly bearing portion in fluid communication with the at least one rail indentation, the at least one rail indentation configured to guide the moving assembly with respect to the actuator assembly.

15. The blood pump of claim 3, wherein the actuator assembly comprises at least one coil coupled to the moving assembly that extends around the actuator assembly, and wherein the coil dampens linear movement of the moving assembly relative to the actuator assembly and returns the moving assembly to a neutral position.

16. The blood pump of claim 3, wherein the actuator assembly comprises at least one spring coupled to the moving assembly to dampen linear movement of the moving assembly relative to the actuator assembly and return the moving assembly to a neutral position.

17. The blood pump of claim 1, wherein the blood pump is configured to assist the patient's circulatory system without the use of valves.

18. The blood pump of claim 1, wherein the linear bearing comprises a tapered portion and comprises one or more of ceramic, alumina, zirconia, zirconia-toughened alumina, engineered plastic, or a metallic alloy coated with a tribologic coating.

19. A blood pump, comprising:
    a housing having an inlet and an outlet configured to be in fluid communication with a patient's circulatory system; and
    a pump assembly disposed within the housing, the pump assembly comprising an actuator, a bearing, a moving assembly, and a flexible membrane coupled to the moving assembly, the pump assembly configured to cause reciprocating movement using the bearing to cause the flexible membrane to move in a wave-like manner to pump blood from the inlet to the outlet;
    wherein the reciprocating movement causes a pressure in the bearing that offsets the moving assembly from the actuator.

20. The blood pump of claim 19, wherein the bearing is sized and configured to maintain a distance between the moving assembly and the actuator.

21. The blood pump of claim 19, wherein the bearing is sized and configured to minimize contact between the moving assembly and the actuator.

22. The blood pump of claim 19, wherein the actuator comprises a rail and the moving assembly is configured to engage the rail such that the bearing constrains radial and rotational displacement of the moving assembly with respect to the actuator.

23. The blood pump of claim 19, wherein the moving assembly comprises a first bearing portion and a second bearing portion and the first bearing portion is axially offset from the second bearing portion.

24. The blood pump of claim 19, wherein the moving assembly comprises a first bearing portion and a second bearing portion and the first bearing portion is circumferentially offset from the second bearing portion.

25. A blood pump, comprising:
- a housing having an inlet and an outlet configured to be in fluid communication with a patient's circulatory system;
- an actuator assembly coupled to the housing and comprising at least one coil configured to be selectively activated to generate a magnetic field, the actuator oriented with respect to the housing such that a flow channel is defined by the actuator and the housing;
- a moving assembly comprising a magnetic assembly configured to interact with the magnetic field, the moving assembly circumferentially disposed about the actuator assembly and situated in the flow channel, and the moving assembly configured to partition the flow channel into a first flow channel and a second flow channel;
- a flexible membrane coupled to the moving assembly and configured to propel blood from the inlet of the housing to the outlet of the housing; and
- a linear bearing coupled to at least the moving assembly;
- wherein the actuator assembly is configured to cause the moving assembly to reciprocate to causes a pressure in the linear bearing that offsets the moving assembly from the actuator.

26. The blood pump of claim 25, wherein the moving assembly is incorporated into a skirt.

27. The blood pump of claim 25, wherein the moving assembly and the flexible membrane form a continuous and uninterrupted partition of the flow channel.

28. The blood pump of claim 25, wherein the magnetic assembly comprises a Halbach array.

29. The blood pump of claim 25, wherein:
the linear bearing comprises a first bearing portion on an interior surface of the moving assembly and a second bearing portion on an exterior surface of the actuator assembly; and
the first bearing portion and the second bearing portion are in fluid communication and are configured generate an opposing pressure force when the moving assembly moves with respect to the actuator assembly.

30. The blood pump of claim 25, wherein:
the linear bearing comprises a first bearing portion on an exterior surface of the moving assembly and a second bearing portion on an interior surface of the housing; and
the first bearing portion and the second bearing portion are in fluid communication and are configured to generate an opposing pressure force when the moving assembly moves with respect to the housing.

* * * * *